(12) United States Patent
Shin et al.

(10) Patent No.: US 7,939,672 B2
(45) Date of Patent: May 10, 2011

(54) PHENYLACETATE DERIVATIVES OR PHARMACEUTICALLY ACCEPTABLE SALTS THEREOF, PREPARATION METHOD THEREOF AND COMPOSITION FOR PREVENTION OR TREATMENT OF DISEASES INDUCED BY ACTIVATION OF T-TYPE CALCIUM ION CHANNEL CONTAINING THE SAME AS AN ACTIVE INGREDIENT

(75) Inventors: Kye Jung Shin, Seoul (KR); Hyung Kook Lee, Seoul (KR); Eun Joo Roh, Seoul (KR); Dong Jin Kim, Seoul (KR); Kyung Il Choi, Seoul (KR); Hyewhon Rhim, Seoul (KR); Hye Jin Chung, Seoul (KR); Seon Hee Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 68 days.

(21) Appl. No.: 12/429,004

(22) Filed: Apr. 23, 2009

(65) Prior Publication Data

US 2010/0056545 A1    Mar. 4, 2010

(30) Foreign Application Priority Data

Aug. 28, 2008  (KR) ...................... 10-2008-0084563

(51) Int. Cl.
  *C07D 235/08*    (2006.01)
(52) U.S. Cl. .................................... 548/310.1
(58) Field of Classification Search ............... 548/310.1
  See application file for complete search history.

(56) References Cited

FOREIGN PATENT DOCUMENTS

| KR | 10-0743255 B1 | 7/2007 |
| KR | 10-0754325 B1 | 8/2007 |
| KR | 10-0784195 B1 | 12/2007 |

OTHER PUBLICATIONS

Lee, et al., Synthesis and Evaluation of α,α'-disubstituted Phenylacetate Derivatives for T-type Calcium Channel Blockers, Bioorganic & Medicinal Chemistry Letters, 18, 4424-4427 (2008); included in IDS.*

Khosravani, et al., "Effects of Cav3.2 channel mutations linked to idiopathic generalized epilepsy", Annals of Neurology, 2005, 57(5):745-749.

Vitko, et al., "Functional characterization and neuronal modeling of the effects of childhood absence epilepsy variants of CACNA1H, a T-type calcium channel", The Journal of Neuroscience, 2005, 25(19):4844-4855.

Barton, et al., "The antihyperalgesic effects of the T-type calcium channel blockers ethosuximide, trimethadione, and mibefradil", European Journal of Pharmacology, 2005, 521(1-3):79-85.

Berridge, et al., "Calcium signalling: Dynamics, homeostasis and remodelling", Nature Reviews: Molecular Cell Biology, 2003, 4:517-529.

Lee, et al., "Synthesis and evaluation of α,α'-disubstituted phenylacetate derivatives for T-type calcium channel blockers", Bioorganic & Medicinal Chemistry Letters, 2008, 18:4424-4427.

* cited by examiner

*Primary Examiner* — James O Wilson
*Assistant Examiner* — Erich A Leeser
(74) *Attorney, Agent, or Firm* — Lucas & Mercanti, LLP

(57) ABSTRACT

Disclosed herein are a new phenylacetate derivative represented by Chemical Formula 1 or pharmaceutically acceptable salt thereof, a preparation method thereof, and a composition for prevention or treatment of diseases induced by the activation of T-type calcium ion channels containing the same. The composition containing the phenylacetate derivative according to the present invention effectively inhibits the activation of T-type calcium ion channels and may be useful in the prevention or treatment of diseases such as hypertension, cancer, epilepsy, and neurogenic pains induced by the activation of T-type calcium ion channels.

[Chemical Formula 1]

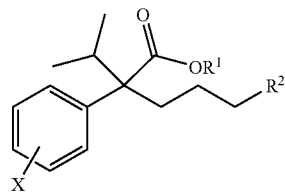

wherein, X, $R^1$, and $R^3$ are as defined herein.

10 Claims, No Drawings

PHENYLACETATE DERIVATIVES OR PHARMACEUTICALLY ACCEPTABLE SALTS THEREOF, PREPARATION METHOD THEREOF AND COMPOSITION FOR PREVENTION OR TREATMENT OF DISEASES INDUCED BY ACTIVATION OF T-TYPE CALCIUM ION CHANNEL CONTAINING THE SAME AS AN ACTIVE INGREDIENT

CROSS-REFERENCES TO RELATED APPLICATION

This patent application claims the benefit of priority under 35 U.S.C. §119 of Korean Patent Application No. 10-2008-0084563 filed on Aug. 28, 2008, the contents of which are incorporated herein by reference.

BACKGROUND OF THE INVENTION

1. Field of the Invention

The present invention relates to novel phenylacetate derivatives or pharmaceutically acceptable salts thereof, a preparation method thereof, and a composition for prevention or treatment of diseases induced by activation of a T-type calcium ion channel containing the same as an active ingredient.

2. Description of the Related Art

These calcium ion channels are divided into a high-voltage activated calcium channel and a low-voltage activated calcium channel, among which a T-type calcium ion channel is a representative low-voltage activated calcium channel.

Calcium ion channels play an important role in the intracellular signal transduction by increasing intracellular calcium concentration through nerve cell stimulation. These calcium channels are divided into a high-voltage activated calcium channel and a low-voltage activated calcium channel, and a T-type calcium ion channel is a representative example of the low-voltage activated calcium channels. The T-type calcium ion channel is found in central muscles, endocrine glands in the adrenal, sinoatrial node, and heart. A T-type calcium ion channel antagonist is known to have therapeutic effect on brain diseases, such as epilepsy and hypertension cardiac diseases, such as encephalopathy and angina pectoris [Hosravani, Houman et al., "Effects of Cav3.2 channel mutations linked to idiopathic generalized epilepsy", *Annals of Neurology* (2005), 57(5), 745-749; Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855]. A recent study reported that a T-type calcium ion channel antagonist has an activity in treatment of chronic pain [*Drugs of the Future* (2005), 40, 573-580]. For example, Mibefradil and Ethosuximide, as T-type calcium ion channel antagonists, showed dosage-dependent reversed mechanic and thermal induction in a spinal nerve ligation animal model, thus ascertaining that the T-type calcium ion channel antagonists have a therapeutic effect on neurogenic pains [Barton, Matthew E. et al., "The antihyperalgesic effects of the T-type calcium channel blockers ethosuximide, trimethadione, and mibefradil", *European Journal of Pharmacology* (2005), 521 (1-3), 79-85].

Calcium plays an important role as an intracellular messenger and regulates a variety of cellular processes. Calcium is known to be involved in cell growth among the cellular processes, and it is expected that a T-type calcium ion channel antagonist may have an anticancer activity [Nat. Rev. Mol. Cell Biol. 2003, 4, 517-529].

Calcium channel blockers can be classified into three classes: dihydropyridines (e.g., nifedipine), benzothiazepines (e.g., diltiazem), and phenylalkylamines (e.g., verapamil).

When the current is measured, a T-type calcium ion channel is activated at potential near the resting membrane potential, and the current is quickly activated and referred to as "transient" due to its fast inactivation. As the single channel conductance in the calcium ion channel has tiny characteristics compared to different calcium ion channels, the calcium ion channel is referred to as "T-type calcium ion channel" after the first alphabet representing these characteristics. Compared to other calcium ion channels, the T-type calcium ion channel has the activation of such a low threshold that it serves as a pacemaker, which produces simultaneous action potentials in the sinoatrial node and nerve cells, leading to the atrium contraction and is known to be involved in smooth muscle contraction, secretion of cortisol and aldosterone in adrenal cortex, excitability of Nerve, and development of tissues. In the T-type, 3 classes of the subtype cDNA are cloned and expressed. Each of them is expressed as $a_{1G}$ (Cav3.1), $a_{1H}$ (Cav3.2), and $a_{1I}$ (Cav3.3), and then the measured currents exhibit characteristics such as activation and inactivation reaction rates, slow activation reduction, and tiny single channel conductance as known in the art. However, the $a_{1I}$ shows very slow activation and inactivation reaction rates compared to the $a_{1G}$ and $a_{1H}$.

Much has not yet been known about the T-type due to the lack of the specific blockers, and more researches should be carried out. Recent studies show that in addition to functions by the calcium ion channels, such as muscular contraction, synaptic transmission, hormone secretion, control of enzyme activity, and control of gene expression, knockout of genes encoding calcium ion channels and a variety of hereditary diseases related to nerve, muscle, and visual sense are induced by mutation in the calcium ion channel. Thus, the importance of studies on calcium ion channels is being emphasized. Most of the calcium ion channel antagonists used in the studies as drugs have shown a physiological activity predominantly in the L-type calcium ion channels. However, these drugs show side effects such as excessive contraction of muscles, increased secretion from neurohormones, and coronary occlusion. Therefore, to reduce these side effects and enhance the efficacy of the drugs, screening efforts to find blockers which exhibit a selective activity to the T-type are underway.

Among the conventional calcium ion channel blockers, flunarizine, U-92032, nicardipine, and mibefradil are exemplary materials which show a selective inhibitory activity. These usually have diphenylmethylpiperazine or dihydropyridine structures as a basic framework.

Mibefradil is the first commercially available as a T-type calcium ion channel antagonist. The mibefradil showed more inhibitory activity to the T-type than to the L-type by 10 to 30 times, but was banned from the market due to drug interactions with antihistamines such as especially, astemizole to be metabolized in cytochrome P-450 3A4 and 2D6. Therefore, there remains a demand on urgent development of T-type calcium ion channels.

There have been many efforts to develop T-type calcium ion channel antagonists, but there are few selective T-type calcium ion channel antagonists. Compounds with quinazoline as a basic framework are disclosed in Korean Pat. Nos. 784,195, 754,325, and 749,743. Compounds with isoxazole as a framework are disclosed in Korean Pat. No. 616,099, and compounds with 1,3-dioxoisoindole as a framework are disclosed in Korean Pat. No. 743,255.

However, there still remains a demand on T-type calcium ion channel antagonists with good selectivity to T-type calcium ion channels, good pharmacokinetics profile, good ADME (adsorption, distribution, metabolism, excretion) and having a therapeutic effect on related diseases such as hypertension, cancer, epilepsy, and neurogenic pains. Thus, there is a need to develop materials which have a different structure from conventional T-type calcium ion channel antagonists and a higher selectivity.

The present inventors attempted to develop novel T-type calcium ion channel antagonists which may effectively inhibit the activity of T-type calcium ion channels, synthesized novel phenylacetate derivatives, and confirmed that the phenylacetate derivatives show the inhibitory activity of T-type calcium ion channels, thereby leading to completion of the present invention.

SUMMARY OF THE INVENTION

The object of the present invention is to provide phenylacetate derivatives which may effectively inhibit T-type calcium ion channels, or pharmaceutically acceptable salts thereof.

Another object of the present invention is to provide intermediates when the phenylacetate derivatives are prepared.

Further object of the present invention is to provide a composition for prevention and treatment of diseases cause by the activity of T-type calcium ion channels, containing phenylacetate derivatives or pharmaceutically acceptable salts thereof as an effective ingredient.

To achieve the objects, the present invention provides new phenylacetate derivatives or pharmaceutically acceptable salts thereof.

The present invention also provides a preparation method of the phenylacetate derivatives.

Furthermore, the present invention provides intermediates when the phenylacetate derivatives are prepared.

The present invention also provides a composition for prevention and treatment of diseases cause by the activity of T-type calcium ion channels, containing phenylacetate derivatives or pharmaceutically acceptable salts thereof as an effective ingredient.

The composition containing the phenylacetate derivatives according to the present invention effectively inhibits the activity of T-type calcium ion channels and may be useful for prevention or treatment of diseases such as hypertension, cancer, epilepsy, and neurogenic pains induced by the activity of T-type calcium ion channels.

The present invention provides phenylacetate derivatives represented by the following Chemical Formula 1, or pharmaceutically acceptable salts thereof.

[Chemical Formula 1]

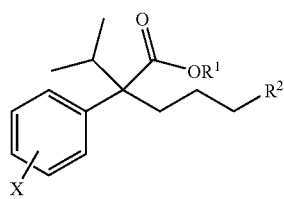

Where,

X is independently or selectively one or more substituents selected from the group consisting of H, halogen, and a $C_{1-4}$ alkoxy, $R^1$ is a $C_{1-4}$ linear or branched alkyl, $R^2$ is

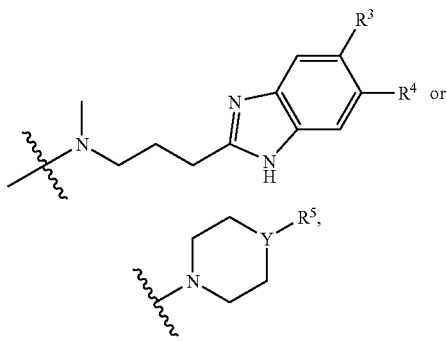

where $R^3$ and $R^4$ are independently or selectively H, a $C_{1-4}$ linear or branched alkyl, or a $C_{1-4}$ alkoxy, and Y is C or N.

$R^5$ is a $C_{1-4}$ linear or branched alkyl substituted by one or more $C_{5-6}$ aryl; unsubstituted, or one or more halogens, a $C_{1-4}$ linear or branched alkyl, a $C_{1-4}$ linear or branched alkyl substituted by one or more halogens, or phenyl substituted by a $C_{1-4}$ alkoxy; unsubstituted, or one or more halogens, a $C_{1-4}$ linear or branched alkyl, a $C_{1-4}$ linear or branched alkyl substituted by one or more halogens, or benzyl substituted by a $C_{1-4}$ alkoxy; or unsubstituted, or one or more halogens, a $C_{1-4}$ linear or branched alkyl, a $C_{1-4}$ linear or branched alkyl substituted by one or more halogens, or benzylidene substituted by a $C_{1-4}$ alkoxy.

Preferably,

X is independently or selectively one or more substituents selected from the group consisting of H, fluoride, chloride, bromide, methoxy and ethoxy, $R^1$ is methyl, ethyl, propyl, and isopropyl, $R^2$ is

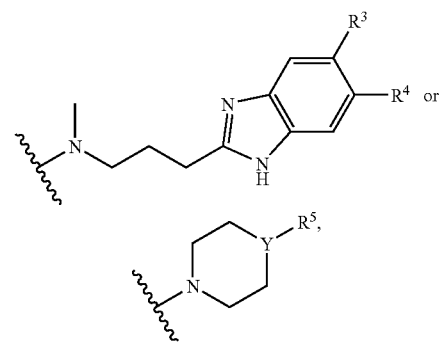

where $R^3$ and $R^4$ are independently or selectively H, methyl, ethyl, methoxy or ethoxy, and Y is C or N.

$R^5$ is benzhydryl; unsubstituted, or one or more fluoride, chloride, bromide, methyl, ethyl, methyl substituted by one or more fluorides, and phenyl substituted by methoxy or ethoxy; unsubstituted, or one or more fluoride, chloride, bromide, methyl, ethyl, methyl substituted by one or more fluorides, and benzyl substituted by methoxy or ethoxy; or unsubstituted, or benzylidene substituted by one or more fluoride, chloride, bromide, methyl, ethyl, methoxy or ethoxy.

More preferably,

X is one or more substituents selected from the group consisting of H, fluoride, bromide and ethoxy, $R^1$ is methyl or ethyl, $R^2$ is

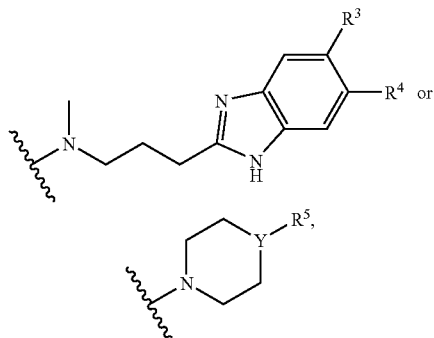

where $R^3$ and $R^4$ are independently or selectively H, methyl or methoxy,

Y is C or N, and $R^5$ is benzhydryl, phenyl, fluorophenyl, chlorophenyl, methoxyphenyl, fluorobenzyl, trifluoromethylbenzyl, chlorobenzyl, dichlorobenzyl, 2-chloro-6-fluorobenzyl, methylbenzyl, t-butylbenzyl, methoxybenzyl, trimethoxybenzyl, fluorobenzylidene, chlorobenzylidene, methylbenzylidene or methoxybenzylidene.

The piperidine derivatives represented by the Chemical Formula 1 are more specifically described as followings:

(1) 5-{[3-(1H-benzimidazole-2-yl)propyl]methylamino}-2-(4-bromophenyl)-2-isopropylpentanoic acid methyl ester;

(2) 2-(4-bromophenyl)-2-isopropyl-5-(4-phenylpiperazine-1-yl)pentanoic acid methyl ester;

(3) 2-(4-bromophenyl)-2-isopropyl-5-[4-(4-methoxybenzylidene)piperidine-1-yl]pentanoic acid methyl ester;

(4) methyl 5-((3-(1H-benzo[d]imidazole-2-yl)propyl)(methyl))amino)-2-isopropyl-2-(4-methoxyphenyl)pentanoate;

(5) methyl 2-isopropyl-5-((3-(5-methoxy-1H-benzo[d]imidazole-2-yl)propyl)(methyl))amino)-2-(4-methoxyphenyl)pentanoate;

(6) methyl 5-((3-(5,6-dimethyl-1H-benzo[d]imidazole-2-yl)propyl)(methyl))amino)-2-isopropyl-2-(4-methoxyphenyl)pentanoate;

(7) methyl 5-((3-(1H-benzo[d]imidazole-2-yl)propyl)(methyl))amino)-2-(3,4-dimethoxyphenyl)-2-isopropylpentanoate;

(8) methyl 2-(3,4-dimethoxyphenyl)-2-isopropyl-5-((3-(5-methoxy-1H-benzo[d]imidazole-2-yl)propyl)(methyl))amino)pentanoate;

(9) methyl 2-(3,4-dimethoxyphenyl)-5-((3-(5,6-dimethyl-1H-benzo[d]imidazole-2-yl)propyl)(methyl))amino)-2-isopropylpentanoate;

(10) ethyl 5-((3-(1H-benzo[d]imidazole-2-yl)propyl)(methyl))amino)-2-isopropyl-2-phenylpentanoate;

(11) ethyl 5-((3-(5,6-dimethyl-1H-benzo[d]imidazole-2-yl)propyl)(methyl))amino)-2-isopropyl-2-phenylpentanoate;

(12) methyl 2-(4-bromophenyl)-5-((3-(5,6-dimethyl-1H-benzo[d]imidazole-2-yl)propyl)(methyl))amino)-2-isopropylpentanoate;

(13) methyl 2-(4-bromophenyl)-2-isopropyl-5-((3-(5-methoxy-1H-benzo[d]imidazole-2-yl)propyl)(methyl))amino)pentanoate;

(14) methyl 5-((3-(1H-benzo[d]imidazole-2-yl)propyl)(methyl))amino)-2-(3-bromophenyl)-2-isopropylpentanoate;

(15) methyl 2-(3-bromophenyl)-2-isopropyl-5-((3-(5-methoxy-1H-benzo[d]imidazole-2-yl)propyl)(methyl))amino)pentanoate;

(16) methyl 2-(3-bromophenyl)-5-((3-(5,6-dimethyl-1H-benzo[d]imidazole-2-yl)propyl)(methyl))amino)-2-isopropylpentanoate;

(17) methyl 5-((3-(1H-benzo[d]imidazole-2-yl)propyl)(methyl))amino)-2-(4-fluorophenyl)-2-isopropylpentanoate;

(18) methyl 2-(4-fluorophenyl)-2-isopropyl-5-((3-(5-methoxy-1H-benzo[d]imidazole-2-yl)propyl)(methyl))amino)pentanoate;

(19) methyl 5-((3-(5,6-dimethyl-1H-benzo[d]imidazole-2-yl)propyl)(methyl))amino)-2-(4-fluorophenyl)-2-isopropylpentanoate;

(20) ethyl 2-isopropyl-5-(4-(2-methoxyphenyl)piperazine-1-yl)-2-phenylpentanoate;

(21) ethyl 2-isopropyl-5-(4-(3-methoxyphenyl)piperazine-1-yl)-2-phenylpentanoate;

(22) ethyl 2-isopropyl-5-(4-(4-methoxyphenyl)piperazine-1-yl)-2-phenylpentanoate;

(23) ethyl 2-isopropyl-5-(4-(4-methoxybenzyl)piperazine-1-yl)-2-phenylpentanoate;

(24) ethyl 5-(4-(2-fluorophenyl)piperazine-1-yl)-2-isopropyl-2-phenylpentanoate;

(25) ethyl 5-(4-(4-fluorophenyl)piperazine-1-yl)-2-isopropyl-2-phenylpentanoate;

(26) ethyl 5-(4-(4-fluorobenzyl)piperazine-1-yl)-2-isopropyl-2-phenylpentanoate;

(27) methyl 5-(4-benzhydrylpiperazine-1-yl)-2-(4-bromophenyl)-2-isopropylpentanoate;

(28) methyl 2-(4-bromophenyl)-5-(4-(2-fluorophenyl)piperazine-1-yl)-2-isopropylpentanoate;

(29) methyl 2-(4-bromophenyl)-5-(4-(4-fluorophenyl)piperazine-1-yl)-2-isopropylpentanoate;

(30) methyl 2-(4-bromophenyl)-5-(4-(2-fluorobenzyl)piperazine-1-yl)-2-isopropylpentanoate;

(31) methyl 2-(4-bromophenyl)-5-(4-(3-fluorobenzyl)piperazine-1-yl)-2-isopropylpentanoate;

(32) methyl 2-(4-bromophenyl)-5-(4-(4-fluorobenzyl)piperazine-1-yl)-2-isopropylpentanoate;

(33) methyl 2-(4-bromophenyl)-2-isopropyl-5-(4-(3-(trifluoromethyl)benzyl)piperazine-1-yl)pentanoate;

(34) methyl 2-(4-bromophenyl)-2-isopropyl-5-(4-(4-(trifluoromethyl)benzyl)piperazine-1-yl)pentanoate;

(35) methyl 2-(4-bromophenyl)-2-isopropyl-5-(4-(2-methoxyphenyl)piperazine-1-yl)pentanoate;

(36) methyl 2-(4-bromophenyl)-2-isopropyl-5-(4-(3-methoxyphenyl)piperazine-1-yl)pentanoate;

(37) methyl 2-(4-bromophenyl)-2-isopropyl-5-(4-(4-methoxyphenyl)piperazine-1-yl)pentanoate;

(38) methyl 2-(4-bromophenyl)-2-isopropyl-5-(4-(4-methoxybenzyl)piperazine-1-yl)pentanoate;

(39) methyl 2-(4-bromophenyl)-2-isopropyl-5-(4-(2,3,4-trimethoxybenzyl)piperazine-1-yl)pentanoate;

(40) methyl 2-(4-bromophenyl)-2-isopropyl-5-(4-(3-methylbenzyl)piperazine-1-yl)pentanoate;

(41) methyl 2-(4-bromophenyl)-2-isopropyl-5-(4-(4-methylbenzyl)piperazine-1-yl)pentanoate;

(42) methyl 2-(4-bromophenyl)-5-(4-(4-t-butylbenzyl)piperazine-1-yl)-2-isopropylpentanoate;

(43) methyl 2-(4-bromophenyl)-5-(4-(3-chlorophenyl)piperazine-1-yl)-2-isopropylpentanoate;

(44) methyl 2-(4-bromophenyl)-5-(4-(3-chlorobenzyl)piperazine-1-yl)-2-isopropylpentanoate;
(45) methyl 2-(4-bromophenyl)-5-(4-(4-chlorobenzyl)piperazine-1-yl)-2-isopropylpentanoate;
(46) methyl 2-(4-bromophenyl)-5-(4-(3,4-dichlorobenzyl)piperazine-1-yl)-2-isopropylpentanoate;
(47) methyl 2-(4-bromophenyl)-5-(4-(2-chloro-6-fluorobenzyl)piperazine-1-yl)-2-isopropylpentanoate;
(48) methyl 2-(3-bromophenyl)-5-(4-(2-fluorobenzyl)piperazine-1-yl)-2-isopropylpentanoate;
(49) methyl 2-(3-bromophenyl)-5-(4-(3-fluorobenzyl)piperazine-1-yl)-2-isopropylpentanoate;
(50) methyl 2-(3-bromophenyl)-5-(4-(4-fluorobenzyl)piperazine-1-yl)-2-isopropylpentanoate;
(51) methyl 2-(3-bromophenyl)-2-isopropyl-5-(4-(3-(trifluoromethyl)benzyl)piperazine-1-yl)pentanoate;
(52) methyl 2-(3-bromophenyl)-2-isopropyl-5-(4-(4-(trifluoromethyl)benzyl)piperazine-1-yl)pentanoate;
(53) methyl 2-(3-bromophenyl)-2-isopropyl-5-(4-(4-methoxybenzyl)piperazine-1-yl)pentanoate;
(54) methyl 2-(3-bromophenyl)-2-isopropyl-5-(4-(3,4,5-trimethoxybenzyl)piperazine-1-yl)pentanoate;
(55) methyl 2-(3-bromophenyl)-2-isopropyl-5-(4-(3-methylbenzyl)piperazine-1-yl)pentanoate;
(56) methyl 2-(3-bromophenyl)-2-isopropyl-5-(4-(4-methylbenzyl)piperazine-1-yl)pentanoate;
(57) methyl 2-(3-bromophenyl)-5-(4-(4-t-butylbenzyl)piperazine-1-yl)-2-isopropylpentanoate;
(58) methyl 2-(3-bromophenyl)-5-(4-(3-chlorobenzyl)piperazine-1-yl)-2-isopropylpentanoate;
(59) methyl 2-(3-bromophenyl)-5-(4-(4-chlorobenzyl)piperazine-1-yl)-2-isopropylpentanoate;
(60) methyl 2-(3-bromophenyl)-5-(4-(3,4-dichlorobenzyl)piperazine-1-yl)-2-isopropylpentanoate;
(61) methyl 2-(4-fluorophenyl)-2-isopropyl-5-(4-phenylpiperazine-1-yl)pentanoate;
(62) methyl 5-(4-benzhydrylpiperazine-1-yl)-2-(4-fluorophenyl)-2-isopropylpentanoate;
(63) methyl 2-(4-fluorophenyl)-5-(4-(2-fluorobenzyl)piperazine-1-yl)-2-isopropylpentanoate;
(64) methyl 2-(4-fluorophenyl)-5-(4-(4-fluorobenzyl)piperazine-1-yl)-2-isopropylpentanoate;
(65) methyl 5-(4-(2-fluorobenzyl)piperazine-1-yl)-2-(4-fluorophenyl)-2-isopropylpentanoate;
(66) methyl 5-(4-(3-fluorobenzyl)piperazine-1-yl)-2-(4-fluorophenyl)-2-isopropylpentanoate;
(67) methyl 5-(4-(4-fluorobenzyl)piperazine-1-yl)-2-(4-fluorophenyl)-2-isopropylpentanoate;
(68) methyl 2-(4-fluorophenyl)-2-isopropyl-5-(4-(3-(trifluoromethyl)benzyl)piperazine-1-yl)pentanoate;
(69) methyl 2-(4-fluorophenyl)-2-isopropyl-5-(4-(4-(trifluoromethyl)benzyl)piperazine-1-yl)pentanoate;
(70) methyl 2-(4-fluorophenyl)-2-isopropyl-5-(4-(2-methoxyphenyl)piperazine-1-yl)pentanoate;
(71) methyl 2-(4-fluorophenyl)-2-isopropyl-5-(4-(3-methoxyphenyl)piperazine-1-yl)pentanoate;
(72) methyl 2-(4-fluorophenyl)-2-isopropyl-5-(4-(4-methoxyphenyl)piperazine-1-yl)pentanoate;
(73) methyl 2-(4-fluorophenyl)-2-isopropyl-5-(4-(4-methoxybenzyl)piperazine-1-yl)pentanoate;
(74) methyl 2-(4-fluorophenyl)-2-isopropyl-5-(4-(2,3,4-trimethoxybenzyl)piperazine-1-yl)pentanoate;
(75) methyl 2-(4-fluorophenyl)-2-isopropyl-5-(4-(3-methylbenzyl)piperazine-1-yl)pentanoate;
(76) methyl 2-(4-fluorophenyl)-2-isopropyl-5-(4-(4-methylbenzyl)piperazine-1-yl)pentanoate;
(77) methyl 5-(4-(4-t-butylbenzyl)piperazine-1-yl)-2-(4-fluorophenyl)-2-isopropylpentanoate;
(78) methyl 5-(4-(3-chlorophenyl)piperazine-1-yl)-2-(4-fluorophenyl)-2-isopropylpentanoate;
(79) methyl 5-(4-(3-chlorobenzyl)piperazine-1-yl)-2-(4-fluorophenyl)-2-isopropylpentanoate;
(80) methyl 5-(4-(4-chlorobenzyl)piperazine-1-yl)-2-(4-fluorophenyl)-2-isopropylpentanoate;
(81) methyl 5-(4-(3,4-dichlorobenzyl)piperazine-1-yl)-2-(4-fluorophenyl)-2-isopropylpentanoate;
(82) methyl 2-(4-bromophenyl)-2-isopropyl-5-(4-(4-methoxybenzyl)piperidine-1-yl)pentanoate;
(83) methyl 2-(4-bromophenyl)-2-isopropyl-5-(4-(3-methoxybenzylidene)piperidine-1-yl)pentanoate;
(84) methyl 2-(4-bromophenyl)-2-isopropyl-5-(4-(3-methoxybenzyl)piperidine-1-yl)pentanoate;
(85) methyl 2-(4-bromophenyl)-2-isopropyl-5-(4-(4-methylbenzylidene)piperidine-1-yl)pentanoate;
(86) methyl 2-(4-bromophenyl)-2-isopropyl-5-(4-(4-methylbenzyl)piperidine-1-yl)pentanoate;
(87) methyl 2-(4-bromophenyl)-2-isopropyl-5-(4-(3-methylbenzylidene)piperidine-1-yl)pentanoate;
(88) methyl 2-(4-bromophenyl)-2-isopropyl-5-(4-(3-methylbenzyl)piperidine-1-yl)pentanoate;
(89) methyl 2-(4-bromophenyl)-2-isopropyl-5-(4-(2-methylbenzylidene)piperidine-1-yl)pentanoate;
(90) methyl 2-(4-bromophenyl)-2-isopropyl-5-(4-(2-methylbenzyl)piperidine-1-yl)pentanoate;
(91) methyl 2-(4-bromophenyl)-5-(4-(4-chlorobenzylidene)piperidine-1-yl)-2-isopropylpentanoate;
(92) methyl 2-(4-bromophenyl)-5-(4-(4-chlorobenzyl)piperidine-1-yl)-2-isopropylpentanoate;
(93) methyl 2-(4-bromophenyl)-5-(4-(3-chlorobenzylidene)piperidine-1-yl)-2-isopropylpentanoate;
(94) methyl 2-(4-bromophenyl)-5-(4-(3-chlorobenzyl)piperidine-1-yl)-2-isopropylpentanoate;
(95) methyl 2-(4-bromophenyl)-5-(4-(4-fluorobenzylidene)piperidine-1-yl)-2-isopropylpentanoate;
(96) methyl 2-(4-bromophenyl)-5-(4-(4-fluorobenzyl)piperidine-1-yl)-2-isopropylpentanoate;
(97) methyl 2-isopropyl-5-(4-(4-methoxybenzylidene)piperidine-1-yl)-2-(4-methoxyphenyl)pentanoate;
(98) methyl 2-isopropyl-5-(4-(4-methoxybenzyl)piperidine-1-yl)-2-(4-methoxyphenyl)pentanoate;
(99) methyl 2-isopropyl-5-(4-(3-methoxybenzylidene)piperidine-1-yl)-2-(4-methoxyphenyl)pentanoate;
(100) methyl 2-isopropyl-5-(4-(3-methoxybenzyl)piperidine-1-yl)-2-(4-methoxyphenyl)pentanoate;
(101) methyl 2-isopropyl-2-(4-methoxyphenyl)-5-(4-(4-methylbenzylidene)piperidine-1-yl)pentanoate;
(102) methyl 2-isopropyl-2-(4-methoxyphenyl)-5-(4-(4-methylbenzyl)piperidine-1-yl)pentanoate;
(103) methyl 2-isopropyl-2-(4-methoxyphenyl)-5-(4-(3-methylbenzylidene)piperidine-1-yl)pentanoate;

(104) methyl 2-isopropyl-2-(4-methoxyphenyl)-5-(4-(3-methylbenzyl)piperidine-1-yl)pentanoate;
(105) methyl 2-isopropyl-2-(4-methoxyphenyl)-5-(4-(2-methylbenzylidene)piperidine-1-yl)pentanoate;
(106) methyl 2-isopropyl-2-(4-methoxyphenyl)-5-(4-(2-methylbenzyl)piperidine-1-yl)pentanoate;
(107) methyl 5-(4-(4-chlorobenzylidene)piperidine-1-yl)-2-isopropyl-2-(4-methoxyphenyl)pentanoate;
(108) methyl 5-(4-(4-chlorobenzyl)piperidine-1-yl)-2-isopropyl-2-(4-methoxyphenyl)pentanoate;
(109) methyl 5-(4-(3-chlorobenzylidene)piperidine-1-yl)-2-isopropyl-2-(4-methoxyphenyl)pentanoate;
(110) methyl 5-(4-(3-chlorobenzyl)piperidine-1-yl)-2-isopropyl-2-(4-methoxyphenyl)pentanoate;
(111) methyl 5-(4-(4-fluorobenzylidene)piperidine-1-yl)-2-isopropyl-2-(4-methoxyphenyl)pentanoate; and
(112) methyl 5-(4-(4-fluorobenzyl)piperidine-1-yl)-2-isopropyl-2-(4-methoxyphenyl)pentanoate.

The phenylacetate derivatives of the present invention, represented by the Chemical Formula 1 may be used in the form of a pharmaceutically acceptable salt, and acid addition salts formed by pharmaceutically acceptable free acids are useful as salts. The acid addition salts may be obtained from inorganic acids, such as hydrochloric acid, nitric acid, phosphoric acid, sulfuric acid, hydrobromic acid, hydriodic acid, nitrous acid or phosphorous acid and non-toxic organic acids, such as aliphatic mono- and dicarboxylates, phenyl-substituted alkanoate, hydroxyl alkanoate and alkanedioate, aromatic acids, and non-toxic organic acids, such as aliphatic and aromatic sulfonic acids. These pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate or mandelate.

The acid addition salts according to the present invention may be prepared by conventional methods, for example by dissolving derivatives of the Chemical Formula 1 in excess of an acid addition salt and precipitating the resulting salts in an water-miscible organic solvent, for example, methanol, ethanol, acetone or acetonitrile.

After the solvent from the mixture or acid in excess is evaporated, the salts may be prepared by drying the precipitated salts or filtration under vacuum.

Pharmaceutically acceptable salts may also be prepared using bases. Alkali metals or alkali earth metals may be obtained, for example by dissolving the compound in excess of an alkali metal hydroxide or an alkali earth metal hydroxide solution, filtrating the non-soluble compound salts, evaporating the filtrate, and drying it. Then, suitable pharmaceutically acceptable salts include sodium, potassium or calcium salts. In addition, the corresponding salts are obtained by reacting alkali metals or alkali earth metals with a suitable silver salt (ex., silver nitrate).

The phenylacetate derivatives represented by the Chemical Formula 1 include pharmaceutically acceptable salts, all the salts prepared by conventional methods, hydrates and solvates.

The acid addition salts may be synthesized by conventional methods, for example by dissolving the compound of the Chemical Formula 1 in a water-miscible solvent, for example, acetone, methanol, ethanol, or acetonitrile, adding an organic acid in excess or an acid-water solution of inorganic acids, and then precipitating or crystallizing it. After the solvent from the mixture or acid in excess is evaporated, the acid addition salts may be obtained or the precipitated salts may be prepared from the filtrate evaporated under vacuum.

As described in the following Reaction Formula 1, the present invention provides a preparation method of phenylacetate derivatives, including:

Preparing an ester compound of Chemical Formula 3 by esterification reaction of a carboxyl acid compound of Chemical Formula 2 as a starting material under an acid catalyst (Step 1);

Preparing a compound of Chemical Formula 4 by reacting the compound of Chemical Formula 3 obtained from step 1 with t-butoxide and isopropyl bromide (Step 2);

Preparing a compound of Chemical Formula 5 by reacting the compound of Chemical Formula 4 obtained from step 2 with 1,3-dibromopropane (Step 3); and Preparing the compound of Chemical Formula 1 by reacting the compound of Chemical Formula 5 obtained from step 3 with a compound of Chemical Formula 6 or Chemical Formula 7 (Step 4).

[Reaction Formula 1]

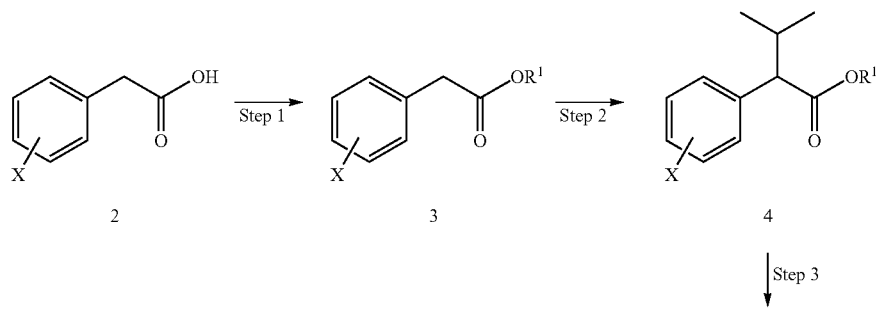

-continued

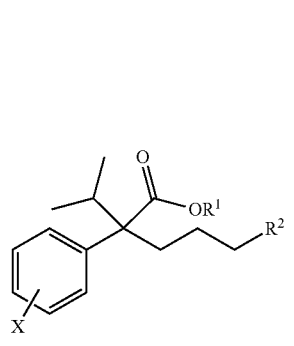

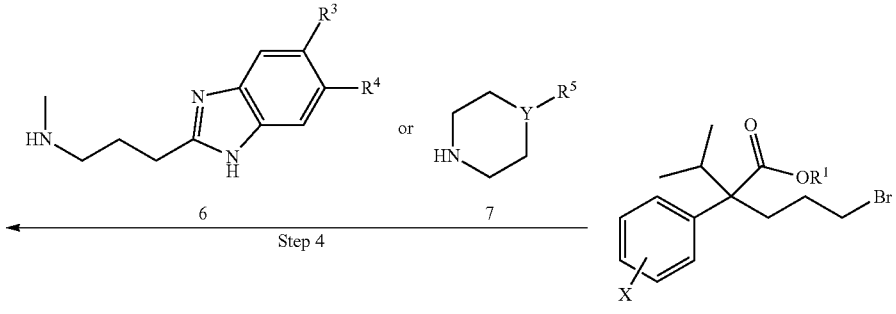

Step 4

(Where, $R^1$, $R^2$, $R^3$, $R^4$, $R^5$, X, and Y are as defined in the Chemical Formula 1).

Hereinafter, the preparation method according to the present invention will be described step-by-step.

Step 1

The Step 1 according to the present invention is a step of preparing an ester compound of Chemical Formula 3 by esterification reaction of a carboxyl acid compound of Chemical Formula 2 as a starting material under an acid catalyst.

The compound of Chemical Formula 2 as a starting material is commercially available or obtained by a synthesis method known in the art.

The reaction in the Step 1 is commonly known in the organic chemistry art, and the reaction conditions such as reaction solvents, reaction temperature, and reaction times may be suitably selected, considering reactants and products. For example, methanol was used as a reaction solvent, and the compound of the Chemical Formula 3 was obtained by heating or refluxing the mixture at 85~95° C. under an acid catalyst, especially in the presence of sulfuric acid for 2~4 hours.

Step 2

The Step 2 according to the present invention is a step of preparing a compound of Chemical Formula 4 by reacting the compound of Chemical Formula 3 in the step 1 with t-butoxide and isopropyl bromide.

Specifically, a compound of Chemical Formula 4 may be obtained by dissolving the compound of Chemical Formula 3 and t-butoxide in anhydrous dimethylformamide as a reaction solvent, adding isopropyl bromide into the mixture, and stirring the mixture at room temperature for 2~4 hours.

Step 3

The Step 3 according to the present invention is a step of preparing a compound of Chemical Formula 5 by reacting the compound of Chemical Formula 4 in the step 2 with 1,3-dibromopropane.

Anhydrous tetrahydrofuran may be used as a reaction solvent.

Specifically, amines such as diisopropylamine, and a solution of n-butyllithium in hexane are added into the reaction solvent at low temperatures of −75~−80° C. A compound of Chemical Formula 5 may be obtained by adding and stirring the compound of Chemical Formula 4, dropping 1,3-dibromopropane into the solution, and stirring it at room temperature overnight.

Step 4

The Step 4 according to the present invention is a step of preparing the compound of Chemical Formula 1 by reacting the compound of Chemical Formula 5 in the step 3 with the compound of Chemical Formula 6 or Chemical Formula 7.

When the compound of Chemical Formula 5 is reacted with benzimidazole derivatives, the compound of Chemical Formula 1 may be obtained by dissolving the compound of Chemical Formula 5 into methanol, adding variously substituted benzimidazole derivatives and potassium carbonate, and heating or refluxing the mixture at 85~95° C. for 2~4 hours.

When the compound of Chemical Formula 5 is reacted with piperazine or piperidine derivatives, the compound of Chemical Formula 1 may be obtained by dissolving the compound of Chemical Formula 5 in acetonitrile, adding variously substituted piperazine or piperidine derivatives, triethylamine, and sodium iodate, and heating or refluxing the mixture at 85~95° C. for 2~4 hours.

Furthermore, the present invention provides compounds represented by the following Chemical Formula 3, Chemical Formula 4, or Chemical Formula 5 produced as intermediates when the phenylacetate derivatives are prepared.

[Chemical Formula 3]

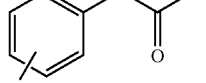

[Chemical Formula 4]

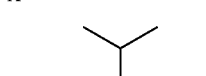

[Chemical Formula 5]

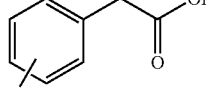

In the chemical formulas 3~5, X and $R^1$ are as defined in the Chemical Formula 1.

After the phenylacetate derivatives or intermediates are prepared above by the present invention, their molecular structures may be identified by IR, NMR, mass spectroscopy, liquid chromatography, X-ray crystallography, and comparison of the actual element analysis values with the calculated values.

Furthermore, the present invention provides a composition for prevention or treatment of diseases induced by the activation of T-type calcium ion channels, containing the phenylacetate derivatives or pharmaceutically acceptable salts thereof as an active ingredient.

The T-type calcium ion channel is found in central muscles, endocrine glands in the adrenal, sinoatrial node, and heart. A T-type calcium ion channel antagonist is known to have therapeutic effect on brain diseases, such as epilepsy and hypertension cardiac diseases, such as encephalopathy and angina pectoris [Hosravani, Houman et al., "Effects of Cav3.2 channel mutations linked to idiopathic generalized epilepsy", *Annals of Neurology* (2005), 57(5), 745-749; Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855]. A recent study reported that a T-type calcium ion channel antagonist has an activity in treatment of chronic pain [*Drugs of the Future* (2005), 40, 573-580]. For example, Mibefradil and Ethosuximide, as T-type calcium ion channel antagonists, showed dosage-dependent reversed mechanic and thermal induction in a spinal nerve ligation animal model, thus ascertaining that the T-type calcium ion channel antagonists have a therapeutic effect on neurogenic pains [Barton, Matthew E. et al., "The antihyperalgesic effects of the T-type calcium channel blockers ethosuximide, trimethadione, and mibefradil", *European Journal of Pharmacology* (2005), 521(1-3), 79-85].

Calcium plays an important role as an intracellular messenger and regulates a variety of cellular processes. Calcium is known to be involved in cell growth among the cellular processes, and it is expected that a T-type calcium ion channel antagonist may have an anticancer activity [Nat. Rev. Mol. Cell Biol. 2003, 4, 517-529].

It is shown that the phenylacetate derivatives and pharmaceutically acceptable salts thereof as an active ingredient in the composition according to the present invention significantly inhibit the streams of calcium ions in the T-type calcium ion channels of HEK293 cells (See Experimental Example 1 and Table 2). Thus, the composition according to the present invention effectively inhibits the activation of T-type calcium ion channels and may be useful in the prevention or treatment of diseases, such as hypertension, cancer, epilepsy, and neurogenic pains induced by the activation of T-type calcium ion channels.

In addition, the present invention provides the use of the phenylacetate derivatives of Chemical Formula 1 used in the manufacture of drugs for prevention and treatment of diseases, such as hypertension, cancer, epilepsy, and neurogenic pains induced by the activation of T-type calcium ion channels, or pharmaceutically acceptable salts thereof.

Furthermore, the present invention provides a method for treatment of diseases, such as hypertension, cancer, epilepsy, and neurogenic pains induced by the activation of T-type calcium ion channels, including administering a pharmaceutically effective amount of the phenylacetate derivatives of Chemical Formula 1 or pharmaceutically acceptable salts thereof to mammals or patients in need. The mammals include humans.

When the composition of the present invention is used as a medicine, a pharmaceutical composition containing the phenylacetate derivatives represented by Chemical Formula 1, or pharmaceutically acceptable salts thereof as an active ingredient may be prepared in the forms of, but not limited to, various oral or parenteral administrations and administered.

Formulations for oral administration include, for example, tablets, pills, soft/hard capsules, solutions, suspensions, emulsions, syrups, granules, and elixirs. These formulations contain a diluent (ex., lactose, dextrose, sucrose, mannitol, sorbitol, cellulose and/or glycine) and a lubricant (ex., silica, talc, stearic acid and magnesium or calcium salts thereof, and/or polyethylene glycol) as well as an active ingredient. The tablets may also contain a binding agent, such as magnesium aluminum silicate, starch paste, gelatin, methylcellulose, sodium carboxymethylcellulose, and/or polyvinylpyrrolidine. In some cases, they may contain a disintegrating agent such as starch, agar, alginic acid, or sodium salt thereof, or boiling mixture and/or an absorbent, a colorant, a flavoring agent, and a sweetening agent.

A pharmaceutical composition of the derivatives represented by Chemical Formula 1 as an active ingredient may be parenterally administered. The parenteral administration includes injection methods such as subcutaneous, intravenous or intramuscular injection, or intrapleural injection.

To prepare a formulation for parenteral administration, the phenylacetate derivatives of Chemical Formula 1 or pharmaceutically acceptable salts thereof may be mixed with a stabilizer or a buffer in water, and prepared in an ampoule or a vial unit dosage form. The composition may be sterilized and/or contain expedients such as preservatives, stabilizers, wetting agents, or emulsifiers, salts for osmotic pressure and/or buffers, and other therapeutically useful materials. It may be prepared by conventional methods, such as mixing, granulation, or coating method.

The dosage of the compound of the present invention may depend on the age, body weight, and sex of a patient, the dosage form, and the severity of the disease. For a 70 kg adult patient, the dosage is generally 0.1~1,000 mg/day, preferably 1~500 mg/day, and may be administered once a day to several times a day at a constant time interval at the discretion of the doctor or pharmacist.

DESCRIPTION OF THE PREFERRED EMBODIMENTS

Hereinafter, the present invention will be described by Embodiments and Experimental Examples. However, the following embodiments are given to illustrate the present invention, are not to be construed as being limiting.

Embodiment 1

Preparation of 5-{[3-(1H-benzimidazole-2-yl)propyl]methylamino}-2-(4-bromophenyl)-2-isopropyl-pentanoic acid methyl ester Step 1: Preparation of (4-bromophenyl)acetic acid methyl ester (4-bromophenyl)acetic acid (10 g, 1 eq) was dissolved in methanol. 10 ml conc. $H_2SO_4$ was added into the solution and the mixture was heated and refluxed for 3 hours. When the reaction was completed, the mixture was vacuum distilled and extracted with ethyl acetate and water. After the organic layer was washed with saturated $NaHCO_3$, the target compound (4-bromophenyl)acetic acid methyl ester was obtained by drying the layer with anhydrous magnesium sulfate and removing the solvent at low pressures (9.87 g, 93%).

¹H NMR (400 MHz, CDCl₃) δ 7.45 (d, J=8.4 Hz, 2H), 7.16 (d, J=8.4 Hz, 2H) 3.70 (s, 3H), 3.59 (s, 2H)

Step 2: Preparation of
2-(4-bromophenyl)-3-methylbutyric acid methyl ester

The (4-bromophenyl)acetic acid methyl ester in the Step 1 and potassium t-butoxide (4.8 g, 1 eq) were dissolved in 200 ml DMF at 0° C. Isopropyl bromide (4 ml. 1 eq) was added into the mixture and stirred at room temperature for 3 hours. When the reaction was completed, the mixture was extracted 3 times with ethyl acetate and water, and washed with saline solution. After the organic layer was dried with anhydrous and the solvent was removed at low pressures, the target compound 2-(4-bromophenyl)3-methylbutyric acid methyl ester was obtained by separation and purification of the mixture using a column chromatography (ethyl acetate:n-hexane=1:10) (6.60 g, 57%).

1H NMR (400 MHz, CDCl3) δ 7.42 (d, J=8.3 Hz, 2H), 7.20 (d, J=8.4 Hz, 2H), 3.64 (s, 3H), 3.11 (d, J=10.5 Hz, 1H), 2.31-2.25 (m, 1H), 1.01 (d, J=6.5 Hz, 3H), 0.69 (d, J=6.7 Hz, 3H)

Step 3: Preparation of
5-bromo-2-(4-bromophenyl)-2-isopropylpentanoic acid methyl ester Diisopropylamine (5.04 ml, 1.5 eq) in anhydrous THF at −78° C. and n-butyllithium in hexane were mixed and dissolved into 2.5 M of solution (10.55 ml, 1.1 eq). The 2-(4-bromophenyl)-methylbutyric acid methyl ester (6.5 g, 1 eq) in the Step 2 was added into the solution and stirred. After 30 minutes, 1,3-dibromopropane (7.31 ml, 3 eq) was dissolved in anhydrous THF. The mixture was dropped into the solution and stirred at room temperature overnight. When the reaction was completed, the compound was extracted with diethylether and water, washed with 1N HCl and saturated NaHCO₃. The organic layer was dried with anhydrous magnesium sulfate and the solvent was removed at low pressures. Subsequently, the target compound 5-bromo-2-(4-bromophenyl)-2-isopropylpentanoic methyl ester was obtained by separation and purification of the mixture using a column chromatography (ethyl acetate:n-hexane=1:100) (5.98 g, 44%).

1H NMR (400 MHz, CDCl3) δ 7.46 (d, J=8.7 Hz, 2H), 7.08 (d, J=8.7 Hz, 2H), 3.74 (s, 3H), 3.38-3.30 (m, 2H), 2.43-2.38 (m, 1H), 2.22-2.15 (m, 1H), 2.10-2.03 (m, 1H), 1.73-1.69 (m, 1H), 1.60-1.53 (m, 1H), 0.89 (d, J=6.7 Hz, 3H), 0.80 (d, J=6.8 Hz, 3H)

Step 4: Preparation of 5-{[3-(1H-benzimidazole-2-yl)propyl]methylamino}-2-(4-bromophenyl)-2-isopropylpentanoic acid methyl ester After the 5-bromo-2-(4-bromophenyl)-2-isopropylpentanoic acid methyl ester (1 g, 1 eq) was dissolved in ethanol, [3-(1H-benzimidazole-2-yl)propyl]methylamine (0.66 g, 1 eq) as a benzimidazole derivative, and potassium carbonate (0.58 g, 1.2 eq) were added into the solution and heated and refluxed for 3 hours. When the reaction was completed, the precipitate was filtrated and the solvent was removed at low pressures. The target compound 5-{[3-(1H-benzimidazole-2-yl)propyl]methylamino}-2-(4-bromophenyl)-2-isopropyl pentanoic acid methyl ester was obtained by separation and purification of the mixture using a column chromatography (ethyl acetate:methanol=10:1) (635 mg, 36%).

1H NMR (400 MHz, CDCl3) δ 7.45 (bs, 2H), 7.39 (d, J=8.6 Hz, 2H), 7.18 (dd, J=6.0, 3.1 Hz, 2H), 7.10 (d, J=8.6 Hz, 2H), 3.69 (s, 3H), 3.04 (t, J=6.4 Hz, 2H), 2.48 (t, J=5.8 Hz, 2H), 2.40-2.35 (m, 3H), 2.21 (s, 3H), 2.10-2.04 (m, 1H), 1.98-1.89 (m, 3H), 1.43-1.23 (m, 2H), 0.85 (d, J=6.8 Hz, 3H), 0.74 (d, J=6.8 Hz, 3H)

Embodiment 2

Preparation of 2-(4-bromophenyl)-2-isopropyl-5-(4-phenylpiperazine-1-yl)pentanoic acid methyl ester Step 1~3: Preparation of
5-bromo-2-(4-bromophenyl)-2-isopropylpentanoic acid methyl ester The target compound was obtained by repeating the same process as in the Steps 1~3 of Embodiment 1.

Step 4: Preparation of 2-(bromophenyl)-2-isopropyl-5-(4-phenylpiperazine-1-yl)pentanoic acid methyl ester After the 5-bromo-2-(4-bromophenyl)-2-isopropylpentanoic acid methyl ester (200 mg, 1 eq) was dissolved in acetonitrile, 4-phenylpiperazine (70 mg, 1 eq) as a piperazine derivative, Et₃N (0.06 ml, 1.2 eq), and sodium iodate were added into the solution and heated and refluxed for 3 hours. When the reaction was completed, the precipitate was filtrated and the mixture was vacuum distilled and extracted with ethyl acetate and water. After the organic layer was washed with 1N HCl and saturated NaHCO₃, the target compound 2-(4-bromophenyl)-2-isopropyl-5-(4-phenylpiperazine-1-yl)pentanoic acid methyl ester was obtained by drying the mixture with anhydrous sodium sulfate and removing the solvent at low pressures (69 mg, 42%).

1H NMR (400 MHz, CDCl3) δ 12.92 (s, 1H), 7.45-7.40 (m, 5H), 7.27-7.25 (m, 1H), 7.07-7.00 (m, 2H). 4.28 (s, 2H), 3.76 (s, 3H), 3.59-3.56 (m, 4H), 3.48-3.45 (m, 1H), 3.02 (s, 2H), 2.41-2.25 (m, 2H), 1.91-1.76 (m, 2H), 1.46-1.24 (m, 2H), 0.91 (d, J=6.5 Hz, 3H), 0.80 (d, J=6.6 Hz, 3H)

Embodiment 3

Preparation of 2-(4-bromophenyl)-2-isopropyl-5-[4-(4-methoxybenzylidene)piperidine-1-yl]pentanoic acid methyl ester Except that 4-(4-methoxybenzylidene)piperidine (122 mg, 1 eq) as a piperidine derivative instead of a piperazine derivative in the Step 4 was used, the target compound 2-(4-bromophenyl)-2-isopropyl-5-[4-(4-methoxybenzylidene)piperidine-1-yl]pentanoic acid methyl ester was obtained by carrying out the same processes as in the Embodiment 2 (212 mg, 81%).

1H NMR (400 MHz, CDCl3) δ 7.42 (d, J=8.5 Hz, 2H), 7.11 (d, J=8.7 Hz, 2H), 7.06 (d, J=8.6 Hz, 2H), 6.84 (d, J=8.7 Hz, 2H), 6.20 (s, 1H), 3.80 (s, 3H), 3.72 (s, 3H), 2.43-2.36 (m, 5H), 2.35-2.27 (m, 5H), 2.02-1.96 (m, 3H), 1.27 (m, 1H), 0.85 (d, J=6.7 Hz, 3H), 0.75 (d, J=6.8 Hz, 3H)

Embodiment 4

Preparation of methyl 5-((3-(1H-benzo[d]imidazole-2-yl)propyl)(methyl))amino)-2-isopropyl-2-(4-methoxyphenyl)pentanoate Except that (4-methoxyphenyl)acetic acid instead of (4-bromophenyl)acetic acid was used in the Step 1 and (3-

(1H-benzo[d]imidazole-2-yl)propyl)methylamine was used as a benzimidazole derivative in the Step 4, the target compound was obtained by carrying out the same processes as in the Embodiment 1 (146 mg, 37%).

Embodiment 5

Preparation of methyl 2-isopropyl-5-((3-(5-methoxy-1H-benzo[d]imidazole-2-yl)propyl)(methyl))amino)-2-(4-methoxyphenyl)pentanoate Except that (4-methoxyphenyl)acetic acid instead of (4-bromophenyl)acetic acid was used in the Step 1 and (3-(5-methoxy-1H-benzo[d]imidazole-2-yl)propyl)methylamine was used as a benzimidazole derivative in the Step 4, the target compound was obtained by carrying out the same processes as in the Embodiment 1 (118 mg, 43%).

Embodiment 6

Preparation of methyl 5-((3-(5,6-dimethyl-1H-benzo[d]imidazole-2-yl)propyl)(methyl))amino)-2-isopropyl-2-(4-methoxyphenyl)pentanoate Except that (4-methoxyphenyl)acetic acid instead of (4-bromophenyl)acetic acid was used in the Step 1 and (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (158 mg, 38%).

Embodiment 7

Preparation of methyl 5-((3-(1H-benzo[d]imidazole-2-yl)propyl)(methyl))amino)-2-(3,4-dimethoxyphenyl)-2-isopropylpentanoate Except that (3,4-dimethoxyphenyl)acetic acid instead of (4-bromophenyl)acetic acid was used in the Step 1 and (3-(1H-benzo[d]imidazole-2-yl)propyl)methylamine was used as a benzimidazole derivative in the Step 4, the target compound was obtained by carrying out the same processes as in the Embodiment 1 (508 mg, 37%).

Embodiment 8

Preparation of methyl 2-(3,4-dimethoxyphenyl)-2-isopropyl-5-((3-(5-methoxy-1H-benzo[d]imidazole-2-yl)propyl)(methyl))amino)pentanoate Except that (3,4-dimethoxyphenyl)acetic acid instead of (4-bromophenyl)acetic acid was used in the Step 1 and (3-(5-methoxy-1H-benzo[d]imidazole-2-yl)propyl)methylamine was used as a benzimidazole derivative in the Step 4, the target compound was obtained by carrying out the same processes as in the Embodiment 1 (179 mg, 43%).

Embodiment 9

Preparation of methyl 2-(3,4-dimethoxyphenyl)-5-((3-(5,6-dimethyl-1H-benzo[d]imidazole-2-yl)propyl)(methyl))amino)-2-isopropylpentanoate Except that (3,4-dimethoxyphenyl)acetic acid instead of (4-bromophenyl)acetic acid was used in the Step 1 and (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (63 mg, 46%).

Embodiment 10

Preparation of ethyl 5-((3-(1H-benzo[d]imidazole-2-yl)propyl)(methyl))amino)-2-isopropyl-2-phenylpentanoate Except that phenylacetic acid instead of (4-bromophenyl)acetic acid was used in the Step 1 and (3-(1H-benzo[d]imidazole-2-yl)propyl)methylamine was used as a benzimidazole derivative in the Step 4, the target compound was obtained by carrying out the same processes as in the Embodiment 1 (35 mg, 20%).

Embodiment 11

Preparation of ethyl 5-((3-(5,6-dimethyl-1H-benzo[d]imidazole-2-yl)propyl)(methyl))amino)-2-isopropyl-2-phenylpentanoate Except that phenylacetic acid instead of (4-bromophenyl)acetic acid was used in the Step 1 and (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (208 mg, 49%).

Embodiment 12

Preparation of methyl 2-(4-bromophenyl)-5-((3-(5,6-dimethyl-1H-benzo[d]imidazole-2-yl)propyl)(methyl))amino)-2-isopropylpentanoate Except that (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (112 mg, 22%).

Embodiment 13

Preparation of methyl 2-(4-bromophenyl)-2-isopropyl-5-((3-(5-methoxy-1H-benzo[d]imidazole-2-yl)propyl)(methyl))amino)pentanoate Except that (3-(5-methoxy-1H-benzo[d]imidazole-2-yl)propyl)methylamine was used as a benzimidazole derivative in the Step 4, the target compound was obtained by carrying out the same processes as in the Embodiment 1 (127 mg, 23%).

Embodiment 14

Preparation of methyl 5-((3-(1H-benzo[d]imidazole-2-yl)propyl)(methyl))amino)-2-(3-bromophenyl)-2-isopropylpentanoate Except that (3-bromophenyl)acetic acid instead of (4-bromophenyl)acetic acid was used in the Step 1 and (3-(1H-benzo[d]imidazole-2-yl)propyl)methylamine was used as a benzimidazole derivative in the Step 4, the target compound was obtained by carrying out the same processes as in the Embodiment 1 (70 mg, 54%).

Embodiment 15

Preparation of methyl 2-(3-bromophenyl)-2-isopropyl-5-((3-(5-methoxy-1H-benzo[d]imidazole-2-yl)propyl)(methyl))amino)pentanoate Except that (3-bromophenyl)acetic acid instead of (4-bromophenyl)acetic acid was used in the Step 1 and (3-(5-methoxy-1H-benzo[d]imidazole-2-yl)propyl)methylamine was used as a benzimidazole derivative in the Step 4, the target compound was obtained by carrying out the same processes as in the Embodiment 1 (115 mg, 83%).

Embodiment 16

Preparation of methyl 2-(3-bromophenyl)-5-((3-(5,6-dimethyl-1H-benzo[d]imidazole-2-yl)propyl)(methyl))amino)-2-isopropylpentanoate Except that (3-bromophenyl)acetic acid instead of (4-bromophenyl)acetic acid was used in the Step 1 and (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (65 mg, 47%).

Embodiment 17

Preparation of methyl 5-((3-(1H-benzo[d]imidazole-2-yl)propyl)(methyl))amino)-2-(4-fluorophenyl)-2-isopropylpentanoate Except that (4-fluorophenyl)acetic acid instead of (4-bromophenyl)acetic acid was used in the Step 1 and (3-(1H-benzo[d]imidazole-2-yl)propyl)methylamine was used as a benzimidazole derivative in the Step 4, the target compound was obtained by carrying out the same processes as in the Embodiment 1 (76 mg, 27%).

Embodiment 18

Preparation of methyl 2-(4-fluorophenyl)-2-isopropyl-5-((3-(5-methoxy-1H-benzo[d]imidazole-2-yl)propyl)(methyl))amino)pentanoate Except that (4-fluorophenyl)acetic acid instead of (4-bromophenyl)acetic acid was used in the Step 1 and (3-(5-methoxy-1H-benzo[d]imidazole-2-yl)propyl)methylamine was used as a benzimidazole derivative in the Step 4, the target compound was obtained by carrying out the same processes as in the Embodiment 1 (133 mg, 46%).

Embodiment 19

Preparation of methyl 5-((3-(5,6-dimethyl-1H-benzo[d]imidazole-2-yl)propyl)(methyl))amino)-2-(4-fluorophenyl)-2-isopropylpentanoate Except that (4-fluorophenyl)acetic acid instead of (4-bromophenyl)acetic acid was used in the Step 1 and (3-(5,6-dimethyl-1H-benzo[d]imidazole-2-yl)propyl)methylamine was used as a benzimidazole derivative in the Step 4, the target compound was obtained by carrying out the same processes as in the Embodiment 1 (118 mg, 42%).

Embodiment 20

Preparation of ethyl 2-isopropyl-5-(4-(2-methoxyphenyl)piperazine-1-yl)-2-phenylpentanoate Except that phenylacetic acid instead of (4-bromophenyl)acetic acid was used in the Step 1 and (2-methoxyphenyl)piperazine was used as a piperazine derivative in the Step 4, the target compound was obtained by carrying out the same processes as in the Embodiment 2 (78 mg, 57%).

Embodiment 21

Preparation of ethyl 2-isopropyl-5-(4-(3-methoxyphenyl)piperazine-1-yl)-2-phenylpentanoate Except that phenylacetic acid instead of (4-bromophenyl)acetic acid was used in the Step 1 and (3-methoxyphenyl)piperazine was used as a piperazine derivative in the Step 4, the target compound was obtained by carrying out the same processes as in the Embodiment 2 (84 mg, 61%).

Embodiment 22

Preparation of ethyl 2-isopropyl-5-(4-(4-methoxyphenyl)piperazine-1-yl)-2-phenylpentanoate Except that phenylacetic acid instead of (4-bromophenyl)acetic acid was used in the Step 1 and (4-methoxyphenyl)piperazine was used as a piperazine derivative in the Step 4, the target compound was obtained by carrying out the same processes as in the Embodiment 2 (75 mg, 56%).

Embodiment 23

Preparation of ethyl 2-isopropyl-5-(4-(4-methoxybenzyl)piperazine-1-yl)-2-phenylpentanoate Except that phenylacetic acid instead of (4-bromophenyl)acetic acid was used in the Step 1 and (4-methoxybenzyl)piperazine was used as a piperazine derivative in the Step 4, the target compound was obtained by carrying out the same processes as in the Embodiment 2 (38 mg, 53%).

Embodiment 24

Preparation of ethyl 5-(4-(2-fluorophenyl)piperazine-1-yl)-2-isopropyl-2-phenylpentanoate Except that phenylacetic acid instead of (4-bromophenyl)acetic acid was used in the Step 1 and (2-fluorophenyl)piperazine was used as a piperazine derivative in the Step 4, the target compound was obtained by carrying out the same processes as in the Embodiment 2 (75 mg, 57%).

Embodiment 25

Preparation of ethyl 5-(4-(4-fluorophenyl)piperazine-1-yl)-2-isopropyl-2-phenylpentanoate Except that phenylacetic acid instead of (4-bromophenyl)acetic acid was used in the Step 1 and (4-fluorophenyl)piperazine was used as a piperazine derivative in the Step 4, the target compound was obtained by carrying out the same processes as in the Embodiment 2 (71 mg, 54%).

Embodiment 26

Preparation of ethyl 5-(4-(4-fluorobenzyl)piperazine-1-yl)-2-isopropyl-2-phenylpentanoate Except that phenylacetic acid instead of (4-bromophenyl) acetic acid was used in the Step 1 and (4-fluorobenzyl)piperazine was used as a piperazine derivative in the Step 4, the target compound was obtained by carrying out the same processes as in the Embodiment 2 (54 mg, 40%).

Embodiment 27

Preparation of methyl 5-(4-benzhydrylpiperazine-1-yl)-2-(4-bromophenyl)-2-isopropylpentanoate Except that benzhydrylpiperazine was used as a piperazine derivative in the Step 4, the target compound was obtained by carrying out the same processes as in the Embodiment 2 (114 mg, 58%).

Embodiment 28

Preparation of methyl 2-(4-bromophenyl)-5-(4-(2-fluorophenyl)piperazine-1-yl)-2-isopropylpentanoate Except that (2-fluorophenyl)piperazine was used as a piperazine derivative in the Step 4, the target compound was obtained by carrying out the same processes as in the Embodiment 2 (45 mg, 26%).

Embodiment 29

Preparation of methyl 2-(4-bromophenyl)-5-(4-(4-fluorophenyl)piperazine-1-yl)-2-isopropylpentanoate Except that (4-fluorophenyl)piperazine was used as a piperazine derivative in the Step 4, the target compound was obtained by carrying out the same processes as in the Embodiment 2 (27 mg, 6%).

Embodiment 30

Preparation of methyl 2-(4-bromophenyl)-5-(4-(2-fluorobenzyl)piperazine-1-yl)-2-isopropylpentanoate Except that (2-fluorobenzyl)piperazine was used as a piperazine derivative in the Step 4, the target compound was obtained by carrying out the same processes as in the Embodiment 2 (103 mg, 58%).

Embodiment 31

Preparation of methyl 2-(4-bromophenyl)-5-(4-(3-fluorobenzyl)piperazine-1-yl)-2-isopropylpentanoate Except that (3-fluorobenzyl)piperazine was used as a piperazine derivative in the Step 4, the target compound was obtained by carrying out the same processes as in the Embodiment 2 (103 mg, 59%).

Embodiment 32

Preparation of methyl 2-(4-bromophenyl)-5-(4-(4-fluorobenzyl)piperazine-1-yl)-2-isopropylpentanoate Except that (4-fluorobenzyl)piperazine was used as a piperazine derivative in the Step 4, the target compound was obtained by carrying out the same processes as in the Embodiment 2 (101 mg, 57%).

Embodiment 33

Preparation of methyl 2-(4-bromophenyl)-2-isopropyl-5-(4-(3-(trifluoromethyl)benzyl)piperazine-1-yl)pentanoate Except that (3-(trifluoromethyl)benzyl)piperazine was used as a piperazine derivative in the Step 4, the target compound was obtained by carrying out the same processes as in the Embodiment 2 (124 mg, 65%).

Embodiment 34

Preparation of methyl 2-(4-bromophenyl)-2-isopropyl-5-(4-(4-(trifluoromethyl)benzyl)piperazine-1-yl)pentanoate Except that (4-(trifluoromethyl)benzyl)piperazine was used as a piperazine derivative in the Step 4, the target compound was obtained by carrying out the same processes as in the Embodiment 2 (97 mg, 51%).

Embodiment 35

Preparation of methyl 2-(4-bromophenyl)-2-isopropyl-5-(4-(2-methoxyphenyl)piperazine-1-yl)pentanoate Except that (2-methoxyphenyl)piperazine was used as a piperazine derivative in the Step 4, the target compound was obtained by carrying out the same processes as in the Embodiment 2 (83 mg, 47%).

Embodiment 36

Preparation of methyl 2-(4-bromophenyl)-2-isopropyl-5-(4-(3-methoxyphenyl)piperazine-1-yl)pentanoate Except that (3-methoxyphenyl)piperazine was used as a piperazine derivative in the Step 4, the target compound was obtained by carrying out the same processes as in the Embodiment 2 (55 mg, 31%).

Embodiment 37

Preparation of methyl 2-(4-bromophenyl)-2-isopropyl-5-(4-(4-methoxyphenyl)piperazine-1-yl)pentanoate Except that (4-methoxyphenyl)piperazine was used as a piperazine derivative in the Step 4, the target compound was obtained by carrying out the same processes as in the Embodiment 2 (55 mg, 31%).

Embodiment 38

Preparation of methyl 2-(4-bromophenyl)-2-isopropyl-5-(4-(4-methoxybenzyl)piperazine-1-yl)pentanoate Except that (4-methoxybenzyl)piperazine was used as a piperazine derivative in the Step 4, the target compound was obtained by carrying out the same processes as in the Embodiment 2 (93 mg, 52%).

Embodiment 39

Preparation of methyl 2-(4-bromophenyl)-2-isopropyl-5-(4-(2,3,4-trimethoxybenzyl)piperazine-1-yl) pentanoate Except that (2,3,4-trimethoxybenzyl)piperazine was used as a piperazine derivative in the Step 4, the target compound was obtained by carrying out the same processes as in the Embodiment 2 (121 mg, 60%).

Embodiment 40

Preparation of methyl 2-(4-bromophenyl)-2-isopropyl-5-(4-(3-methylbenzyl)piperazine-1-yl)pentanoate Except that (3-methylbenzyl)piperazine was used as a piperazine derivative in the Step 4, the target compound was obtained by carrying out the same processes as in the Embodiment 2 (112 mg, 64%).

Embodiment 41

Preparation of methyl 2-(4-bromophenyl)-2-isopropyl-5-(4-(4-methylbenzyl)piperazine-1-yl)pentanoate Except that (4-methylbenzyl)piperazine was used as a piperazine derivative in the Step 4, the target compound was obtained by carrying out the same processes as in the Embodiment 2 (107 mg, 61%).

Embodiment 42

Preparation of methyl 2-(4-bromophenyl)-5-(4-(4-t-butylbenzyl)piperazine-1-yl)-2-isopropylpentanoate Except that (4-t-butylbenzyl)piperazine was used as a piperazine derivative in the Step 4, the target compound was obtained by carrying out the same processes as in the Embodiment 2 (80 mg, 42%).

Embodiment 43

Preparation of methyl 2-(4-bromophenyl)-5-(4-(3-chlorophenyl)piperazine-1-yl)-2-isopropylpentanoate Except that (3-chlorophenyl)piperazine was used as a piperazine derivative in the Step 4, the target compound was obtained by carrying out the same processes as in the Embodiment 2 (60 mg, 34%).

Embodiment 44

Preparation of methyl 2-(4-bromophenyl)-5-(4-(3-chlorobenzyl)piperazine-1-yl)-2-isopropylpentanoate Except that (3-chlorobenzyl)piperazine was used as a piperazine derivative in the Step 4, the target compound was obtained by carrying out the same processes as in the Embodiment 2 (112 mg, 69%).

Embodiment 45

Preparation of methyl 2-(4-bromophenyl)-5-(4-(4-chlorobenzyl)piperazine-1-yl)-2-isopropylpentanoate Except that (4-chlorobenzyl)piperazine was used as a piperazine derivative in the Step 4, the target compound was obtained by carrying out the same processes as in the Embodiment 2 (111 mg, 63%).

Embodiment 46

Preparation of methyl 2-(4-bromophenyl)-5-(4-(3,4-dichlorobenzyl)piperazine-1-yl)-2-isopropylpentanoate Except that (3,4-dichlorobenzyl)piperazine was used as a piperazine derivative in the Step 4, the target compound was obtained by carrying out the same processes as in the Embodiment 2 (100 mg, 52%).

Embodiment 47

Preparation of methyl 2-(4-bromophenyl)-5-(4-(2-chloro-6-fluorobenzyl)piperazine-1-yl)-2-isopropylpentanoate Except that (2-chloro-6-fluorobenzyl)piperazine was used as a piperazine derivative in the Step 4, the target compound was obtained by carrying out the same processes as in the Embodiment 2 (125 mg, 66%).

Embodiment 48

Preparation of methyl 2-(3-bromophenyl)-5-(4-(2-fluorobenzyl)piperazine-1-yl)-2-isopropylpentanoate Except that (3-bromophenyl)acetic acid instead of (4-bromophenyl)acetic acid was used in the Step 1 and (2-fluorobenzyl)piperazine was used as a piperazine derivative in the Step 4, the target compound was obtained by carrying out the same processes as in the Embodiment 2 (95 mg, 68%).

Embodiment 49

Preparation of methyl 2-(3-bromophenyl)-5-(4-(3-fluorobenzyl)piperazine-1-yl)-2-isopropylpentanoate Except that (3-bromophenyl)acetic acid instead of (4-bromophenyl)acetic acid was used in the Step 1 and (3-fluorobenzyl)piperazine was used as a piperazine derivative in the Step 4, the target compound was obtained by carrying out the same processes as in the Embodiment 2 (98 mg, 71%).

Embodiment 50

Preparation of methyl 2-(3-bromophenyl)-5-(4-(4-fluorobenzyl)piperazine-1-yl)-2-isopropylpentanoate Except that (3-bromophenyl)acetic acid instead of (4-bromophenyl)acetic acid was used in the Step 1 and (4-fluorobenzyl)piperazine was used as a piperazine derivative in the Step 4, the target compound was obtained by carrying out the same processes as in the Embodiment 2 (94 mg, 68%).

Embodiment 51

Preparation of methyl 2-(3-bromophenyl)-2-isopropyl-5-(4-(3-(trifluoromethyl)benzyl)piperazine-1-yl)pentanoate Except that (3-bromophenyl)acetic acid instead of (4-bromophenyl)acetic acid was used in the Step 1 and (3-(trifluoromethyl)benzyl)piperazine was used as a piperazine derivative in the Step 4, the target compound was obtained by carrying out the same processes as in the Embodiment 2 (77 mg, 51%).

Embodiment 52

Preparation of methyl 2-(3-bromophenyl)-2-isopropyl-5-(4-(4-(trifluoromethyl)benzyl)piperazine-1-yl)pentanoate Except that (3-bromophenyl)acetic acid instead of (4-bromophenyl)acetic acid was used in the Step 1 and (4-(trifluoromethyl)benzyl)piperazine was used as a piperazine derivative in the Step 4, the target compound was obtained by carrying out the same processes as in the Embodiment 2 (77 mg, 51%).

Embodiment 53

Preparation of methyl 2-(3-bromophenyl)-2-isopropyl-5-(4-(4-methoxybenzyl)piperazine-1-yl)pentanoate Except that (3-bromophenyl)acetic acid instead of (4-bromophenyl)acetic acid was used in the Step 1 and (4-methoxybenzyl)piperazine was used as a piperazine derivative in the Step 4, the target compound was obtained by carrying out the same processes as in the Embodiment 2 (75 mg, 53%).

Embodiment 54

Preparation of methyl 2-(3-bromophenyl)-2-isopropyl-5-(4-(3,4,5-trimethoxybenzyl)piperazine-1-yl)pentanoate Except that (3-bromophenyl)acetic acid instead of (4-bromophenyl)acetic acid was used in the Step 1 and (3,4,5-trimethoxybenzyl)piperazine was used as a piperazine derivative in the Step 4, the target compound was obtained by carrying out the same processes as in the Embodiment 2 (104 mg, 66%).

Embodiment 55

Preparation of methyl 2-(3-bromophenyl)-2-isopropyl-5-(4-(3-methylbenzyl)piperazine-1-yl)pentanoate Except that (3-bromophenyl)acetic acid instead of (4-bromophenyl)acetic acid was used in the Step 1 and (3-methylbenzyl)piperazine was used as a piperazine derivative in the Step 4, the target compound was obtained by carrying out the same processes as in the Embodiment 2 (96 mg, 70%).

Embodiment 56

Preparation of methyl 2-(3-bromophenyl)-2-isopropyl-5-(4-(4-methylbenzyl)piperazine-1-yl)pentanoate Except that (3-bromophenyl)acetic acid instead of (4-bromophenyl)acetic acid was used in the Step 1 and (4-methylbenzyl)piperazine was used as a piperazine derivative in the Step 4, the target compound was obtained by carrying out the same processes as in the Embodiment 2 (75 mg, 54%).

Embodiment 57

Preparation of methyl 2-(3-bromophenyl)-5-(4-(4-t-butylbenzyl)piperazine-1-yl)-2-isopropylpentanoate Except that (3-bromophenyl)acetic acid instead of (4-bromophenyl)acetic acid was used in the Step 1 and (4-t-butylbenzyl)piperazine was used as a piperazine derivative in the Step 4, the target compound was obtained by carrying out the same processes as in the Embodiment 2 (89 mg, 60%).

Embodiment 58

Preparation of methyl 2-(3-bromophenyl)-5-(4-(3-chlorobenzyl)piperazine-1-yl)-2-isopropylpentanoate Except that (3-bromophenyl)acetic acid instead of (4-bromophenyl)acetic acid was used in the Step 1 and (3-chlorobenzyl)piperazine was used as a piperazine derivative in the Step 4, the target compound was obtained by carrying out the same processes as in the Embodiment 2 (96 mg, 67%).

Embodiment 59

Preparation of methyl 2-(3-bromophenyl)-5-(4-(4-chlorobenzyl)piperazine-1-yl)-2-isopropylpentanoate Except that (3-bromophenyl)acetic acid instead of (4-bromophenyl)acetic acid was used in the Step 1 and (4-chlorobenzyl)piperazine was used as a piperazine derivative in the Step 4, the target compound was obtained by carrying out the same processes as in the Embodiment 2 (114 mg, 80%).

Embodiment 60

Preparation of methyl 2-(3-bromophenyl)-5-(4-(3,4-dichlorobenzyl)piperazine-1-yl)-2-isopropylpentanoate Except that (3-bromophenyl)acetic acid instead of (4-bromophenyl)acetic acid was used in the Step 1 and (3,4-dichlorobenzyl)piperazine was used as a piperazine derivative in the Step 4, the target compound was obtained by carrying out the same processes as in the Embodiment 2 (79 mg, 55%).

Embodiment 61

Preparation of methyl 2-(4-fluorophenyl)-2-isopropyl-5-(4-phenylpiperazine-1-yl)pentanoate Except that (4-fluorophenyl)acetic acid instead of (4-bromophenyl)acetic acid was used in the Step 1 and phenylpiperazine was used as a piperazine derivative in the Step 4, the target compound was obtained by carrying out the same processes as in the Embodiment 2 (145 mg, 59%).

Embodiment 62

Preparation of methyl 5-(4-benzhydrylpiperazine-1-yl)-2-(4-fluorophenyl)-2-isopropylpentanoate Except that (4-fluorophenyl)acetic acid instead of (4-bromophenyl)acetic acid was used in the Step 1 and benzhydrylpiperazine was used as a piperazine derivative in the Step 4, the target compound was obtained by carrying out the same processes as in the Embodiment 2 (45 mg, 30%).

Embodiment 63

Preparation of methyl 2-(4-fluorophenyl)-5-(4-(2-fluorophenyl)piperazine-1-yl)-2-isopropylpentanoate Except that (4-fluorophenyl)acetic acid instead of (4-bromophenyl)acetic acid was used in the Step 1 and (2-fluorophenyl)piperazine was used as a piperazine derivative in the Step 4, the target compound was obtained by carrying out the same processes as in the Embodiment 2 (69 mg, 53%).

Embodiment 64

Preparation of methyl 2-(4-fluorophenyl)-5-(4-(4-fluorophenyl)piperazine-1-yl)-2-isopropylpentanoate Except that (4-fluorophenyl)acetic acid instead of (4-bromophenyl)acetic acid was used in the Step 1 and (4-fluorophenyl)piperazine was used as a piperazine derivative in the Step 4, the target compound was obtained by carrying out the same processes as in the Embodiment 2 (88 mg, 68%).

Embodiment 65

Preparation of methyl 5-(4-(2-fluorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (2-fluorobenzyl)piperazine was used as a piperazine derivative in the Step 4, the target compound was obtained by carrying out the same processes as in the Embodiment 2 (80 mg, 60%).

Embodiment 66

Preparation of methyl 5-(4-(3-fluorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (3-fluorobenzyl)piperazine was used as a piperazine derivative in the Step 4, the target compound was obtained by carrying out the same processes as in the Embodiment 2 (120 mg, 90%).

Embodiment 67

Preparation of methyl 5-(4-(4-fluorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (4-fluorobenzyl)piperazine was used as a piperazine derivative in the Step 4, the target compound was obtained by carrying out the same processes as in the Embodiment 2 (106 mg, 79%).

Embodiment 68

Preparation of methyl 2-(4-fluorophenyl)-2-isopropyl-5-(4-(3-(trifluoromethyl)benzyl)piperazine-1-yl)pentanoate Except that (4-fluorophenyl)acetic acid instead of (4-bromophenyl)acetic acid was used in the Step 1 and (3-(trifluoromethyl)benzyl)piperazine was used as a piperazine derivative in the Step 4, the target compound was obtained by carrying out the same processes as in the Embodiment 2 (154 mg, 52%).

Embodiment 69

Preparation of methyl 2-(4-fluorophenyl)-2-isopropyl-5-(4-(4-(trifluoromethyl)benzyl)piperazine-1-yl)pentanoate Except that phenylacetic acid instead of (4-bromophenyl)acetic acid was used in the Step 1 and (4-(trifluoromethyl)benzyl)piperazine was used as a piperazine derivative in the Step 4, the target compound was obtained by carrying out the same processes as in the Embodiment 2 (110 mg, 37%).

Embodiment 70

Preparation of methyl 2-(4-fluorophenyl)-2-isopropyl-5-(4-(2-methoxyphenyl)piperazine-1-yl)pentanoate Except that (4-fluorophenyl)acetic acid instead of (4-bromophenyl)acetic acid was used in the Step 1 and (2-methoxyphenyl)piperazine was used as a piperazine derivative in the Step 4, the target compound was obtained by carrying out the same processes as in the Embodiment 2 (110 mg, 41%).

Embodiment 71

Preparation of methyl 2-(4-fluorophenyl)-2-isopropyl-5-(4-(3-methoxyphenyl)piperazine-1-yl)pentanoate Except that phenylacetic acid instead of (4-bromophenyl)acetic acid was used in the Step 1 and (3-methoxyphenyl)piperazine was used as a piperazine derivative in the Step 4, the target compound was obtained by carrying out the same processes as in the Embodiment 2 (155 mg, 58%).

Embodiment 72

Preparation of methyl 2-(4-fluorophenyl)-2-isopropyl-5-(4-(4-methoxyphenyl)piperazine-1-yl)pentanoate Except that (4-fluorophenyl)acetic acid instead of (4-bromophenyl)acetic acid was used in the Step 1 and (4-methoxyphenyl)piperazine was used as a piperazine derivative in the Step 4, the target compound was obtained by carrying out the same processes as in the Embodiment 2 (172 mg, 65%).

Embodiment 73

Preparation of methyl 2-(4-fluorophenyl)-2-isopropyl-5-(4-(4-methoxybenzyl)piperazine-1-yl)pentanoate Except that phenylacetic acid instead of (4-bromophenyl)acetic acid was used in the Step 1 and (4-methoxybenzyl)piperazine was used as a piperazine derivative in the Step 4, the target compound was obtained by carrying out the same processes as in the Embodiment 2 (186 mg, 68%).

Embodiment 74

Preparation of methyl 2-(4-fluorophenyl)-2-isopropyl-5-(4-(2,3,4-trimethoxybenzyl)piperazine-1-yl)pentanoate Except that (4-fluorophenyl)acetic acid instead of (4-bromophenyl)acetic acid was used in the Step 1 and (2,3,4-trimethoxybenzyl)piperazine was used as a piperazine derivative in the Step 4, the target compound was obtained by carrying out the same processes as in the Embodiment 2 (187 mg, 60%).

Embodiment 75

Preparation of methyl 2-(4-fluorophenyl)-2-isopropyl-5-(4-(3-methylbenzyl)piperazine-1-yl)pentanoate Except that (4-fluorophenyl)acetic acid instead of (4-bromophenyl)acetic acid was used in the Step 1 and (3-methylbenzyl)piperazine was used as a piperazine derivative in the Step 4, the target compound was obtained by carrying out the same processes as in the Embodiment 2 (222 mg, 84%).

Embodiment 76

Preparation of methyl 2-(4-fluorophenyl)-2-isopropyl-5-(4-(4-methylbenzyl)piperazine-1-yl)pentanoate Except that (4-fluorophenyl)acetic acid instead of (4-bromophenyl)acetic acid was used in the Step 1 and (4-methylbenzyl)piperazine was used as a piperazine derivative in the Step 4, the target compound was obtained by carrying out the same processes as in the Embodiment 2 (201 mg, 76%).

Embodiment 77

Preparation of methyl 5-(4-(4-t-butylbenzyl)piperazine-1-yl)-2-(4-fluorophenyl)-2-isopropylpentanoate Except that (4-fluorophenyl)acetic acid instead of (4-bromophenyl)acetic acid was used in the Step 1 and (4-t-butylbenzyl)piperazine was used as a piperazine derivative in the Step 4, the target compound was obtained by carrying out the same processes as in the Embodiment 2 (150 mg, 55%).

Embodiment 78

Preparation of methyl 5-(4-(3-chlorophenyl)piperazine-1-yl)-2-(4-fluorophenyl)-2-isopropylpentanoate Except that (4-fluorophenyl)acetic acid instead of (4-bromophenyl)acetic acid was used in the Step 1 and (3-chlorophenyl)piperazine was used as a piperazine derivative in the Step 4, the target compound was obtained by carrying out the same processes as in the Embodiment 2 (207 mg, 77%).

Embodiment 79

Preparation of methyl 5-(4-(3-chlorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (3-chlorobenzyl)piperazine was used as a piperazine derivative in the Step 4, the target compound was obtained by carrying out the same processes as in the Embodiment 2 (238 mg, 86%).

Embodiment 80

Preparation of methyl 5-(4-(4-chlorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (4-chlorobenzyl)piperazine was used as a piperazine derivative in the Step 4, the target compound was obtained by carrying out the same processes as in the Embodiment 2 (194 mg, 70%).

Embodiment 81

Preparation of methyl 5-(4-(3,4-dichlorobenzyl)piperazine-1-yl)-2-(4-fluorophenyl)-2-isopropylpentanoate Except that (4-fluorophenyl)acetic acid instead of (4-bromophenyl)acetic acid was used in the Step 1 and (3,4-dichlorobenzyl)piperazine was used as a piperazine derivative in the Step 4, the target compound was obtained by carrying out the same processes as in the Embodiment 2 (239 mg, 80%).

Embodiment 82

Preparation of methyl 2-(4-bromophenyl)-2-isopropyl-5-(4-(4-methoxybenzyl)piperidine-1-yl)pentanoate Except that (4-methoxybenzyl)piperidine was used as a piperidine derivative in the Step 4, the target compound was obtained by carrying out the same processes as in the Embodiment 3 (232 mg, 80%).

Embodiment 83

Preparation of methyl 2-(4-bromophenyl)-2-isopropyl-5-(4-(3-methoxybenzylidene)piperidine-1-yl)pentanoate Except that (3-methoxybenzylidene)piperidine was used as a piperidine derivative in the Step 4, the target compound was obtained by carrying out the same processes as in the Embodiment 3 (219 mg, 86%).

Embodiment 84

Preparation of methyl 2-(4-bromophenyl)-2-isopropyl-5-(4-(3-methoxybenzyl)piperidine-1-yl)pentanoate Except that (3-methoxybenzyl)piperidine was used as a piperidine derivative in the Step 4, the target compound was obtained by carrying out the same processes as in the Embodiment 3 (207 mg, 81%).

Embodiment 85

Preparation of methyl 2-(4-bromophenyl)-2-isopropyl-5-(4-(4-methylbenzylidene)piperidine-1-yl)pentanoate Except that (4-methylbenzylidene)piperidine was used as a piperidine derivative in the Step 4, the target compound was obtained by carrying out the same processes as in the Embodiment 3 (236 mg, 92%).

Embodiment 86

Preparation of methyl 2-(4-bromophenyl)-2-isopropyl-5-(4-(4-methylbenzyl)piperidine-1-yl)pentanoate Except that (4-methylbenzyl)piperidine was used as a piperidine derivative in the Step 4, the target compound was obtained by carrying out the same processes as in the Embodiment 3 (226 mg, 85%).

Embodiment 87

Preparation of methyl 2-(4-bromophenyl)-2-isopropyl-5-(4-(3-methylbenzylidene)piperidine-1-yl)pentanoate Except that (3-methylbenzylidene)piperidine was used as a piperidine derivative in the Step 4, the target compound was obtained by carrying out the same processes as in the Embodiment 3 (224 mg, 85%).

Embodiment 88

Preparation of methyl 2-(4-bromophenyl)-2-isopropyl-5-(4-(3-methylbenzyl)piperidine-1-yl)pentanoate Except that (3-methylbenzyl)piperidine was used as a piperidine derivative in the Step 4, the target compound was obtained by carrying out the same processes as in the Embodiment 3 (225 mg, 88%).

Embodiment 89

Preparation of methyl 2-(4-bromophenyl)-2-isopropyl-5-(4-(2-methylbenzylidene)piperidine-1-yl)pentanoate Except that (2-methylbenzylidene)piperidine was used as a piperidine derivative in the Step 4, the target compound was obtained by carrying out the same processes as in the Embodiment 3 (93 mg, 71%).

Embodiment 90

Preparation of methyl 2-(4-bromophenyl)-2-isopropyl-5-(4-(2-methylbenzyl)piperidine-1-yl)pentanoate Except that (2-methylbenzyl)piperidine was used as a piperidine derivative in the Step 4, the target compound was obtained by carrying out the same processes as in the Embodiment 3 (98 mg, 74%).

Embodiment 91

Preparation of methyl 2-(4-bromophenyl)-5-(4-(4-chlorobenzylidene)piperidine-1-yl)-2-isopropylpentanoate Except that (4-chlorobenzylidene)piperidine was used as a piperidine derivative in the Step 4, the target compound was obtained by carrying out the same processes as in the Embodiment 3 (114 mg, 88%).

Embodiment 92

Preparation of methyl 2-(4-bromophenyl)-5-(4-(4-chlorobenzyl)piperidine-1-yl)-2-isopropylpentanoate Except that (4-chlorobenzyl)piperidine was used as a piperidine derivative in the Step 4, the target compound was obtained by carrying out the same processes as in the Embodiment 3 (113 mg, 87%).

Embodiment 93

Preparation of methyl 2-(4-bromophenyl)-5-(4-(3-chlorobenzylidene)piperidine-1-yl)-2-isopropylpentanoate Except that (3-chlorobenzylidene)piperidine was used as a piperidine derivative in the Step 4, the target compound was obtained by carrying out the same processes as in the Embodiment 3 (81 mg, 80%).

Embodiment 94

Preparation of methyl 2-(4-bromophenyl)-5-(4-(3-chlorobenzyl)piperidine-1-yl)-2-isopropylpentanoate Except that (3-chlorobenzyl)piperidine was used as a piperidine derivative in the Step 4, the target compound was obtained by carrying out the same processes as in the Embodiment 3 (118 mg, 87%).

Embodiment 95

Preparation of methyl 2-(4-bromophenyl)-5-(4-(4-fluorobenzylidene)piperidine-1-yl)-2-isopropylpentanoate Except that (4-fluorobenzylidene)piperidine was used as a piperidine derivative in the Step 4, the target compound was obtained by carrying out the same processes as in the Embodiment 3 (105 mg, 77%).

Embodiment 96

Preparation of methyl 2-(4-bromophenyl)-5-(4-(4-fluorobenzyl)piperidine-1-yl)-2-isopropylpentanoate Except that (4-fluorobenzyl)piperidine was used as a piperidine derivative in the Step 4, the target compound was obtained by carrying out the same processes as in the Embodiment 3 (129 mg, 98%).

Embodiment 97

Preparation of methyl 2-isopropyl-5-(4-(4-methoxybenzylidene)piperidine-1-yl)-2-(4-methoxyphenyl)pentanoate Except that phenylacetic acid instead of (4-bromophenyl)acetic acid was used in the Step 1 and (4-methoxybenzylidene)piperidine was used as a piperidine derivative in the Step 4, the target compound was obtained by carrying out the same processes as in the Embodiment 3 (231 mg, 88%).

Embodiment 98

Preparation of methyl 2-isopropyl-5-(4-(4-methoxybenzyl)piperidine-1-yl)-2-(4-methoxyphenyl)pentanoate Except that (4-methoxyphenyl)acetic acid instead of (4-bromophenyl)acetic acid was used in the Step 1 and (4-methoxybenzyl)piperidine was used as a piperidine derivative in the Step 4, the target compound was obtained by carrying out the same processes as in the Embodiment 3 (196 mg, 75%).

Embodiment 99

Preparation of methyl 2-isopropyl-5-(4-(3-methoxybenzylidene)piperidine-1-yl)-2-(4-methoxyphenyl)pentanoate Except that (4-methoxyphenyl)acetic acid instead of (4-bromophenyl)acetic acid was used in the Step 1 and (3-methoxybenzylidene)piperidine was used as a piperidine derivative in the Step 4, the target compound was obtained by carrying out the same processes as in the Embodiment 3 (214 mg, 84%).

Embodiment 100

Preparation of methyl 2-isopropyl-5-(4-(3-methoxybenzyl)piperidine-1-yl)-2-(4-methoxyphenyl)pentanoate Except that (4-methoxyphenyl)acetic acid instead of (4-bromophenyl)acetic acid was used in the Step 1 and (3-methoxybenzyl)piperidine was used as a piperidine derivative in the Step 4, the target compound was obtained by carrying out the same processes as in the Embodiment 3 (222 mg, 87%).

Embodiment 101

Preparation of methyl 2-isopropyl-2-(4-methoxyphenyl)-5-(4-(4-methylbenzylidene)piperidine-1-yl)pentanoate Except that (4-methoxyphenyl)acetic acid instead of (4-bromophenyl)acetic acid was used in the Step 1 and (4-methylbenzylidene)piperidine was used as a piperidine derivative in the Step 4, the target compound was obtained by carrying out the same processes as in the Embodiment 3 (222 mg, 87%).

Embodiment 102

Preparation of methyl 2-isopropyl-2-(4-methoxyphenyl)-5-(4-(4-methylbenzyl)piperidine-1-yl)pentanoate Except that (4-methoxyphenyl)acetic acid instead of (4-bromophenyl)acetic acid was used in the Step 1 and (4-methylbenzyl)piperidine was used as a piperidine derivative in the Step 4, the target compound was obtained by carrying out the same processes as in the Embodiment 3 (217 mg, 82%).

Embodiment 103

Preparation of methyl 2-isopropyl-2-(4-methoxyphenyl)-5-(4-(3-methylbenzylidene)piperidine-1-yl)pentanoate Except that (4-methoxyphenyl)acetic acid instead of (4-bromophenyl)acetic acid was used in the Step 1 and (3-methylbenzylidene)piperidine was used as a piperidine derivative in the Step 4, the target compound was obtained by carrying out the same processes as in the Embodiment 3 (228 mg, 86%).

Embodiment 104

Preparation of methyl 2-isopropyl-2-(4-methoxyphenyl)-5-(4-(3-methylbenzyl)piperidine-1-yl)pentanoate Except that (4-methoxyphenyl)acetic acid instead of (4-bromophenyl)acetic acid was used in the Step 1 and (3-methylbenzyl)piperidine was used as a piperidine derivative in the Step 4, the target compound was obtained by carrying out the same processes as in the Embodiment 3 (222 mg, 86%).

Embodiment 105

Preparation of methyl 2-isopropyl-2-(4-methoxyphenyl)-5-(4-(2-methylbenzylidene)piperidine-1-yl)pentanoate Except that (4-methoxyphenyl)acetic acid instead of (4-bromophenyl)acetic acid was used in the Step 1 and (2-methylbenzylidene)piperidine was used as a piperidine derivative in the Step 4, the target compound was obtained by carrying out the same processes as in the Embodiment 3 (107 mg, 79%).

Embodiment 106

Preparation of methyl 2-isopropyl-2-(4-methoxyphenyl)-5-(4-(2-methylbenzyl)piperidine-1-yl)pentanoate Except that (4-methoxyphenyl)acetic acid instead of (4-bromophenyl)acetic acid was used in the Step 1 and (2-methylbenzyl)piperidine was used as a piperidine derivative in the Step 4, the target compound was obtained by carrying out the same processes as in the Embodiment 3 (111 mg, 82%).

Embodiment 107

Preparation of methyl 5-(4-(4-chlorobenzylidene)piperidine-1-yl)-2-isopropyl-2-(4-methoxyphenyl)pentanoate Except that (4-methoxyphenyl)acetic acid instead of (4-bromophenyl)acetic acid was used in the Step 1 and (4-chlorobenzylidene)piperidine was used as a piperidine derivative in the Step 4, the target compound was obtained by carrying out the same processes as in the Embodiment 3 (109 mg, 83%).

Embodiment 108

Preparation of methyl 5-(4-(4-chlorobenzyl)piperidine-1-yl)-2-isopropyl-2-(4-methoxyphenyl)pentanoate Except that (4-methoxyphenyl)acetic acid instead of (4-bromophenyl)acetic acid was used in the Step 1 and (4-chlorobenzyl)piperidine was used as a piperidine derivative in the Step 4, the target compound was obtained by carrying out the same processes as in the Embodiment 3 (106 mg, 81%).

Embodiment 109

Preparation of methyl 5-(4-(3-chlorobenzylidene)piperidine-1-yl)-2-isopropyl-2-(4-methoxyphenyl)pentanoate Except that (4-methoxyphenyl)acetic acid instead of (4-bromophenyl)acetic acid was used in the Step 1 and (3-chlorobenzylidene)piperidine was used as a piperidine derivative in the Step 4, the target compound was obtained by carrying out the same processes as in the Embodiment 3 (81 mg, 62%).

Embodiment 110

Preparation of methyl 5-(4-(3-chlorobenzyl)piperidine-1-yl)-2-isopropyl-2-(4-methoxyphenyl)pentanoate Except that (4-methoxyphenyl)acetic acid instead of (4-bromophenyl)acetic acid was used in the Step 1 and (3-chlorobenzyl)piperidine was used as a piperidine derivative in the Step 4, the target compound was obtained by carrying out the same processes as in the Embodiment 3 (122 mg, 89%).

Embodiment 111

Preparation of methyl 5-(4-(4-fluorobenzylidene)piperidine-1-yl)-2-isopropyl-2-(4-methoxyphenyl)pentanoate Except that (4-methoxyphenyl)acetic acid instead of (4-bromophenyl)acetic acid was used in the Step 1 and (4-fluorobenzylidene)piperidine was used as a piperidine derivative in the Step 4, the target compound was obtained by carrying out the same processes as in the Embodiment 3 (118 mg, 86%).

Embodiment 112

Preparation of methyl 5-(4-(4-fluorobenzyl)piperidine-1-yl)-2-isopropyl-2-(4-methoxyphenyl)pentanoate Except that (4-methoxyphenyl)acetic acid instead of (4-bromophenyl)acetic acid was used in the Step 1 and (4-fluorobenzyl)piperidine was used as a piperidine derivative in the Step 4, the target compound was obtained by carrying out the same processes as in the Embodiment 3 (97 mg, 73%).

The structure and $^1$H NMR data of the phenylacetate derivatives in the Embodiment 4-112 obtained by the preparation method of the present invention are described in the following Table 1.

TABLE 1

| Embodiment | Structure | NMR |
|---|---|---|
| 4 | (structure image) | 7.45 (bs, 2H), 7.17 (dd. J=6.0, 3.2 Hz, 2H), 7.04 (d, J=8.8 Hz, 2H), 6.80 (d, J=8.9 Hz, 2H), 3.77 (s, 3H), 3.69 (s, 3H), 3.05 (t, J=6.3 Hz, 2H), 2.49 (t, J=5.9 Hz, 2H), 2.42-2.36 (m, 3H), 2.23 (s, 3H), 2.17-2.10 (m, 1H), 1.96-1.87 (m, 4H), 1.49-1.25 (m, 2H), 0.87 (d, J=6.7 Hz, 3H), 0.77 (d, J=6.8 Hz, 3H) |
| 5 | (structure image) | 7.34-7.32 (m, 1H), 7.03 (d, J=8.8 Hz, 2H), 6.97 (bs, 1H), 6.81-6.75 (m, 3H), 3.81 (s, 3H), 3.76 (s, 3H), 3.68 (s, 3H), 2.98 (t, J=6.3 Hz, 2H), 2.45 (d, J=5.8 Hz, 2H), 2.40-2.34 (m, 3H), 2.19 (s, 3H), 2.09-2.06 (m, 1H), 1.93-1.87 (m, 3H), 1.44-1.26 (m, 2H), 0.84 (d, J=6.7 Hz, 3H), 0.75 (d, J=6.8 Hz, 3H) |

TABLE 1-continued

| Embodiment | Structure | NMR |
|---|---|---|
| 6 | 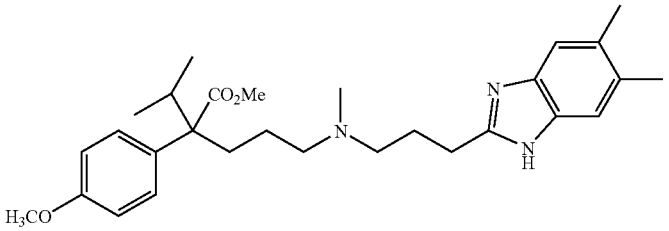 | 7.25 (bs, 2H), 7.04 (d, J=8.8 Hz, 2H), 6.79 (d, J=8.8 Hz, 2H), 3.76 (s, 3H), 3.69 (s, 3H), 3.00-2.97 (m, 2H), 2.44 (t, J=5.9 Hz, 2H), 2.40-2.33 (m, 3H), 2.33 (s, 6H), 2.16 (s, 3H), 2.20-2.06 (m, 1H), 1.96-2.88 (m, 3H), 1.45-1.26 (m, 2H), 0.85 (d, J=6.7 Hz, 3H), 0.75 (d, J=6.8 Hz, 3H) |
| 7 | 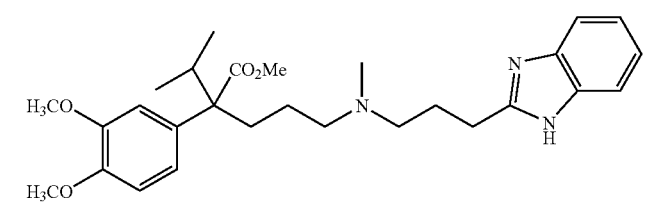 | 7.52-7.50 (m, 2H), 7.17-7.15 (m, 2H), 6.74 (d, J=8.3 Hz, 1H), 6.68-6.64 (m, 2H), 3.84 (s, 3H), 3.79 (s, 3H), 3.69 (s, 3H), 3.03 (t, J=6.3 Hz, 2H), 2.49 (t J=5.6 Hz, 2H), 2.42-2.37 (m, 3H), 2.22 (s, 3H), 2.14-2.11 (m, 2H), 1.95-1.89 (m, 3H), 1.48-1.25 (m, 2H), 0.87 (d, J=6.7 Hz, 3H), 0.77 (d, J=6.7 Hz, 3H) |
| 8 | 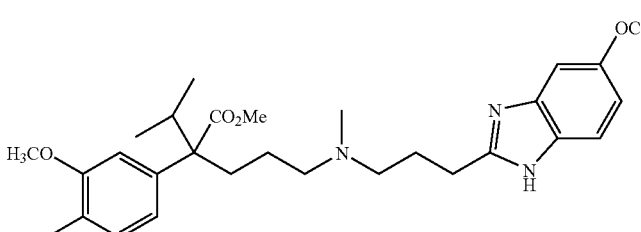 | 7.41-7.31 (m, 1H), 6.99 (m, 1H), 6.81 (dd, J=8.7, 2.4 Hz, 1H), 6.74 (d, J=8.4 Hz, 1H), 6.69-6.64 (m, 2H), 3.85 (s, 3H), 3.82 (s, 3H), 3.80 (s, 3H), 3.70 (s, 3H), 3.02-2.99 (m, 3H), 2.47 (t, J=5.1 Hz, 2H), 2.41-2.40 (m, 4H), 2.23 (s, 3H), 2.12-2.08 (m, 2H), 1.94-1.91 (m, 3H), 1.49-1.25 (m, 2H), 0.87 (d, J=6.7 Hz, 3H), 0.79 (d, J=6.8 Hz, 3H) |
| 9 | 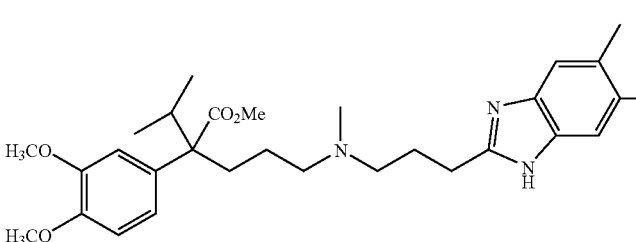 | 7.25 (s, 1H), 6.74 (d, J=8.3 Hz, 1H), 6.96-6.61 (m, 2H), 3.83 (s, 3H), 3.79 (s, 3H), 3.70 (s, 3H), 2.99-2.96 (m, 2H), 2.51-2.36 (m, 5H), 2.32 (s, 6H), 2.18 (s, 3H), 2.11-2.08 (m, 2H), 1.96-1.90 (m, 3H), 1.45-1.27 (m, 2H), 0.87 (d, J=6.7 Hz, 3H), 0.78 (d, J=6.8 Hz, 3H) |
| 10 | 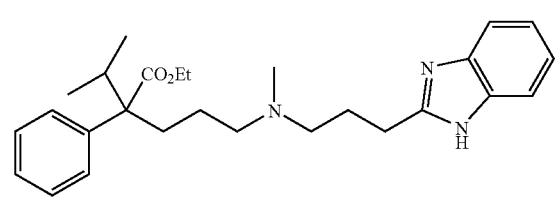 | 7.53-7.43 (m, 2H), 7.29-7.27 (m, 1H), 7.23-7.21 (m, 1H), 7.18-7.10 (m, 5H), 4.24-4.18 (m, 2H), 3.07 (t, J=6.3 Hz, 2H), 2.51 (t, J=5.7 Hz, 2H), 2.45-2.39 (m, 3H), 2.31 (s, 3H), 2.19 (m, 1H), 1.96-1.95 (m, 4H), 1.54-1.49 (m, 2H), 1.23 (t, J=7.1 Hz, 3H), 0.88 (d, J=6.8 Hz, 3H), 0.80 (d, J=6.8 Hz, 3H) |
| 11 | 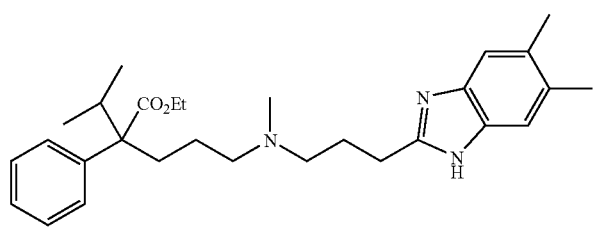 | 7.29-7.27 (m, 2H), 7.25-7.18 (m, 3H), 7.15-7.13 (m, 2H), 4.24-4.22 (m, 2H), 3.01-2.98 (m, 2H), 2.46-2.38 (m, 5H), 2.33 (s, 6H), 2.18 (m, 3H), 1.92-1.89 (m, 3H), 1.50-1.46 (m, 2H), 1.24 (t, J=7.1 Hz, 3H), 0.88 (d, J=6.7 Hz, 3H), 0.79 (d, J=6.8 Hz, 3H) |
| 12 | 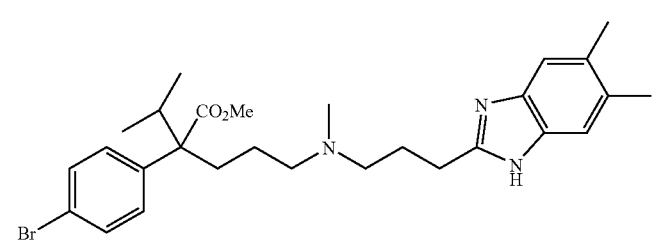 | 7.39 (d, J=8.5 Hz, 2H), 6.99 (d, J=8.6 Hz, 2H), 3.68 (s, 3H), 2.97 (t, J=6.7 Hz, 2H), 2.43 (t, J=6.3 Hz, 2H), 2.39-2.34 (m, 3H), 2.32 (s, 6H), 2.16 (s, 3H), 2.10-2.03 (m, 1H), 1.96-1.87 (m, 3H), 1.41-1.20 (m, 2H), 0.83 (d, J=6.7 Hz, 3H), 0.72 (d, J=6.8 Hz, 3H) |

TABLE 1-continued

| Embodiment | Structure | NMR |
|---|---|---|
| 13 | 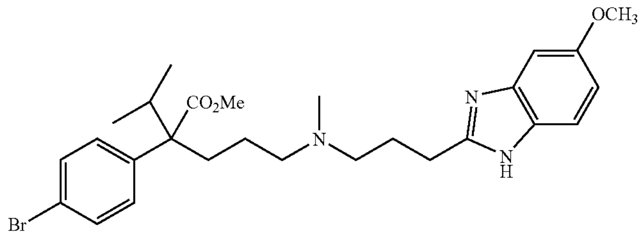 | 7.39 (dd, J=6.8, 1.9 Hz, 2H), 7.33 (d, J=7.7 Hz, 1H), 7.02-6.99 (m, 3H), 6.82 (dd, J=8.7, 2.4 Hz, 1H), 3.82 (s, 3H), 3.68 (s, 3H), 3.00 (t, J=6.3 Hz, 2H), 2.46 (t, J=5.9 Hz, 2H), 2.38-2.34 (m, 3H), 2.20 (s, 3H), 2.09-2.06 (m, 1H), 1.96-1.90 (m, 3H), 1.44-1.23 (m, 2H), 0.84 (d, J=6.7 Hz, 3H), 0.73 (d, J=6.8 Hz, 3H) |
| 14 | 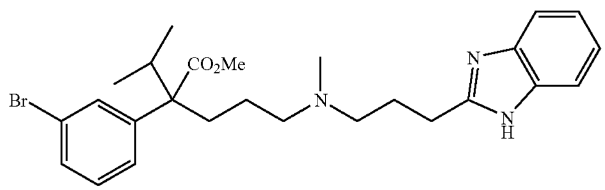 | 10.95 (s, 1H), 7.44 (dd, J=6.0, 3.2 Hz, 1H), 7.39-7.36 (m, 1H), 7.31-7.30 (m, 1H), 7.20-7.15 (m, 3H), 7.12 (d, J=7.9 Hz, 1H), 7.06-7.04 (m, 1H), 3.75 (s, 1H), 3.70 (s, 3H), 3.16 (t, J=6.2 Hz, 2H), 2.82-2.79 (m, 1H), 2.69-2.64 (m, 1H), 2.42 (s, 3H), 2.35-2.30 (m, 1H), 2.14-2.02 (m, 3H), 1.86-1.82 (m, 1H), 1.31-1.25 (m, 2H), 0.85 (d, J=6.7 Hz, 3H), 0.77 (d, J=6.8 Hz, 3H) |
| 15 | 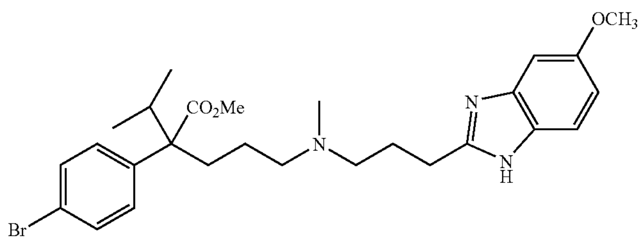 | 7.48-7.22 (m, 3H), 7.16-7.00 (m, 3H), 6.84-6.80 (m, 1H), 3.80 (s, 3H), 3.76 (s, 3H), 3.72 (s, 3H), 3.29-3.23 (m, 5H), 3.10-3.07 (m, 2H), 2.95-2.90 (m, 2H), 2.65 (s, 2H), 2.33-2.29 (m, 2H), 2.20-2.16 (m, 3H), 1.89-1.79 (m, 2H), 1.68-1.65 (m, 1H), 1.38-1.32 (m, 1H), 0.85 (d, J=6.6 Hz, 3H), 0.77 (d, J=6.9 Hz, 3H) |
| 16 | 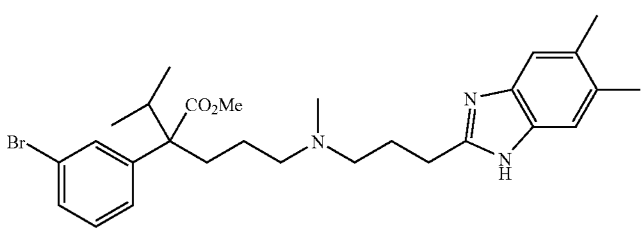 | 7.38-7.27 (m, 2H), 7.24-7.22 (m, 1H), 7.19-7.10 (m, 2H), 7.07-7.01 (m, 1H), 3.74 (s, 3H), 3.70 (s, 1H), 3.67 (s, 3H), 3.21-3.18 (m, 2H), 3.05-3.03 (m, 2H), 2.73-2.68 (m, 1H), 2.34 (s, 2H), 2.30 (s, 6H), 2.02 (m, 2H), 1.85-1.75 (m, 2H), 1.24 (s, 2H), 0.84 (d, J=6.7 Hz, 3H), 0.75 (d, J=6.8 Hz, 3H) |
| 17 | 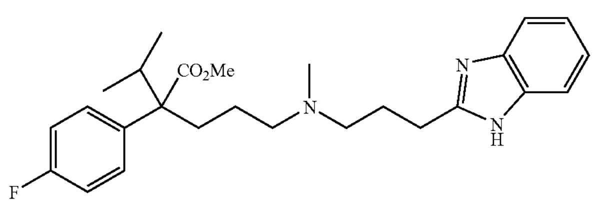 | 12.05 (bs, 1H), 7.44 (s, 2H), 7.17 (dd, J=8.3, 5.7 Hz, 2H), 7.12-7.08 (m, 4H), 3.64 (s, 3H), 2.79 (t, J=7.4 Hz, 2H), 2.38-2.33 (m, 5H), 2.20 (s, 3H), 1.92-1.87 (m, 3H), 1.23-1.19 (m, 1H), 1.05-1.03 (m, 1H), 0.76 (d, J=6.6 Hz, 3H), 0.66 (d, J=6.7 Hz, 3H) |
| 18 | 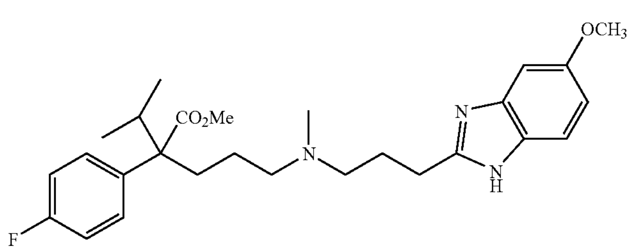 | 13.83 (bs, 1H), 7.32 (d, J=8.7 Hz, 1H), 7.19-7.08 (m, 4H), 6.96 (s, 1H), 6.73 (dd, J=8.7, 2.3 Hz, 1H), 3.75 (s, 3H), 3.69 (s, 3H), 2.76 (t, J=7.3 Hz, 2H), 2.38-2.23 (m, 5H), 2.16 (s, 3H), 2.04-1.97 (m, 1H), 1.92-1.87 (m, 3H), 1.23-1.16 (m, 2H), 1.14-1.06 (m, 1H), 0.76 (d, J=6.6 Hz, 3H), 0.66 (d, J=6.7 Hz, 3H) |

TABLE 1-continued

| Embodiment | Structure | NMR |
|---|---|---|
| 19 | 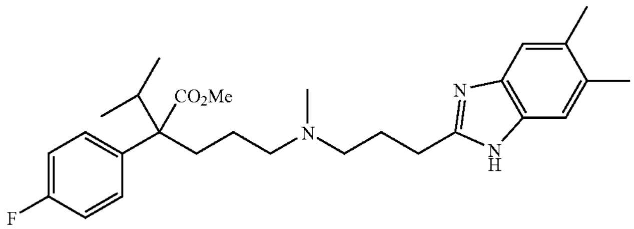 | 11.83 (bs, 1H), 7.20 (s, 1H), 7.18-7.14 (m, 2H), 7.12-7.08 (m, 2H), 3.64 (s, 3H), 2.74 (t, J=7.4 Hz, 2H), 2.37-2.30 (m, 3H), 2.27 (s, 8H), 1.98-1.96 (m, 1H), 1.92-1.82 (m, 4H), 1.23-1.20 (m, 1H), 1.04-1.01 (m, 1H), 0.76 (d, J=6.7 Hz, 3H), 0.66 (d, J=6.8 Hz, 3H) |
| 20 | 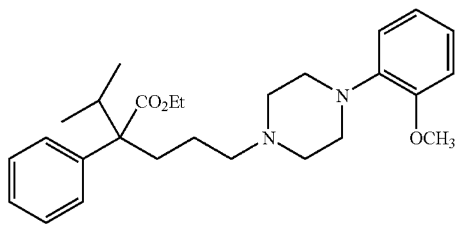 | 7.32-7.27 (m, 2H), 7.22-7.13 (m, 3H), 6.93-6.86 (m, 2H), 6.83 (dd, J=4.6, 1.7 Hz, 2H), 4.19 (q, J=7.0 Hz, 2H), 3.73 (s, 3H), 3.37 (t, J=7.0 Hz, 3H), 2.89 (bs, 3H), 2.41-2.36 (m, 5H), 2.23 (t, J=7.0 Hz, 2H), 2.05-1.90 (m, 2H), 1.29-1.22 (m, 1H), 1.07 (t, J=7.0 Hz, 6H), 0.79 (d, J=6.7 Hz, 3H), 0.72 (d, J=6.7 Hz, 3H) |
| 21 | 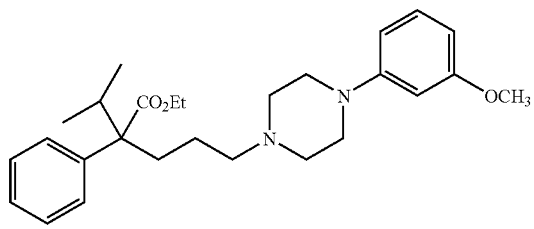 | 7.30 (dd, J=7.8, 7.2 Hz, 2H), 7.21 (m, 1H), 7.15 (d, J=7.8 Hz, 2H), 7.06 (dd, J=8.2, 8.0 Hz, 1H), 6.47 (d, J=8.2 Hz, 1H), 6.39 (d, J=1.9 Hz, 1H), 6.32 (d, J=8.0 Hz, 1H), 4.14 (q, J=7.1 Hz, 2H), 3.68 (s, 3H), 3.04 (s, 4H), 2.42-2.34 (m, 4H), 2.22 (t, J=6.8 Hz, 2H), 2.04-2.01 (m, 1H), 1.92-1.87 (m, 1H), 1.29-1.19 (m, 1H), 1.17 (t, J=7.1 Hz, 3H), 1.08-1.04 (m, 1H), 0.79 (d, J=6.6 Hz, 3H), 0.71 (d, J=6.7 Hz, 3H) |
| 22 | 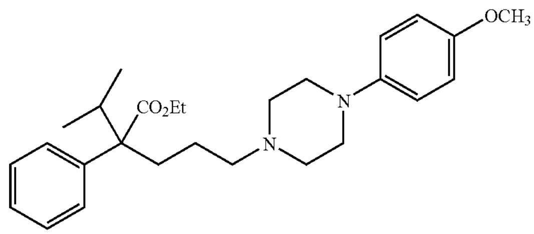 | 7.31-7.28 (m, 2H), 7.22-7.13 (m, 3H), 6.48 (dd, J=9.6, 2.8 Hz, 2H), 6.78 (dd, J=9.6, 2.8 Hz, 2H, 4.13 (q, J=7.0 Hz, 2H), 3.65 (s, 3H), 2.93 (t, J=4.7 Hz, 3H), 2.35 (t, J=4.7 Hz, 5H), 2.22 (t, J=7.0 Hz, 2H), 2.21-1.86 (m, 2H), 1.28-1.03 (m, 2H), 0.79 (d, J=6.7 Hz, 3H), 0.71 (d, J=6.8 Hz, 3H) |
| 23 | 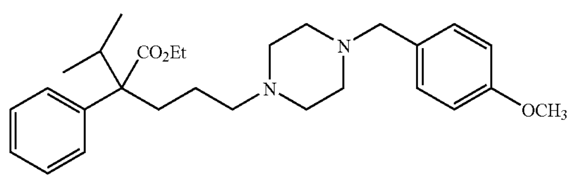 | 7.29-7.27 (m, 2H), 7.20-7.13 (m, 5H), 6.83 (d, J=8.4 Hz, 2H), 4.20 (q, J=7.1 Hz, 2H), 3.79 (s, 3H), 3.42 (s, 2H), 2.46-2.39 (m, 8H), 2.33-2.25 (m, 3H), 2.07-1.92 (m, 2H), 1.24 (t, J=7.1 Hz, 3H), 0.88 (d, J=6.7 Hz, 3H), 0.78 (d, J=6.9 Hz, 3H) |
| 24 | 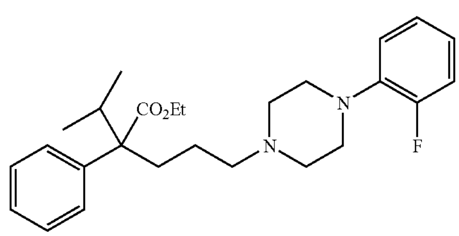 | 7.36-7.29 (m, 3H), 7.22-7.20 (m, 2H), 7.16 (d, J=8.0 Hz, 2H), 7.12-6.99 (m, 2H), 4.20 (q, J=7.1 Hz, 2H), 3.58 (s, 2H), 2.48-2.39 (m, 8H), 2.31-2.25 (m, 3H), 2.07-1.91 (m, 2H), 1.39-1.30 (m, 1H), 1.25 (t, J=7.1 Hz, 3H), 0.87 (d, J=6.7 Hz, 3H), 0.78 (d, J=6.9 Hz, 3H) |
| 25 | 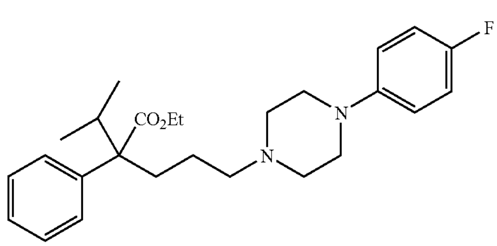 | 7.31-7.17 (m, 5H), 6.96-6.83 (m, 4H), 4.23-4.21 (m, 2H), 3.08 (t, J=4.9 Hz, 4H), 2.52-2.43 (m, 4H), 2.33 (t J=6.6 Hz, 2H), 2.12-1.96 (m, 2H), 1.42-1.41 (m, 1H), 1.27 (t, J=7.1 Hz, 3H), 0.88 (d, J=6.8 Hz, 3H), 0.80 (d, J=6.8 Hz, 3H) |

TABLE 1-continued

| Embodiment | Structure | NMR |
|---|---|---|
| 26 | 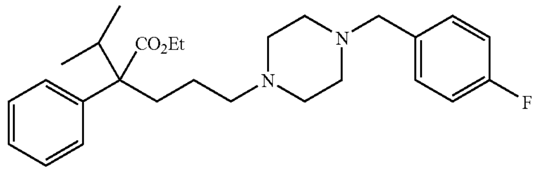 | 7.29-7.20 (m, 4H), 7.16 (d, J=7.6 Hz, 3H), 7.00-6.95 (m, 2H), 4.20 (q, J=7.0 Hz, 2H), 3.44 (s, 2H), 2.58-2.28 (m, 1H), 2.14-1.88 (m, 2H), 1.39-1.38 (m, 1H), 1.25 (t, J=7.1 Hz, 3H), 0.86 (d, J=6.6 Hz, 3H), 0.78 (d, J=6.7 Hz, 3H) |
| 27 | 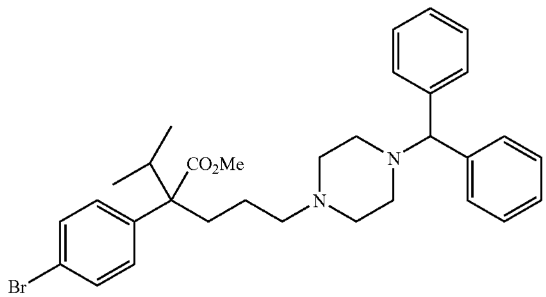 | 13.75 (s, 1H), 13.04 (s, 1H), 7.86 (d, J=6.9 Hz, 4H), 7.48-7.34 (m, 8H), 7.01 (d, J=8.6 Hz, 2H), 4.94 (s, 1H), 4.21 (bs, 2H), 3.95-3.92 (m, 2H), 3.73 (s, 3H), 3.49-3.42 (m, 1H), 3.25 (d, J=7.0 Hz, 1H), 3.20 (s, 1H), 3.01 (m, 2H), 2.37-2.26 (m, 2H), 1.84-1.70 (m, 4H), 1.33-1.24 (m, 2H), 4.24 (s, 4H), 0.92 (d, J=6.7 Hz, 3H), 0.80 (d, J=6.8 Hz, 3H) |
| 28 | 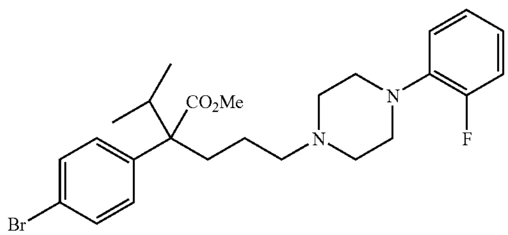 | 12.70 (s, 1H), 7.47 (d, J=8.5 Hz, 2H), 7.08 (d, J=8.6 Hz, 3H), 7.05-6.95 (m, 3H), 3.79 (s, 3H), 3.69-3.62 (m, 2H), 3.52 (d, J=12.0 Hz, 1H), 3.42-3.37 (m, 3H), 2.98-2.88 (m, 4H), 2.41-2.38 (m, 1H), 2.20-1.91 (m, 2H), 1.79 (m, 1H), 1.58-1.51 (m, 2H), 0.93 (d, J=6.7 Hz, 3 H_, 0.83 (d, J=6.8 Hz, 3H) |
| 29 | 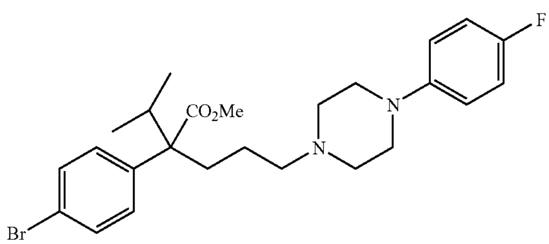 | 13.10 (s, 1H), 7.73 (m, 2H), 7.45 (dd, J=9.5, 2.7 Hz, 2H), 7.20-7.10 (m, 2H), 7.07 (dd, J=6.7, 2.0 Hz, 2H), 4.60-4.57 (m, 2H), 3.88-3.83 (m, 2H), 3.78 (s, 3H), 3.68 (d, J=12.0 Hz, 1H), 3.55 (t, J=14.5 Hz, 2H), 3.45 (d, J=12.2 Hz, 1H), 3.04-3.00 (m, 2H), 2.40-2.33 (m, 2H), 1.88-1.79 (m, 2H), 1.41 (m, 1H), 0.96 (d, J=6.7 Hz, 3H), 0.83 (d, J=6.8 Hz, 3H) |
| 30 | 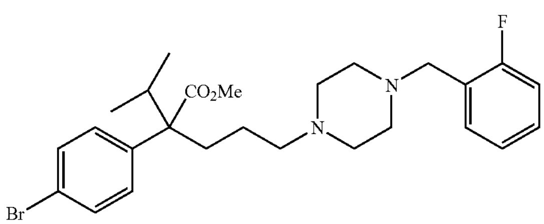 | 13.65 (bs, 1H), 13.25 (s, 1H), 7.87-7.83 (m, 1H), 7.50-7.47 (m, 1H), 7.44 (dd, J=6.8, 1.8 Hz, 2H), 7.31-7.28 (m, 1H), 7.19-7.14 (m, 1H), 7.04 (dd, J=6.8, 1.8 Hz, 2H), 4.31 (s, 2H), 4.05-4.02 (m, 2H), 3.90 (m, 2H), 3.76 (s, 3H), 3.58 (d, J=7.6 Hz, 1H), 3.48 (t, J=13.0 Hz, 2H), 3.46 (d, J=8.8 Hz, 1H), 3.20 (s, 3H), 3.03-2.99 (m, 2H), 2.36-2.24 (m, 3H), 1.83-1.71 (m, 2H), 1.37-1.34 (m, 1H), 1.18 (s, 5H), 0.92 (d, J=6.7 Hz, 3H), 0.81 (d, J=6.8 Hz, 3H) |
| 31 | 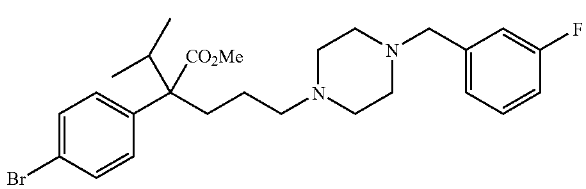 | 13.64 (s, 1H), 13.14 (s, 1H), 7.49-7.38 (m, 5H), 7.18-7.11 (m, 1H), 7.05-7.02 (m, 2H), 4.29 (s, 2H), 4.08-4.05 (m, 2H), 4.02-4.00 (m, 2H), 3.75 (s, 3H), 3.59 (d, J=12.5 Hz, 1H), 3.57-3.38 (m, 3H), 3.03-3.01 (m, 2H), 2.36-2.25 (m, 2H), 1.85-1.72 (m, 1H), 1.37-1.36 (m, 1H), 0.92 (d, J=6.7 Hz, 3H), 0.80 (d, J=6.8 Hz, 3H) |

TABLE 1-continued

| Embodiment | Structure | NMR |
|---|---|---|
| 32 | 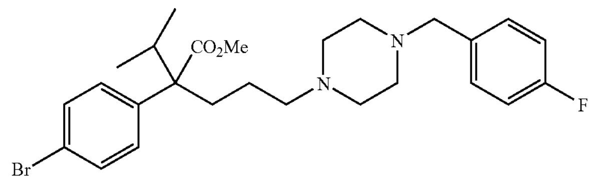 | 13.64 (s, 1H), 13.19 (s, 1H), 7.67 (dd, J=8.4, 5.1 Hz, 2H), 7.44 (d, J=8.5 Hz, 2H), 7.13 (t, J=8.5 Hz, 2H), 7.03 (d, J=8.6 Hz, 2H), 4.23 (s, 2H), 4.08-4.02 (m, 2H), 3.99-3.88 (m, 2H), 3.75 (s, 3H), 3.58 (d, J=12.3 Hz, 1H), 3.41 (t, J=12.1 Hz, 3H), 3.01-2.98 (m, 2H), 1.82-1.71 (m, 2H), 1.36-1.35 (m, 1H), 0.92 (d, J=6.7 Hz, 3H), 0.80 (d, J=6.8 Hz, 3H) |
| 33 | 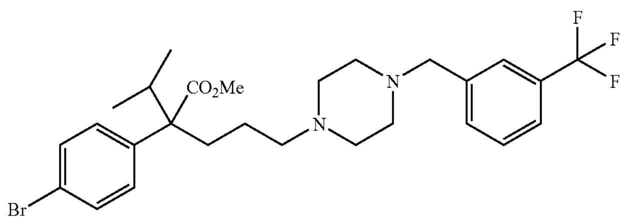 | 13.76 (bs, 1H), 13.09 (s, 1H), 8.03 (d, J=7.7 Hz, 1H), 7.94 (s, 1H), 7.73 (d, J=7.7 Hz, 1H), 7.62 (t, J=7.8 Hz, 1H), 7.43 (d, J=8.6 Hz, 2H), 7.03 (d, J=8.6 Hz, 2H), 4.40 (s, 2H), 4.10-4.04 (m, 2H), 3.94-3.90 (m, 2H), 3.75 (s, 3H), 3.60 (d, J=12.4 Hz, 1H), 3.49-3.40 (m, 3H), 3.01 (m, 2H), 2.37-2.25 (m, 2H), 1.82-1.72 (m, 2H), 1.38-1.36 (m, 1H), 0.91 (d, J=6.7 Hz, 3H), 0.80 (d, J=6.7 Jz, 3H) |
| 34 | 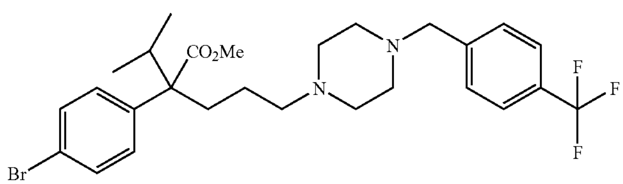 | 13.99 (s, 1H), 13.23 (s, 1H), 7.87 (d, J=7.8 Hz, 2H), 7.74 (d, J=7.8 Hz, 2H), 7.45 (d, J=8.4 Hz, 2H), 7.02 (d, J=8.6 Hz, 2H), 4.30 (s, 2H), 4.12-4.09 (m, 2H), 3.91-3.81 (m, 2H), 3.76 (s, 3H), 3.4 H (d, J=4.3 Hz, 1H), 3.39 (dd, J=25.3, 11.9 Hz, 3H), 3.01-2.92 (m, 2H), 2.38-2.30 (m, 2H), 1.83-1.70 (m, 6H), 1.34 (m, 1H), 1.25 (s, 1H), 0.94 (d, J=6.7 Hz, 3H), 0.82 (d, J=6.7 Hz, 3H) |
| 35 | 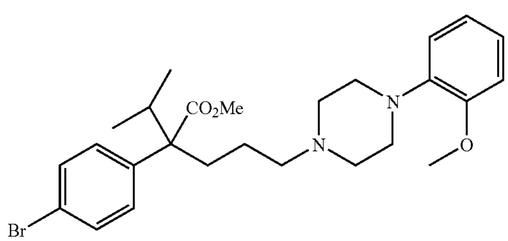 | 13.39 (s, 1H), 7.46 (d, J=8.6 Hz, 2H), 7.40 (t, J=7.6 Hz, 1H), 7.06 (dd, J=12.5, 8.5 Hz, 4H), 4.84 (bs, 1H), 4.25-4.08 (m, 1H), 4.03 (s, 3H), 3.79 (s, 3H), 3.56-3.49 (m, 3H), 3.40 (d, J=12.6 Hz, 1H), 3.03 (m, 2H), 2.40-2.24 (m, 2H), 1.94-1.78 (m, 2H), 1.49-1.78 (m, 2H), 0.94 (d, J=6.7 Hz, 3H), 0.83 (d, J=6.7 Hz, 3H) |
| 36 | 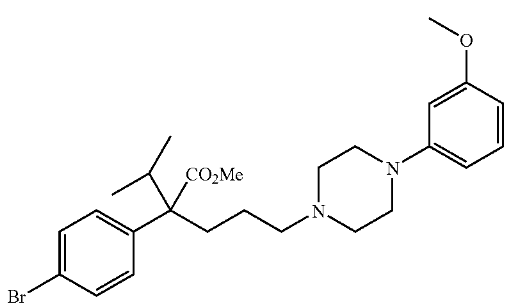 | 13.20 (s, 1H), 7.46 (d, J=8.6 Hz, 2H), 7.38 (t, J=8.2 Hz, 1H), 7.31 (bs, 1H), 7.07 (d, J=8.6 Hz, 2H), 6.92 (dd, J=8.3 Hz, 1.7 Hz, 1H), 4.61-4.58 (m, 2H), 4.01-3.89 (m, 2H), 3.83 (s, 3H), 3.78 (s, 3H), 3.63 (dd, J=28.3, 13.4 Hz, 3H), 3.43 (d, J=12.2 Hz, 1H), 3.04 (bs, 2H), 2.41-2.32 (m, 2H), 1.91-1.79 (m, 2H), 1.42-1.40 (m, 1H), 0.96 (d, J=6.7 Hz, 3H), 0.84 (d, J=6.7 Hz, 3H) |
| 37 | 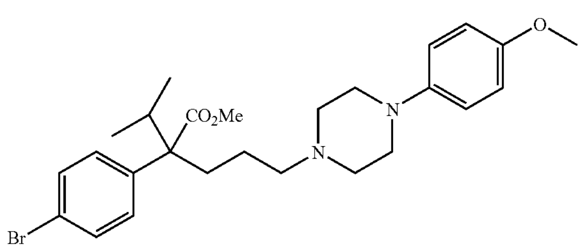 | 13.10 (s, 1H), 7.79 (d, J=8.8 Hz, 2H), 7.46 (d, J=8.4 Hz, 2H), 7.06 (d, J=8.4 Hz, 2H), 6.97 (d, J=8.9 Hz, 2H), 4.74-4.68 (m, 2H), 4.14 (bs, 2H), 3.82 (s, 3H), 3.78 (s, 3H), 3.65 (d, J=12.7 Hz, 1H), 3.57 (t, J=14.0 Hz, 2H), 3.44 (d, J=12.0 Hz, 1H), 3.07 (bs, 2H), 2.40-2.34 (m, 2H), 2.03-1.78 (m, 2H), 1.60-1.41 (m, 1H), 1.29-1.24 (m, 1H), 0.96 (d, J=6.7 Hz, 3H), 0.83 (d, J=6.7 Hz, 3H) |

TABLE 1-continued

| Embodiment | Structure | NMR |
|---|---|---|
| 38 | 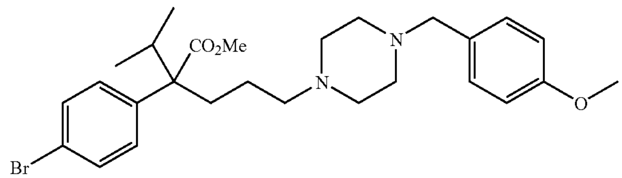 | 13.41 (s, 1H), 13.18 (s, 1H), 7.55 (d, J=8.6 Hz, 2H), 7.45 (d, J=8.6 Hz, 2H), 7.04 (d, J=8.6 Hz, 2H), 6.95 (d, J=8.6 Hz, 2H), 4.16 (s, 2H), 3.81 (s, 3H), 3.76 (s, 3H), 3.56 (d, J=10.0 Hz, 1H), 3.43-3.32 (m, 3H), 3.01 (bs, 2H), 2.37-2.27 (m, 2H), 1.84-1.73 (m, 5H), 1.42-1.25 (m, 2H), 0.93 (d, J=6.7 Hz, 3H), 0.81 (d, J=6.7 Hz, 3H) |
| 39 | 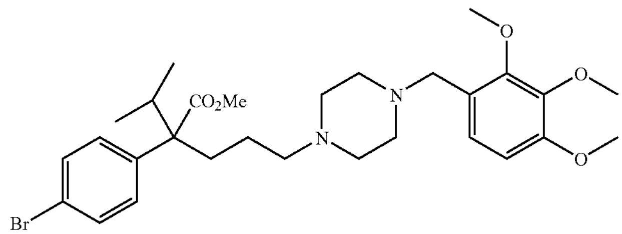 | 13.29 (s, 1H), 13.13 (s, 1H), 7.43 (dd, J=11.8, 8.6 Hz, 3H), 7.03 (d, J=8.6 Hz, 2H), 6.72 (d, J=8.6 Hz, 1H), 4.19 (m, 2H), 3.97 (s, 3H), 3.96 (s, 3H), 3.84 (s, 3H), 3.76 (s, 3H), 3.48 (d, J=9.9 Hz, 1H), 3.44-3.38 (m, 2H), 3.32 (d, J=10.3 Hz, 1H), 2.97 (bs, 2H), 2.36-2.22 (m, 2H), 1.86-1.72 (m, 4H), 1.38-1.24 (m, 2H), 0.92 (d, J=6.7 Hz, 3H), 0.80 (d, J=6.8 Hz, 3H) |
| 40 | 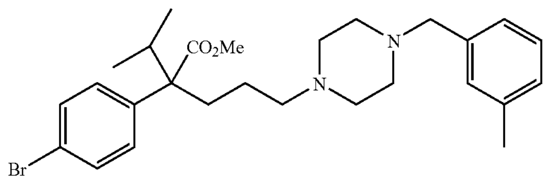 | 13.44 (s, 1H), 13.13 (s, 1H), 7.44 (d, J=8.4 Hz, 4H), 7.33 (t, J=7.5 Hz, 1H), 7.22 (bs, 1H), 7.03 (d, J=8.5 Hz, 2H), 4.18 (s, 2H), 3.95-3.91 (m, 4H), 3.75 (s, 3H), 3.56 (d, J=10.3 Hz, 1H), 3.47-3.33 (m, 3H), 3.01-2.99 (m, 2H), 2.37 (s, 3H), 2.34-2.25 (m, 2H), 2.11 (bs, 1H), 1.85-1.69 (m, 2H), 1.36-1.33 (m, 1H), 0.92 (d, J=6.7 Hz, 3H), 0.80 (d, J=6.7 Hz, 3H) |
| 41 | 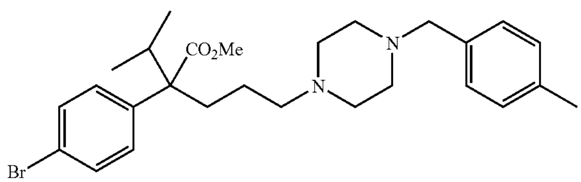 | 13.39 (s, 1H), 13.11 (s, 1H), 7.50 (d, J=7.9 Hz, 2H), 7.44 (d, J=8.6 Hz, 2H), 7.24 (d, J=7.8 Hz, 2H), 7.03 (d, J=Hz, 2H), 4.19 (s, 2H), 3.95-3.90 (m, 4H), 3.11 (s, 3H), 3.56 (d, J=10.8 Hz, 1H), 3.44-3.34 (m, 3H), 3.01-2.99 (m, 2H), 2.36 (s, 3H), 1.84-1.71 (m, 2H), 1.37-1.35 (m, 1H), 0.92 (d, J=6.7 Hz, 3H), 0.80 (d, J=6.8 Hz, 3H) |
| 42 | 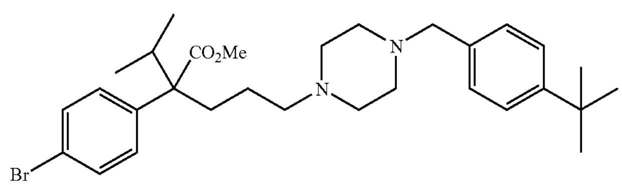 | 13.50 (s, 1H), 13.24 (s, 1H), 7.55 (d J=8.3 Hz, 2H), 7.47-7.43 (m, 4H), 7.04 (d, J=8.6 Hz, 2H), 4.18 (s, 2H), 3.96-3.95 (m, 4H), 3.57 (d, J=8.3 Hz, 1H), 3.42 (t, J=12.0 Hz, 2H), 3.30 (d, J=10.0 Hz, 1H), 2.98 (bs, 2H), 2.39-2.31 (m, 2H), 1.86-1.78 (m, 1H), 1.71 (s, 5H), 1.31 (s, 9H), 0.94 (d, J=6.7 Hz, 3H), 0.82 (d, J=6.8 Hz, 3H) |
| 43 | 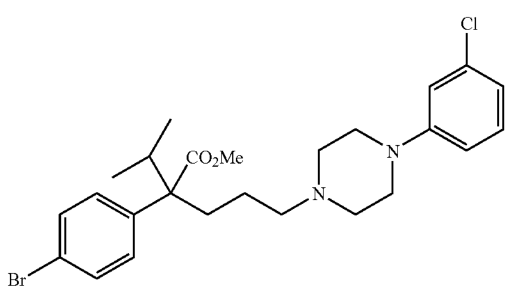 | 13.01 (s, 1H), 7.46 (d, J=8.5 Hz, 2H), 7.29 t, J=8.1 Hz, 1H), 7.23 (s, 1H), 7.12-7.10 (m, 2H), 7.05 (d, J=7.5 Hz, 2H), 4.07 (t, J=12.0 Hz, 2H), 3.79 (s, 3H), 3.61-3.55 (m, 3H), 3.46 (d, J=16.8 Hz, 1H), 3.31-3.28 (m, 2H), 2.97 (bs, 2H), 2.42-2.24 (m, 2H), 1.94-1.78 (m, 2H), 1.49-1.47 (m, 1H), 0.94 (d, J=6.7 Hz, 3H), 0.83 (d, J=6.7 Hz, 3H) |
| 44 | 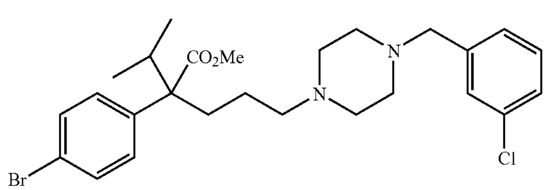 | 13.78 (bs, 1H), 13.18 (s, 1H), 7.66-7.64 (m, 2H), 7.46-7.36 (m, 4H), 7.04 (d, J=8.6 Hz, 2H), 4.24 (s, 2H), 4.06-3.91 (m, 4H), 3.76 (s, 3H), 3.59 (d, J=11.2 Hz, 1H), 3.48-3.35 (m, 3H), 3.00 (m, 2H), 2.38-2.28 (m, 2H), 1.85-1.78 (m, 4H), 1.36-1.33 (m, 1H), 0.93 (d, J=6.7 Hz, 3H), 0.82 (d, J=6.8 Hz, 3H) |

TABLE 1-continued

| Embodi-ment | Structure | NMR |
|---|---|---|
| 45 | 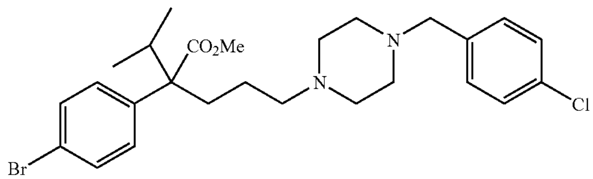 | 13.24 (bs, 1H), 12.58 (s, 1H), 7.63 (d, J=8.0 Hz, 2H), 7.45-7.41 (m, 4H), 7.04 (d, J=8.3 Hz, 2H), 4.21 (s, 2H), 3.98-3.80 (m, 2H), 3.75 (s, 3H), 3.62 (d, J=10.6 Hz, 1H), 3.48-3.44 (m, 6H), 3.03 (m, 2H), 2.38-2.25 (m, 2H), 1.84-1.71 (m, 2H), 1.43-1.37 (m, 1H), 0.92 (d, J=6.6 Hz, 3H), 0.80 (d, J=6.7 Hz, 3H) |
| 46 | 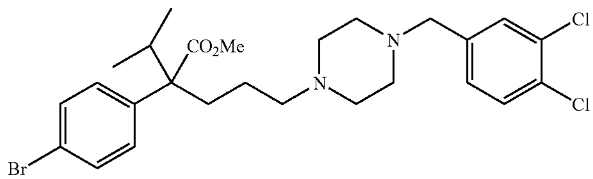 | 11.60 (s, 1H), 7.96 (s, 1H), 7.01 (d, J=8.1 Hz, 1H), 7.62-7.60 (m, 1H), 7.49 (d, J=8.5 Hz, 2H), 7.15 (d, J=8.5 Hz, 2H), 4.30 (s, 2H), 3.67 (s, 3H), 3.63-3.43 (m, 6H), 3.07 (m, 2H), 2.35-1.89 (m, 2H), 1.51-1.33 (m, 2H), 0.77 (d, J=6.6 Hz, 3H), 0.67 (d, J=6.5 Hz, 3H) |
| 47 | 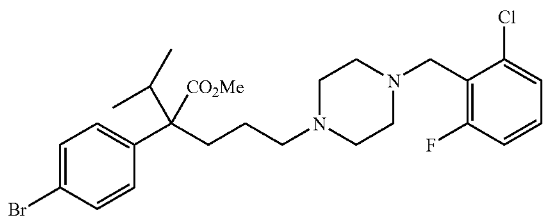 | 12.90 (s, 1H), 7.47-7.40 (m, 3H), 7.34 (d, J=8.1 Hz, 1H), 7.15-7.13 (m, 1H), 7.05 (d, J=8.6 Hz, 2H), 4.24 (s, 2H), 3.99-3.81 (m, 4H), 3.76 (s, 3H), 3.58-3.52 (m, 3H), 3.48 (d, J=2.0 Hz, 1H), 3.04-2.99 (m, 2H), 2.37-2.33 (m, 1H), 2.26-2.20 (m, 1H), 1.88-1.82 (m, 1H), 1.74-1.71 (m, 1H), 1.40-1.39 (m, 1H), 0.90 (d, J=6.7 Hz, 3H), 0.80 (d, J=6.8 Hz, 3H) |
| 48 | 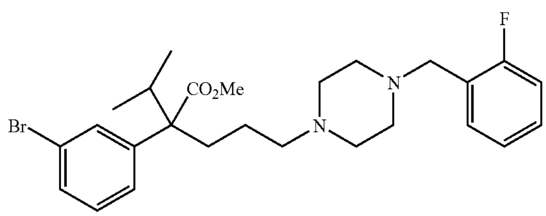 | 7.46-7.36 (m, 4H), 7.22-7.17 (m, 2H), 7.14 (d, J=8.2 Hz, 2H), 4.29 (s, 2H), 3.67 (d, J=27.7 Hz, 8H), 3.06-2.96 (m, 2H), 2.40-2.33 (m, 1H), 2.07-1.77 (m, 2H), 1.42-1.23 (m, 2H), 0.79 (d, J=6.7 Hz, 3H), 0.68 (d, J=6.7 Hz, 3H) |
| 49 | 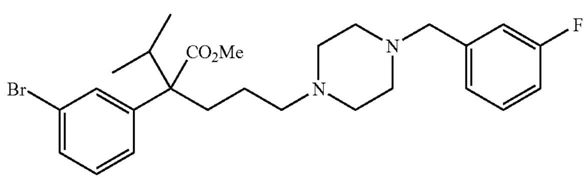 | 7.41-7.36 (m, 3H), 7.22-7.12 (m, 5H), 4.19 (s, 2H), 3.68 (s, 3H), 3.33 (bs, 8H), 3.07-2.94 (m, 2H), 2.41-2.34 (m, 1H), 2.06-1.78 (m, 2H), 1.40-1.12 (m, 2H), 0.68 (d, J=6.7 Hz, 3H), 0.63 (d, J=6.5 Hz, 3H) |
| 50 | 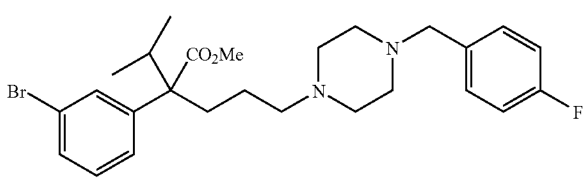 | 7.41 (dd, J=8.7, 5.3 Hz, 2H), 7.23-7.11 (m, 4H), 7.05-6.98 (m, 2H), 4.31 (s, 2H), 3.68 (s, 3H), 3.54-3.41 (m, 8H), 3.08-3.01 (m, 2H), 2.41-2.36 (m, 1H), 2.05-2.00 (m, 1H), 1.87-1.83 (m, 1H), 1.43-1.26 (m, 2H), 0.78 (d, J=6.8 Hz, 3H), 0.67 (d, J=6.7 Hz, 3H) |
| 51 | 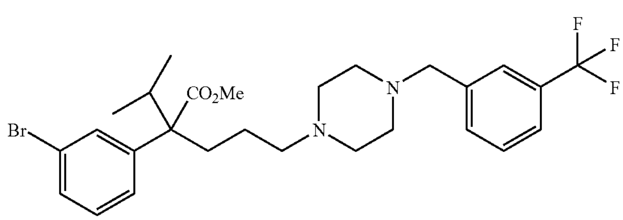 | 7.41-7.36 (m, 3H), 7.21 (dd, J=7.7, 2.6 Hz, 1H), 7.17-7.08 (m, 4H), 4.19 (s, 2H), 3.67 (s, 3H), 3.32 (bs, 8H), 3.08-2.99 (m, 2H), 2.38-2.35 (m, 1H), 2.05-1.78 (m, 2H), 1.40-1.12 (m, 2H), 0.78 (d, J=6.5 Hz, 3H), 0.68 (d, J=6.6 Hz, 3H) |
| 52 | 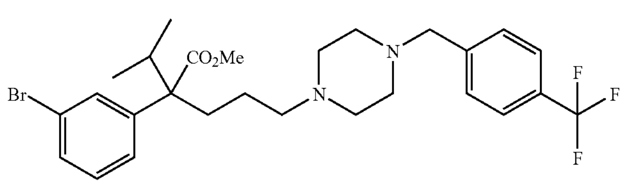 | 9.43 (s, 2H), 7.87-7.80 (m, 4H), 7.45 (d, J=7.8 1H), 7.36-7.35 (m, 1H), 7.29 (t, J=7.9 Hz, 2H), 7.19 (d, J=8.0 Hz, 1H), 4.43 (s, 2H), 3.69 (s, 3H), 3.64-3.41 (m, 8H), 3.09 (m, 3H), 2.39-2.35 (m, 1H), 2.07-1.89 (m, 2H), 1.52-1.26 (m, 2H), 0.79 (d J=6.6 Hz, 3H), 0.70 (d, J=6.7 Hz, 3H) |

TABLE 1-continued

| Embodiment | Structure | NMR |
|---|---|---|
| 53 | 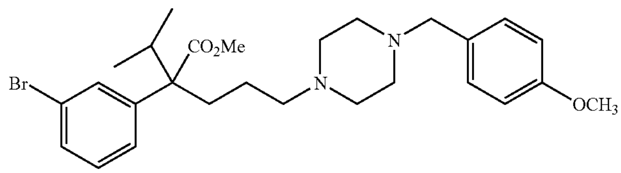 | 7.40 (dd, J=7.8, 1.0 Hz, 1H), 7.38 (t, J=1.6 Hz, 1H), 7.30 (d, J=8.7 Hz, 2H), 7.24-7.13 (m, 2H), 6.95 (d, J=8.7 Hz, 2H), 4.17 (s, 2H), 3.73 (s, 3H), 3.67 (s, 3H), 3.33 (bs, 8H), 3.02-2.92 (m, 2H), 2.38-2.33 (m, 1H), 2.05-1.77 (m, 2H), 1.38-1.21 (m, 2H), 0.78 (d, J=6.7 Hz, 3H), 0.67 (d, J=6.7 Hz, 3H) |
| 54 | 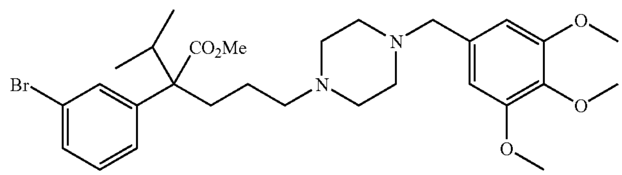 | 7.41-7.38 (m, 2H), 7.19 (t, J=7.7 Hz, 1H), 7.14 (d, J=7.5 Hz, 1H), 7.05 (d, J=8.7 Hz, 1H), 6.80 (d, J=8.7 Hz, 1H), 4.09 (s, 2H), 3.80 (s, 3H), 3.77 (s, 3H), 3.75 (s, 3H), 3.67 (s, 3H), 3.22 (bs, 6H), 2.94-2.86 (m, 2H), 2.39-2.33 (m, 1H), 2.01-1.78 (m, 2H), 1.38-1.22 (m, 2H), 0.78 (d, J=6.7 Hz, 3H), 0.67 (d, J=6.7 Hz , 3H) |
| 55 | 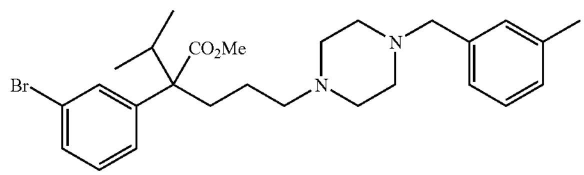 | 7.41-7.38 (m, 2H), 7.30-7.26 (m, 2H), 7.22-7.15 (m, 4H), 7.17 (dd, J=11.0, 4.0 Hz, 4H), 4.67 (s, 2H), 4.22 (s, 3H), 3.67 (bs, 8H), 3.01-2.81 (m, 2H), 2.24 (s, 3H), 2.05-2.00 (m, 1H), 1.84-1.78 (m, 1H), 1.38-1.24 (m, 2H), 0.79 (d, J=6.5 Hz, 3H), 0.68 (d, J=6.6 Hz, 3H) |
| 56 | 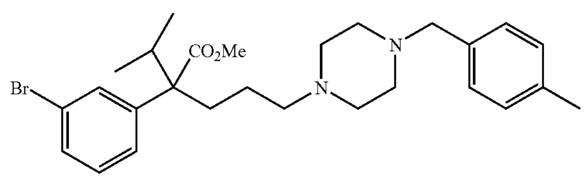 | 7.40 (d, J=7.8 Hz, 1H), 7.38 (m, 1H), 7.26-7.21 (m, 4H), 7.19 (d, J=7.8 Hz, 1H), 7.14 (d, J=8.0 Hz, 1H), 4.20 (s, 2H), 3.67 (s, 3H), 3.36 (bs, 8H), 3.04-2.96 (m, 2H), 2.40-2.34 (m, 1H), 2.24 (s, 3H), 2.06-1.77 (m, 2H), 1.41-1.25 (m, 2H), 0.79 (d, J=6.7 Hz, 3H), 0.68 (d, J=6.7 Hz, 3H) |
| 57 | 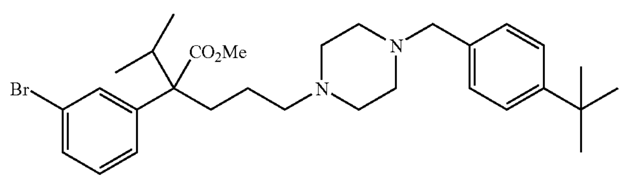 | 7.48 (d, J=8.2 Hz, 2H), 7.41-7.38 (m, 2H), 7.31 (d, J=8.2 Hz, 2H), 7.16 (dd, J=19.3, 7.8 Hz, 2H), 4.24 (s, 2H), 3.67 (s, 3H), 3.39 (bs, 8H), 3.06-2.97 (m, 2H), 2.39-2.34 (m, 1H), 2.05-1.77 (m, 2H), 1.41-1.24 (m, 2H), 1.19 (s, 9H), 0.79 (d, J=6.7 Hz, 3H), 0.68 (d, J=6.7 Hz, 3H) |
| 58 | 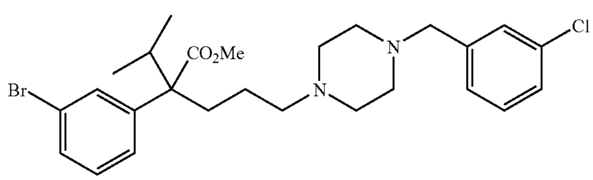 | 7.41-7.37 (m, 4H), 7.21-7.12 (m, 2H), 4.21 (s, 2H), 3.67 (s, 3H), 3.45 (s, 2H), 3.36 (bs, 8H), 3.04-2.86 (m, 2H), 2.38-2.35 (m, 1H), 2.05-1.77 (m, 2H), 1.39-1.22 (m, 2H), 0.73 (d, J=6.5 Hz, 3H), 0.68 (d, J=6.5 Hz, 3H) |
| 59 | 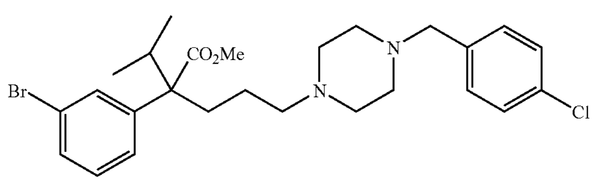 | 11.64 (s, 1H), 7.68-7.63 (m, 2H), 7.53-7.49 (m, 2H), 7.45 (d, J=7.9 Hz, 1H), 7.35 (s, 1H), 7.28 (t, J=7.9 Hz, 1H), 7.19 (d, J=7.9 Hz, 1H), 4.36-4.24 (m, 2H), 3.68 (s, 3H), 3.64-3.44 (m, 8H), 3.06 (s, 2H), 2.39-2.33 (m, 1H), 2.08-1.90 (m, 2H), 1.52-1.21 (m, 2H), 0.78 (d, J=6.6 Hz, 3H), 0.68 (d, J=6.8 Hz, 3H) |
| 60 | 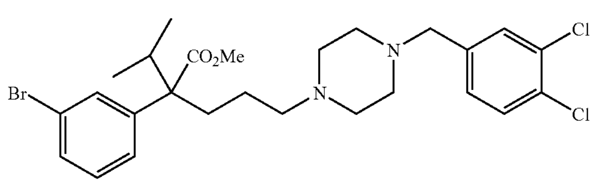 | 7.54-7.51 (m, 2H), 7.41-7.38 (m, 2H), 7.27 (dd, J=8.2, 2.0 Hz, 1H), 7.19 (t, J=7.8 Hz, 1H), 7.14 (d, J=8.0 Hz, 1H), 4.22 (s, 2H), 3.67 (s, 3H), 3.37 (bs, 8H), 3.05-2.97 (m, 2H), 2.38-2.33 (m, 1H), 2.05-1.77 (m, 2H), 1.42-1.23 (m, 2H), 0.79 (d, J=6.7 Hz, 3H), 0.68 (d, J=6.7 Hz, 3H) |

TABLE 1-continued

| Embodiment | Structure | NMR |
|---|---|---|
| 61 | 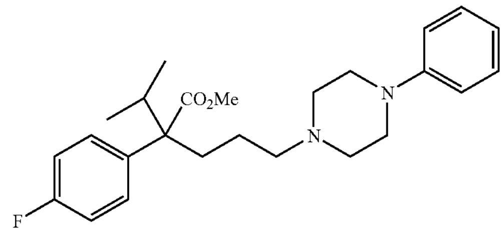 | 12.70 (s, 3H), 7.32-7.29 (m, 2H), 7.19-7.14 (m, 2H), 7.09-7.01 (m, 2H), 6.97-6.93 (m, 1H), 6.89-6.87 (m, 2H), 3.79 (s, 3H), 3.66-3.50 (m, 5H), 3.42 (d, J=11.7 Hz, 1H), 2.92-2.82 (m, 4H), 2.40-2.37 (m, 1H), 2.20-2.16 (m, 1H), 1.96-1.90 (m, 1H), 1.78-1.77 (m, 1H), 1.66 (s, 1H), 1.57-1.55 (m, 1H), 0.92 (d, J=6.8 Hz, 3H), 0.82 (d, J=6.8 Hz, 3H) |
| 62 | 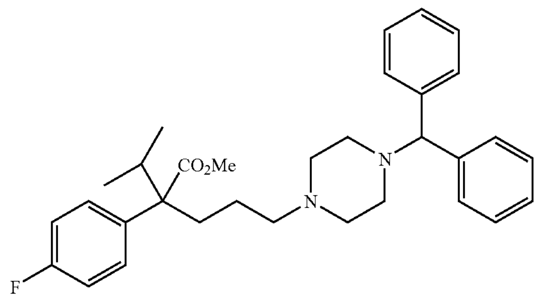 | 13.64 (s, 1H), 12.95 (s, 1H), 7.86 (d, J=6.3 Hz, 4H), 7.46-7.35 (m, 6H), 7.12-7.08 (m, 2H), 7.02-6.97 (m, 2H), 4.93 (s, 1H), 4.25-4.23 (m, 2H), 3.98-3.93 (m, 2H), 3.75 (s, 3H), 3.32 (d, J=12.3 Hz, 1H), 3.00-2.96 (m, 2H), 2.37-2.26 (m, 2H), 1.82-1.73 (m, 5H), 1.34-1.25 (m, 1H), 0.92 (d, J=6.8 Hz, 3H), 0.81 (d, J=6.8 Hz, 3H) |
| 63 | 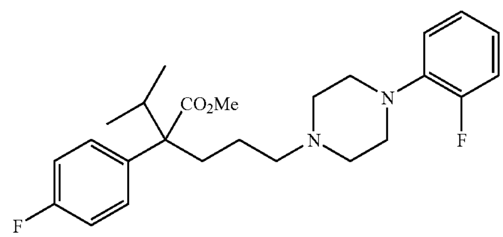 | 7.19 (dd, J=8.6, 3.3 Hz, 2H), 7.08-7.01 (m, 6H), 3.68 (s, 3H), 3.49-3.43 (s, 4H), 3.07-2.95 (m, 6H), 2.42-2.36 (m, 1H), 2.08-1.82 (m, 2H), 1.44-1.28 (m, 2H), 0.79 (d, J=6.6 Hz, 3H), 0.68 (d, J=6.6 Hz, 3H) |
| 64 | 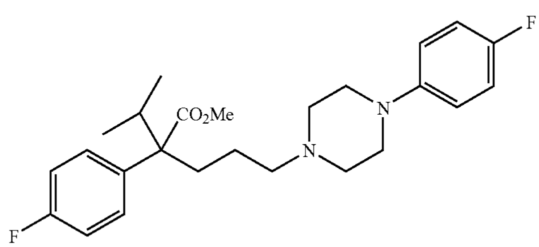 | 11.11 (s, 1H), 7.23 (dd, J=8.8, 3.4 Hz, 2H), 7.18-7.02 (m, 4H), 6.98 (dd, J=9.1, 4.5 Hz, 2H), 3.68 (s, 3H), 3.64 (d, J=12.5 Hz, 2H), 3.40 (d, J=11.0 Hz, 2H), 3.14-3.00 (m, 6H), 2.40-2.37 (m, 1H), 2.05-1.89 (m, 2H), 1.59-1.35 (m, 2H), 0.79 (d, J=6.6 Hz, 3H), 0.69 (d, J=6.7 Hz, 3H) |
| 65 | 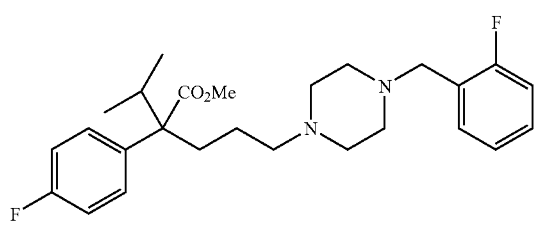 | 7.40 (dd, J=14.8, 7.2 Hz, 1H), 7.20-7.14 (m, 5H), 7.01 (t, J=8.8 Hz, 2H), 4.30 (s, 2H), 3.66 (s, 3H), 3.46-3.40 (m, 8H), 3.09-3.00 (m, 2H), 2.39-2.33 (m, 1H), 2.05-1.98 (m, 2H), 1.41-1.25 (m, 2H), 0.77 (d, J=6.7 Hz, 3H), 0.66 (d, J=6.7 Hz, 3H) |
| 66 | 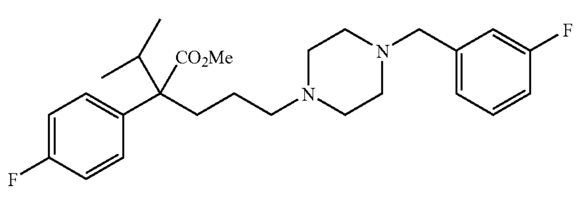 | 13.69 (bs, 1H), 13.26 (s, 1H), 7.84 (t, J=7.3 Hz, 1H), 7.47 (dd, J=14.0, 6.7 Hz, 1H), 7.29 (d, J=7.6 Hz, 1H), 7.17 (d, J=8.9 Hz, 1H), 7.19-7.13 (m, 2H), 7.00 (t, J=8.5 Hz, 2H), 4.30 (s, 2H), 4.06-4.01 (m, 2H), 3.90 (m, 2H), 3.76 (s, 3H), 3.58 (d, J=12.2 Hz, 1H), 3.51-3.40 (m, 3H), 3.03-2.95 (m, 2H), 2.37-2.24 (m, 2H), 1.37-1.34 (m, 1H), 0.91 (d, J=6.7 Hz, 3H), 0.80 (d, J=6.7 Hz, 3H) |

TABLE 1-continued

| Embodiment | Structure | NMR |
|---|---|---|
| 67 | 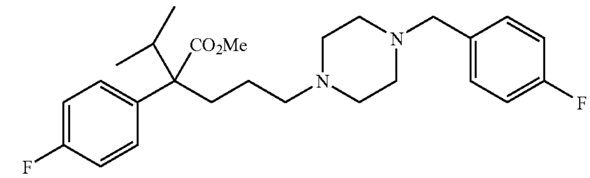 | 7.43-7.41 (m, 4H), 7.22-7.15 (m, 4H), 4.30 (s, 2H), 3.70 (s, 3H), 3.52-3.44 (m, 8H), 3.09-3.07 (m, 2H), 2.39 (m, 1H), 2.06-2.04 (m, 1H), 1.84-1.81 (m, 1H), 1.45-1.28 (m, 2H), 0.80 (d, J=5.3 Hz, 3H), 0.69 (d, J=5.4 Hz, 3H) |
| 68 | 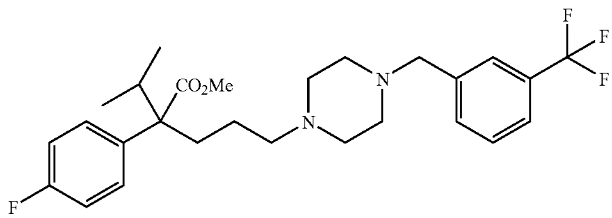 | 7.77-7.73 (m, 2H), 7.62 (dd, J=11.6, 7.7 Hz, 2H), 7.19-7.15 (m, 2H), 7.05-7.00 (m, 2H), 4.41 (s, 2H), 3.67 (s, 3H), 3.09-3.00 (m, 2H), 2.40-2.34 (m, 1H), 2.06-1.80 (m, 2H), 1.43-1.26 (m, 2H), 0.78 (d, J=6.6 Hz, 3H), 0.67 (d, J=6.7 Hz, 3H) |
| 69 | 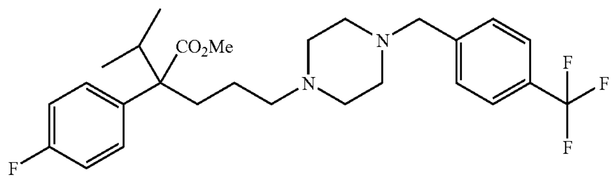 | 13.70 (s, 1H), 12.99 (s, 1H), 7.90 (d, J=8.1 Hz, 2H), 7.72 (d, J=8.1 Hz, 2H), 7.12 (dd, J=8.9, 5.2 Hz, 2H), 7.04-6.99 (m, 2H), 4.40 (s, 2H), 4.15-4.05 (m, 2H), 3.93 (s, 2H), 3.75 (s, 3H), 3.64 (d, J=12.5 Hz, 1H), 3.53-3.45 (m, 3H), 3.07-3.01 (m, 2H), 2.38-2.26 (m, 2H), 1.82-1.73 (m, 1H), 1.40-1.38 (m, 1H), 0.91 (d, J=6.7 Hz, 3H), 0.80 (d, J=6.8 Hz, 3H) |
| 70 | 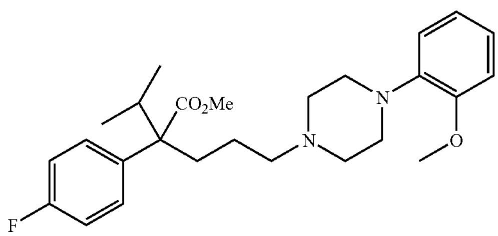 | 13.73 (s, 1H), 7.43 (s, 1H), 7.24-7.20 (m, 1H), 7.16 (dd, J=8.8, 5.3 Hz, 2H), 7.05-6.94 (m, 4H), 4.12-4.06 (m, 1H), 3.97 (s, 3H), 3.79 (s, 3H), 3.52-3.42 (m, 6H), 2.99-2.88 (m, 2H), 2.40-2.26 (m, 1H), 2.23-2.20 (m, 1H), 1.96-1.88 (m, 1H), 1.80-1.78 (m, 1H), 1.55-1.51 (m, 1H), 0.92 (d, J=6.7 Hz, 3H), 0.82 (d, J=6.8 Hz, 3H) |
| 71 | 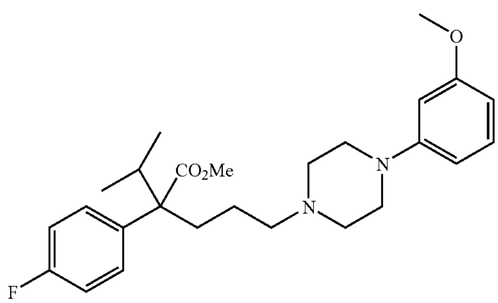 | 12.82 (s, 1H), 7.31-7.26 (m, 1H), 7.16 (dd, J=8.7, 5.3 Hz, 2H), 7.05-7.01 (m, 2H), 6.92 (s, 2H), 6.74 (d, J=7.7 Hz, 1H), 4.27-4.09 (m, 2H), 3.80 (s, 3H), 3.79 (s, 3H), 3.73-3.68 (m, 3H), 3.47 (s, 2H), 3.01 (m, 2H), 2.40-2.35 (m, 1H), 2.32-2.24 (m, 1H), 1.94-1.78 (m, 2H), 1.49-1.48 (m, 1H), 0.93 (d, J=6.8 Hz, 3H), 0.82 (d, J=6.7 Hz, 3H) |
| 72 | 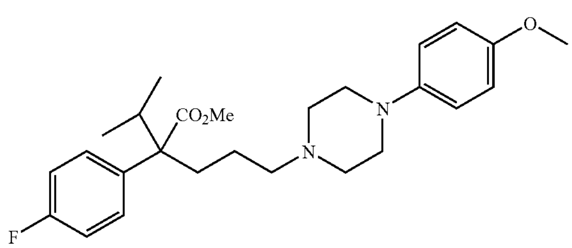 | 12.73 (s, 1H), 7.55 (s, 2H), 7.16 (dd, J=8.9, 5.3 Hz, 2H), 7.05-7.01 (m, 2H), 6.93 (d, J=8.0 Hz, 2H), 4.43 (s, 2H), 3.81 (s, 3H), 3.79 (s, 3H), 3.70 (d, J=9.5 Hz, 3H), 3.57-3.52 (m, 3H), 3.08-3.04 (m, 2H), 2.40-2.29 (m, 2H), 1.92-1.77 (m, 2H), 1.46-1.44 (m, 1H), 0.94 (d, J=6.7 Hz, 3H), 0.83 (d, J=6.8 Hz, 3H) |
| 73 | 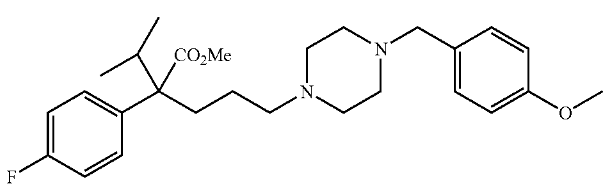 | 12.85 (s, 1H), 7.57 (d, J=8.6 Hz, 2H), 7.13 (dd, J=8.7, 5.3 Hz, 2H), 7.06-7.01 (m, 2H), 6.94 (d, J=8.7 Hz, 2H), 4.24 (s, 2H), 3.99-3.89 (m, 4H), 3.81 (s, 3H), 3.76 (s, 3H), 3.61 (d, J=9.9 Hz, 1H), 3.50-3.45 (m, 3H), 3.08-3.01 (m, 2H), 2.36-2.24 (m, 2H), 1.83-1.73 (m, 2H), 1.42-1.38 (m, 1H), 0.91 (d, J=6.7 Hz, 3H), 0.80 (d, J=6.8 Hz, 3H) |

TABLE 1-continued

| Embodiment | Structure | NMR |
|---|---|---|
| 74 | 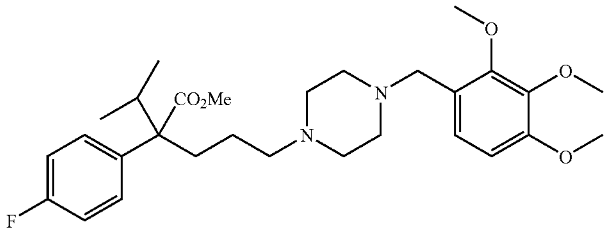 | 12.73 (s, 1H), 12.61 (s, 1H), 7.42 (d, J=8.7 Hz, 1H), 7.13 (dd, J=8.8. 5.2 Hz, 2H), 7.03-6.99 (m, 2H), 6.73 (d, J=8.7 Hz, 1H), 4.23 (s, 2H), 3.98 (s, 6H), 3.87 (s, 3H), 3.85 (s, 3H), 3.77 (s, 3H), 3.58 (d, J=9.7 Hz, 2H), 3.52-3.44 (m, 3H), 3.05-3.03 (m, 2H), 2.37-2.34 (m, 1H), 2.25-2.21 (m, 1H), 1.85-1.73 (m, 2H), 1.42 (m, 1H), 0.91 (d, J=6.7 Hz, 3H), 0.80 (d, J=6.8 Hz, 3H) |
| 75 | 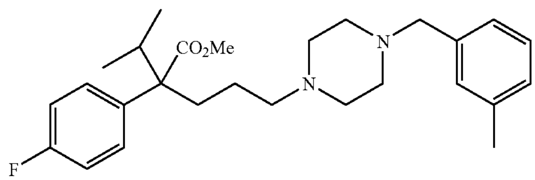 | 12.63 (s, 1H), 7.47-7.46 (m, 1H), 7.34-7.29 (m, 1H), 7.23 (d, J=8.8 Hz, 1H), 7.13 (dd, J=8.9, 5.2 Hz, 2H), 7.03-6.99 (m, 2H), 4.27 (s, 2H), 4.02-3.94 (m, 4H), 3.76 (s, 3H), 3.63 (d, J=9.5 Hz, 1H), 3.53-3.50 (m, 3H), 3.11-3.03 (m, 2H), 2.37 (s, 3H), 2.33-2.23 (m, 1H), 1.83-1.73 (m, 2H), 1.40-1.37 (m, 1H), 0.91 (d, J=6.8 Hz, 3H), 0.80 (d, J=6.8 Hz, 3H) |
| 76 | 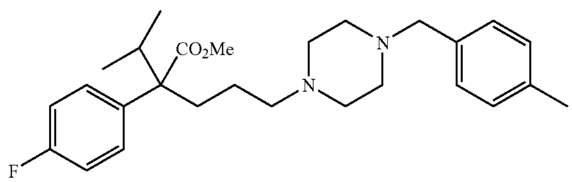 | 12.74 (bs, 1H), 7.54 (d, J=7.6 Hz, 2H), 7.23 (d, J=7.8 Hz, 2H), 7.13 (dd, J=8.7, 5.3 Hz, 2H), 7.03-6.99 (m, 2H), 4.31 (s, 2H), 3.99-3.94 (m, 6H), 3.75 (s, 3H), 3.71-3.51 (m, 5H), 3.11-3.08 (m, 2H), 2.35 (s, 4H), 2.28-2.22 (m, 1H), 1.88-1.81 (m, 2H), 1.42 (m, 1H), 0.90 (d, J=6.8 Hz, 3H), 0.79 (d, J=6.7 Hz, 3H) |
| 77 | 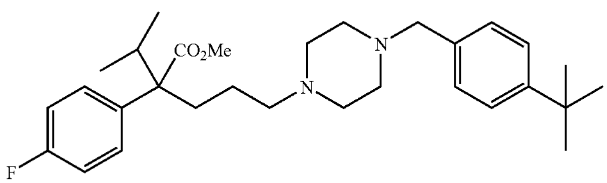 | 7.57 (d, J=8.2 Hz, 2H), 7.45 (d, J=8.2 Hz, 2H), 7.13 (dd, J=8.8, 5.3 Hz, 2H), 7.03-6.99 (m, 2H), 4.27 (s, 2H), 3.95-3.90 (m, 4H), 3.76 (s, 3H), 3.60-3.48 (m, 4H), 3.10-3.03 (m, 2H), 2.37-2.22 (m, 2H), 1.86-1.72 (m, 2H), 1.30 (s, 9H), 0.91 (d, J=6.7 Hz, 3H), 0.80 (d, J=6.8 Hz, 3H) |
| 78 | 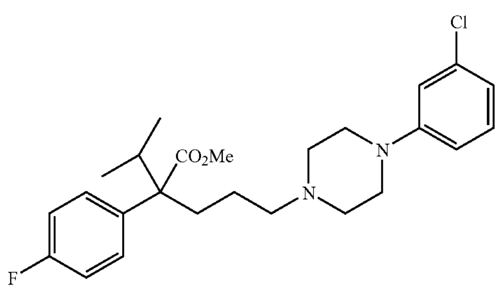 | 11.06 (s, 1H), 7.25-7.21 (m, 3H), 7.16-7.12 (m, 2H), 7.01-7.00 (m, 1H), 6.90 (dd, J=8.4, 1.9 Hz, 1H), 6.84 (dd, J=7.9, 1.4 Hz, 1H), 3.92 (s, 3H), 3.82 (d, J=13.2 Hz, 2H), 3.69 (s, 3H), 3.39 (d, J=11.4 Hz, 2H), 3.17 (t, J=12.3 Hz, 2H), 3.08-3.03 (m, 4H), 2.49-2.48 (m, 1H), 2.05-1.92 (m, 2H), 1.57-1.56 (m, 1H), 1.38-1.20 (m, 2H), 0.79 (d, J=6.7 Hz, 3H), 0.70 (d, J=6.6 Hz, 3H) |
| 79 | 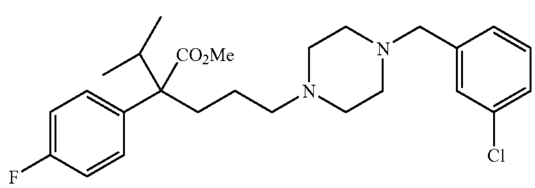 | 7.46-7.44 (m, 2H), 7.39-7.31 (m, 2H), 7.17 (dd, J=8.4, 5.4 Hz, 2H), 7.05-7.00 (m, 2H), 4.33 (s, 2H), 3.67 (s, 3H), 3.50 (m, 8H), 3.10-3.02 (m, 2H), 2.40-2.34 (m, 1H), 2.07-1.99 (m, 1H), 1.87-1.81 (m, 1H), 1.43-1.26 (m, 2H), 0.78 (d, J=6.6 Hz, 3H), 0.67 (d, J=6.6 Hz, 3H) |
| 80 | 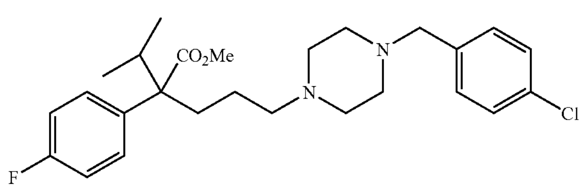 | 7.37 (dd, J=26.4, 8.4 Hz, 4H), 7.17 (dd, J=8.8, 5.4 Hz, 2H), 7.04-7.01 (m, 2H), 4.27 (s, 2H), 3.67 (s, 3H), 3.48-3.43 (m, 8H), 3.09-3.01 (m, 2H), 2.40-2.33 (m, 1H), 2.05-1.79 (m, 2H), 1.43-1.25 (m, 2H), 0.78 (d, J=6.8 Hz, 3H), 0.67 (d, J=6.7 Hz, 3H) |

TABLE 1-continued

| Embodiment | Structure | NMR |
|---|---|---|
| 81 | 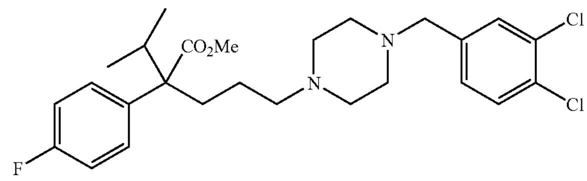 | 7.58-7.57 (m, 1H), 7.54 (d, J=8.2 Hz, 1H), 7.30 (dd, J=8.3, 1.9 Hz, 1H), 7.16 (dd, J=8.7. 5.4 Hz, 2H), 7.04-7.00 (m, 2H), 4.34 (s, 2H), 3.67 (s, 3H), 3.51 (m, 7H), 3.13-3.04 (m, 2H), 2.40-2.33 (m, 1H), 2.06-1.79 (m, 2H), 1.43-1.26 (m, 2H), 0.78 (d, J=6.6 Hz, 3H), 0.66 (d, J=6.7 Hz, 3H) |
| 82 | 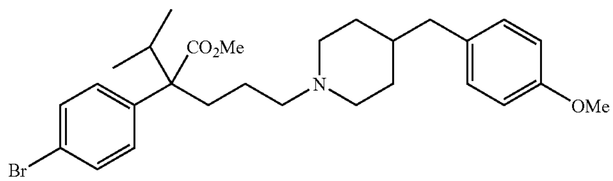 | 7.40 (d, J=8.6 Hz, 2H), 7.04 (dd, J=4.0, 8.7 Hz, 4H), 6.80 (d, J=8.6 Hz, 2H), 3.78 (s, 3H), 3.70 (s, 3H), 2.78 (d, J=10.7 Hz, 2H), 2.44 (d, J=7.1 Hz, 2H), 2.42-2.38 (m, 1H), 2.24-2.04 (m, 2H), 1.98-1.92 (m, 2H), 1.77-1.76 (m, 2H), 1.58 (d, J=11.9 Hz, 2H), 1.46-1.41 (m, 1H), 1.22-1.10 (m, 2H), 0.84 (d, J=6.8 Hz, 3H), 0.74 (d, J=6.8 Hz, 3H) |
| 83 | 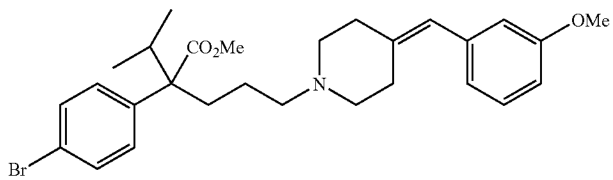 | 7.43 (d, J=8.6 Hz, 2H), 7.21 (t, J=7.8 Hz, 1H), 7.06 (d, J=8.6 Hz, 2H), 6.81-6.73 (m, 3H), 6.23 (s, 1H), 3.79 (s, 3H), 3.72 (s, 3H), 2.51-2.48 (m, 2H), 2.45-2.41 (m, 3H), 2.40-2.28 (m, 6H), 2.04-1.99 (m, 2H), 1.60 (m, 1H), 1.36-1.30 (m, 1H), 1.22-1.19 (m, 1H), 0.85 (d, J=6.7 Hz, 3H), 0.75 (d, J=6.8 Hz, 3H) |
| 84 | 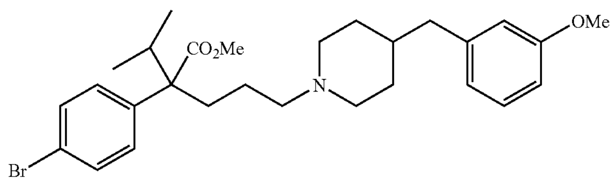 | 7.41 (d, J=8.6 Hz, 2H), 7.18 (t, J=7.8 Hz, 1H) 7.04 (d, J=8.7 Hz, 2H), 6.76-6.67 (m, 3H), 3.79 (s, 3H), 3.70 (s, 3H), 2.80 (m, 2H), 2.49 (d, J=7.1 Hz, 2H), 2.40-2.38 (m, 1H), 2.24 (m, 2H), 1.98-1.92 (m, 2H), 1.88-1.78 (m, 2H), 1.61 (d, J=11.8 Hz, 2H), 1.50-1.47 (m, 1H), 1.30-1.23 (m, 2H), 0.84 (d, J=6.7 Hz, 3H), 0.74 (d, J=6.8 Hz, 3H) |
| 85 | 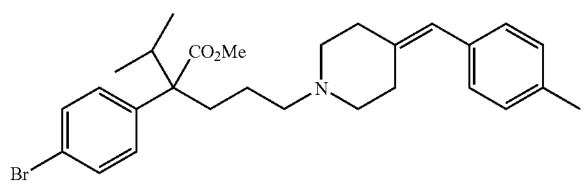 | 7.42 (d, J=6.6 Hz, 2H), 7.12-7.08 (m, 4H), 7.06 (d, J=6.7 Hz, 2H), 6.22 (s, 1H), 3.71 (s, 3H), 2.48-2.47 (m, 2H), 2.45-2.42 (m, 3H), 2.40-2.35 (m, 3H), 2.32 (s, 3H), 2.31-2.28 (m, 2H), 2.03-1.92 (m, 3H), 1.36-1.30 (m, 1H), 1.25-1.19 (m, 1H), 0.85 (d, J=6.7 Hz, 3H), 0.75 (d, J=6.8 Hz, 3H) |
| 86 | 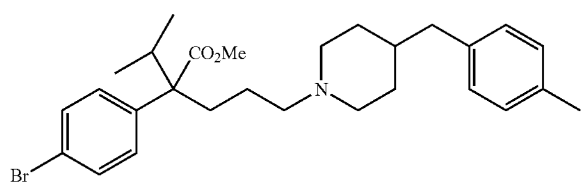 | 7.40 (d, J=8.7 Hz, 2H), 7.08-7.05 (m, 3H), 7.03-6.96 (m, 3H), 2.78 (d, J=11.4 Hz, 2H), 2.45 (d, J=7.1 Hz, 2H), 2.42-2.37 (m, 1H), 2.30 (s, 3H), 2.25-2.20 (m, 2H), 2.01-1.92 (m, 2H), 1.80-1.73 (m, 2H), 1.58 (d, J=11.9 Hz, 2H), 1.451.44 (m, 1H), 1.30-1.26 (m, 2H), 1.25-1.18 (m, 2H), 0.84 (d, J=6.7 Hz, 3H), 0.74 (d, J=6.8 Hz, 3H) |
| 87 | 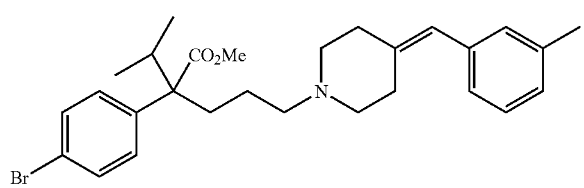 | 7.42 (d, J=8.7 Hz, 2H), 7.22-7.15 (m, 1H), 7.06 (d, J=8.6 Hz, 2H), 7.01-6.98 (m, 3H), 6.23 (s, 1H), 2.49-2.47 (m, 2H), 2.45-2.34 (m, 3H), 2.33 (s, 3H), 2.30-2.26 (m, 3H), 2.05-1.93 (m, 3H), 1.37-1.30 (m, 1H), 1.27-1.19 (m, 1H), 0.85 (d, J=6.7 Hz, 3H), 0.75 (d, J=6.8 Hz, 3H) |
| 88 | 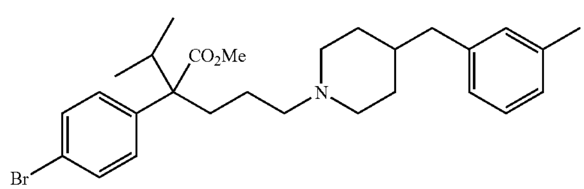 | 7.41 (d, J=8.7 Hz, 2H), 7.17-7.12 (m, 1H), 7.04 (d, J=8.7 Hz, 2H), 6.98 (d, J=7.5 Hz, 1H), 6.94-6.89 (m, 2H), 2.79 (d, J=11.4 Hz, 2H), 2.46 (d, J=7.0 Hz, 2H), 2.42-2.38 (m, 1H), 2.31 (s, 3H), 2.25-2.21 (m, 2H), 2.04-1.92 (m, 3H), 1.78-1.76 (m, 2H), 1.60 (d, J=11.8 Hz, 2H), 1.47 (m, 1H), 1.30-1.27 (m, 1H), 1.26-1.23 (m, 2H), 1.21-1.18 (m, 1H), 0.84 (d, J=6.7 Hz, 3H), 0.74 (d, J=6.8 Hz, 3H) |

TABLE 1-continued

| Embodiment | Structure | NMR |
|---|---|---|
| 89 | 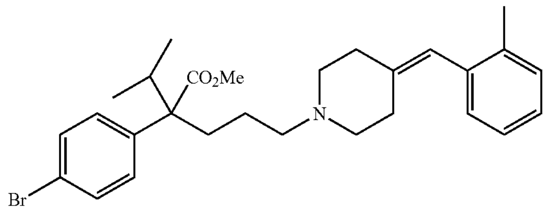 | 7.42 (d, J=8.7 Hz, 2H), 7.17-7.10 (m, 4H), 7.06 (d, J=8.7 Hz, 2H), 6.19 (s, 1H), 2.45-2.43 (m, 2H), 2.41-2.36 (m, 3H), 2.30 (s, 6H), 2.23 (s, 3H), 2.07-1.96 (m, 3H), 1.37-1.32 (m, 1H), 1.27-1.19 (m, 1H), 0.85 (d, J=6.7 Hz, 3H), 0.75 (d, J=6.8 Hz, 3H) |
| 90 | 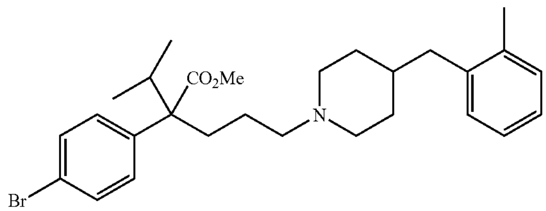 | 7.41 (d, J=8.7 Hz, 2H), 7.12-7.06 (m, 4H), 7.05 (d, J=8.7 Hz, 2H), 2.79 (d, J=11.5 Hz, 2H), 2.51 (d, J=7.0 Hz, 2H), 2.42-2.39 (m, 1H), 2.28 (s, 3H), 2.24-2.21 (m, 2H), 2.04-1.92 (m, 3H), 1.78-1.73 (m, 2H), 1.60 (d, J=11.8 Hz, 2H), 1.47-1.45 (m, 1H), 1.35-1.31 (m, 3H), 1.29-1.20 (m, 1H), 0.84 (d, J=6.7 Hz, 3H), 0.74 (d, J=6.8 Hz, 3H) |
| 91 | 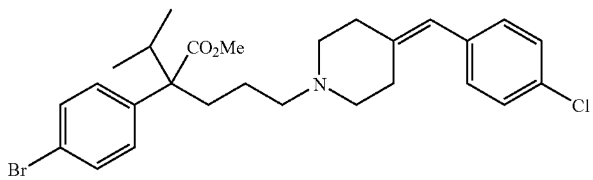 | 7.41 (d, J=8.6 Hz, 2H), 7.27-7.23 (m, 2H), 7.11-7.07 (m, 2H), 7.06 (d, J=8.7 Hz, 2H), 6.19 (s, 1H), 3.72 (s, 3H), 2.46-2.41 (m, 4H), 2.36-2.27 (m, 5H), 2.05-1.92 (m, 3H), 1.36-1.31 (m, 1H), 1.27-1.20 (m, 1H), 0.84 (d, J=6.7 Hz, 3H), 0.74 (d, J=6.8 Hz, 3H) |
| 92 | 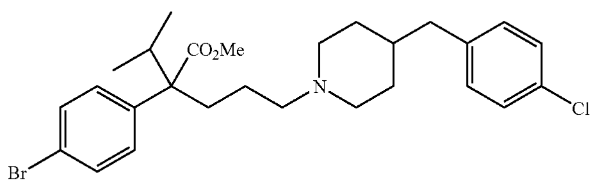 | 7.41 (d, J=8.7 Hz, 2H), 7.28-7.20 (m, 2H), 7.19-7.13 (m, 2H), 7.04 (d, J=8.7 Hz, 2H), 3.70 (s, 3H), 2.78 (d, J=11.3 Hz, 2H), 2.51 (d, J=7.0 Hz, 1H), 2.47 (d, J=7.1 Hz, 1H), 2.42-2.38 (m, 3H), 2.25-2.21 (m, 2H), 2.04-1.92 (m, 3H), 1.80-1.74 (m, 2H), 1.60-1.55 (m, 2H), 1.48-1.44 (m, 1H), 1.31-1.25 (m, 2H), 1.24-1.18 (m, 3H), 0.84 (d, J=6.7 Hz, 3H), 0.74 (d, J=6.8 Hz, 3H) |
| 93 | 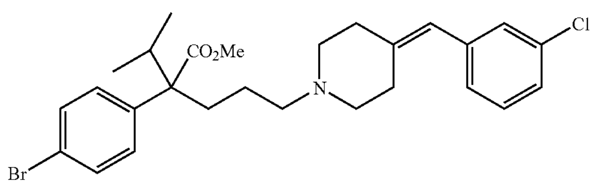 | 7.41 (d, J=8.6 Hz, 2H), 7.24-7.20 (m, 1H), 7.16-7.14 (m, 2H), 7.06 (d, J=8.7 Hz, 2H), 7.04-7.02 (m, 1H), 2.47-2.42 (m, 4H), 2.36-2.32 (m, 4H), 2.31-2.27 (m, 2H), 2.04-1.93 (m, 3H), 1.37-1.30 (m, 1H), 1.27-1.19 (m, 2H), 0.85 (d, J=6.7 Hz, 3H), 0.75 (d, J=6.8 Hz, 3H) |
| 94 | 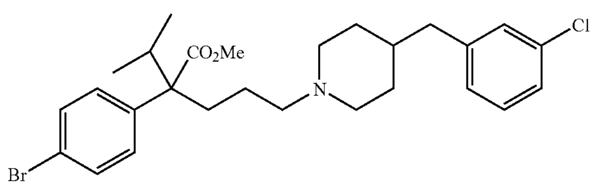 | 7.41 (d, J=8.7 Hz, 2H), 7.08-7.03 (m, 4H), 6.96-6.91 (m, 2H), 3.70 (s, 3H), 2.79 (d, J=11.5 Hz, 2H), 2.48 (d, J=7.1 Hz, 2H), 2.42-2.38 (m, 1H), 2.25-2.21 (m, 2H), 2.04-1.92 (m, 3H), 1.79-1.74 (m, 2H), 1.57 (d, J=11.8 Hz, 2H), 1.44 (m, 1H), 1.29-1.27 (m, 2H), 1.25-1.22 (m, 2H), 1.19 (m, 1H), 0.84 (d, J=6.7 Hz, 3H), 0.74 (d, J=6.8 Hz, 3H) |
| 95 | 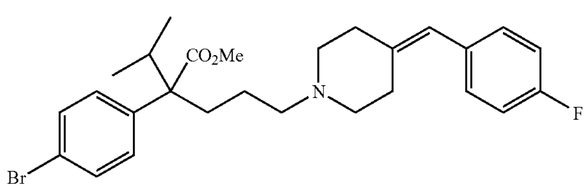 | 7.42 (d, J=8.7 Hz, 2H), 7.15-7.11 (m, 2H), 7.06 (d, J=8.7 Hz, 2H), 7.00-6.96 (m, 2H), 6.20 (s, 1H), 3.72 (s, 3H), 2.44-2.38 (m, 4H), 2.34-2.27 (m, 6H), 2.05-1.93 (m, 3H), 1.36-1.29 (m, 1H), 1.27-1.19 (m, 1H), 0.85 (d, J=6.7 Hz, 3H), 0.75 (d, J=6.8 Hz, 3H) |
| 96 | 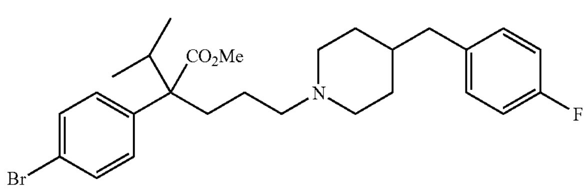 | 7.40 (d, J=8.6 Hz, 2H), 7.08-7.04 (m, 4H), 6.94 (d, J=8.7 Hz, 2H), 3.70 (s, 3H), 2.78 (d, J=7.1 Hz, 2H), 2.47 (d, J=7.1 Hz, 2H), 2.42-2.39 (m, 1H), 2.25-2.21 (m, 2H), 2.03-1.97 (m, 3H), 1.96-1.93 (m, 2H), 1.57 (d, J=8.0 Hz, 2H), 1.46-1.41 (m, 1H), 1.34-1.31 (m, 2H), 1.29-1.16 (m, 3H), 0.84 (d, J=6.7 Hz, 3H), 0.74 (d, J=6.8 Hz, 3H) |

TABLE 1-continued

| Embodiment | Structure | NMR |
|---|---|---|
| 97 | 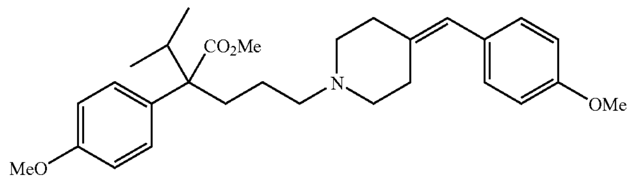 | 7.12-7.06 (m, 4H), 6.84 (dd, J=3.4, 8.8 Hz, 4H), 6.19 (s, 1H), 3.79 (s, 6H), 3.71 (s, 3H), 2.49-2.46 (m, 2H), 2.43-2.42 (m, 3H), 2.33-2.31 (m, 5H), 2.29-2.27 (m, 2H), 2.04-1.93 (m, 3H), 1.82-1.80 (m, 1H), 1.39-1.33 (m, 1H), 1-.30-1.22 (m, 2H), 0.85 (d, J=6.7 Hz, 3H), 0.76 (d, J=6.8 Hz, 3H) |
| 98 | 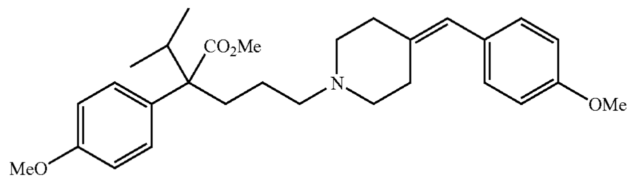 | 7.07 (d, J=8.8 Hz, 2H), 7.04 (d, J=8.6 Hz, 2H), 6.81 (dd, J=6.9, 8.8 Hz, 4H), 3.79 (s, 3H), 3.77 (s, 3H), 3.69 (s, 3H), 2.80 (d, J=11.4 Hz, 2H), 2.44 (d, J=7.0 Hz, 2H), 2.41-2.38 (m, 1H), 2.24 (t, J=7.4 Hz, 2H), 2.00-1.93 (m, 3H), 1.77-1.75 (m, 2H), 1.57 (d, J=12.7 Hz, 2H), 1.29-1.26 (m, 2H), 1.25-1.20 (m, 5H), 0.84 (d, J=6.7 Hz, 3H), 0.75 (d, J=6.8 Hz, 3H) |
| 99 | 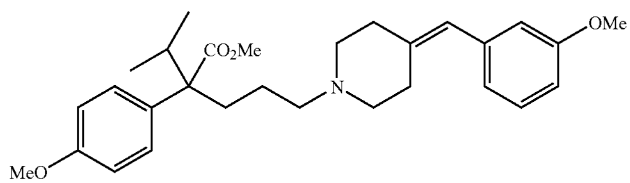 | 7.21 (t, J=7.8 Hz, 1H), 7.09 (d, J=8.8 Hz, 2H), 6.88 (dd, J=2.1, 8.8 Hz, 1H), 6.83 (d, J=8.8 Hz, 2H), 6.79-6.73 (m, 2H), 6.23 (s, 1H), 3.79 (s, 6H), 3.71 (s, 3H), 2.50-2.39 (m, 5H), 2.36-2.29 (m, 5H), 2.07-1.95 (m, 3H), 1.27-1.24 (m, 3H), 0.85 (d, J=6.7 Hz, 3H), 0.74 (d, J=6.8 Hz, 3H) |
| 100 | 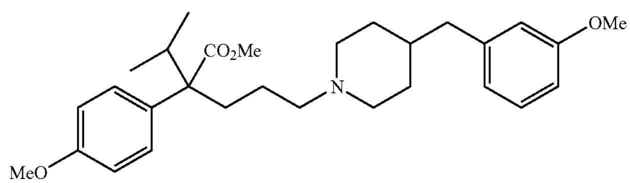 | 7.17 (t, J=7.8 Hz, 1H) 7.07 (d, J=8.8 Hz, 2H), 6.90-6.87 (m, 1H), 6.82 (d, J=8.8 Hz, 2H), 6.72-6.67 (m, 2H), 3.79 (s, 3H), 3.78 (s, 3H), 3.69 (s, 3H), 2.81 (d, J=11.0 Hz, 2H), 2.48 (d, J=7.0 Hz, 2H), 2.41-2.24 (m, 2H), 2.02-1.92 (m, 3H), 1.80 (m, 2H), 1.59 (d, J=13.0 Hz, 2H), 1.49-1.44 (m, 1H), 1.34-1.29 (m, 2H), 1.25-1.23 (m, 3H), 0.84 (d, J=6.7 Hz, 3H), 0.75 (d, J=6.8 Hz, 3H) |
| 101 | 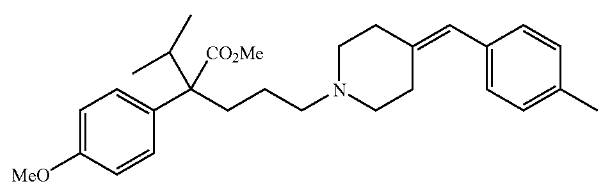 | 7.12-7.06 (m, 6H), 6.83 (d, J=8.9 Hz, 2H), 6.21 (s, 1H), 3.79 (s, 3H), 3.71 (s, 3H), 2.50-2.47 (m, 2H), 2.45-2.43 (m, 2H), 2.35-2.27 (m, 9H), 2.07-1.95 (m, 3H), 1.40-1.33 (m, 1H), 1.31-1.22 (m, 1H), 0.84 (d, J=6.6 Hz, 3H), 0.76 (d, J=6.6 Hz, 3H) |
| 102 | 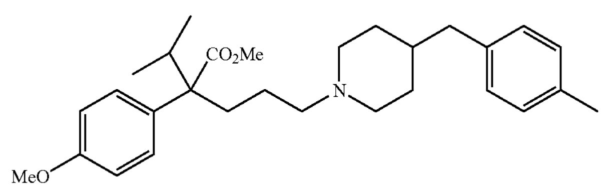 | 7.08-7.00 (m, 6H), 6.82 (d, J=8.0 Hz, 2H), 3.79 (s, 3H), 3.64 (s, 3H), 2.80 (d, J=10.4 Hz, 2H), 2.46 (d, J=6.6 Hz, 2H), 2.41-2.38 (m, 1H), 2.30 (s, 3H), 2.25-2.22 (m, 2H), 2.04-1.92 (m, 3H), 1.77 (m, 2H), 1.58 (d, J=12.2 Hz, 2H), 1.45 (m, 1H), 1.33-1.23 (m, 4H), 0.82 (d, J=6.3 Hz, 3H), 0.75 (d, J=6.4 Hz, 3H) |
| 103 | 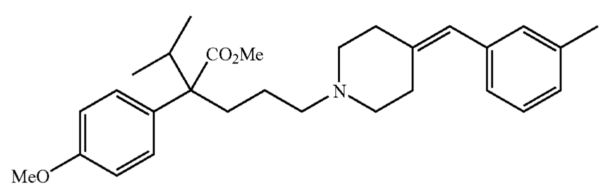 | 7.21-7.17 (m, 1H), 7.09 (d, J=8.9 Hz, 2H), 7.01-6.97 (m, 3H), 6.83 (d, J=8.8 Hz, 2H), 6.23 (s, 1H), 3.79 (s, 3H), 3.71 (s, 3H), 2.56-2.51 (m, 2H), 2.50-2.43 (m, 3H), 2.41-2.37 (m, 5H), 2.33 (s, 3H), 2.05-1.95 (m, 3H), 1.38 (m, 1H), 1.27-1.25 (m, 2H), 0.85 (d, J=6.7 Hz, 3H), 0.75 (d, J=6.8 Hz, 3H) |
| 104 | 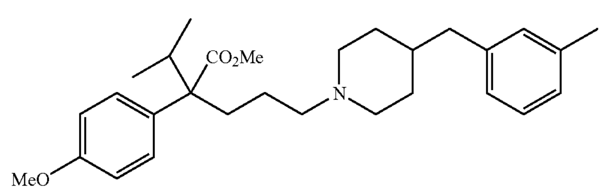 | 7.16-7.13 (m, 1H), 7.07 (d, J=8.9 Hz, 2H), 6.99-6.87 (m, 3H), 6.82 (d, J=8.9 Hz, 2H), 3.79 (s, 3H), 3.70 (s, 3H), 2.86 (d, J=12.8 Hz, 2H), 2.47 (d, J=6.9 Hz, 2H), 2.41-2.38 (m, 1H), 2.31 (s, 3H), 2.01-1.91 (m, 3H), 1.89-1.85 (m, 2H), 1.61 (d, J=13.5 Hz, 2H), 1.50-1.45 (m, 1H), 1.37-1.30 (m, 3H), 1.28-1.25 (m, 2H), 0.84 (d, J=6.7 Hz, 3H), 0.74 (d, J=6.7 Hz, 3H) |

TABLE 1-continued

| Embodiment | Structure | NMR |
|---|---|---|
| 105 | 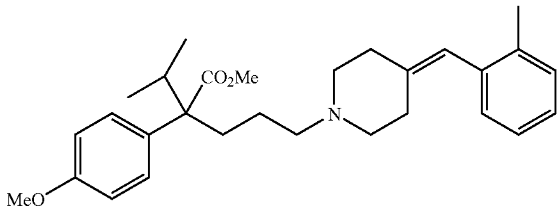 | 7.17 (m, 2H), 7.12 (dd, J=3.5, 5.7 Hz, 2H), 7.09 (d, J=8.8 Hz, 2H), 6.83 (d, J=8.8 Hz, 2H), 6.19 (s, 1H), 3.79 (s, 3H), 3.71 (s, 3H), 2.48-2.47 (m, 2H), 2.44-2.37 (m, 3H), 2.31-2.30 (m, 6H), 2.23 (s, 3H), 2.05-1.96 (m, 3H), 1.37-1.39 (m, 1H), 1.28-1.25 (m, 2H), 0.84 (d, J=6.7 Hz, 3H), 0.74 (d, J=6.8 Hz, 3H) |
| 106 | 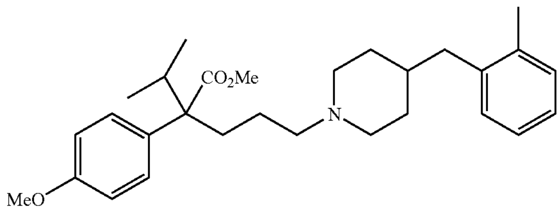 | 7.13-7.04 (m, 6H), 6.82 (d, J=8.8 Hz, 2H), 3.79 (s, 3H), 3.70 (s, 3H), 2.83 (d, J=11.0 Hz, 2H), 2.51 (d, J=6.9 Hz, 2H), 2.42-2.38 (m, 1H), 2.28 (s, 3H), 2.02-1.92 (m, 3H), 1.80-1.79 (m, 2H), 1.61 (d, J=12.6 Hz, 2H), 1.48 (m, 1H), 1.38-1.32 (m, 3H), 1.25-1.24 (m, 2H), 0.84 (d, J=6.7 Hz, 3H), 0.75 (d, J=6.8 Hz, 3H) |
| 107 | 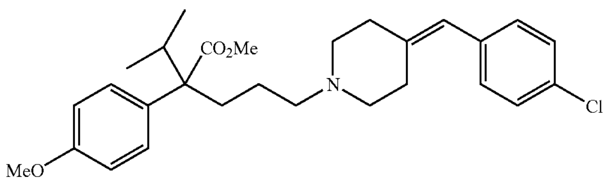 | 7.25 (d, J=8.9 Hz, 2H), 7.09 (dd, J=3.0, 8.9 Hz, 4H), 6.83 (d, J=8.9 Hz, 2H), 6.19 (s, 1H), 3.79 (s, 3H), 3.71 (s, 3H), 2.46-2.44 (m, 3H), 2.39-2.30 (m, 5H), 2.05-1.95 (m, 3H), 1.38 (m, 1H), 1.27-1.24 (m, 2H), 0.85 (d, J=6.7 Hz, 3H), 0.76 (d, J=6.8 Hz, 3H) |
| 108 | 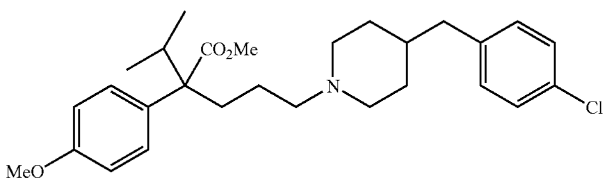 | 7.24-7.11 (m, 4H), 7.07 (d, J=8.8 Hz, 2H), 6.82 (d, J=8.8 Hz, 2H), 3.79 (s, 3H), 3.69 (s, 3H), 2.82 (d, J=9.6 Hz, 2H), 2.51 (d, J=7.1 Hz, 1H), 2.47 (d, J=7.0 Hz, 1H), 2.41-2.38 (m, 1H), 2.26 (m, 2H), 1.60 (d, J=12.8 Hz, 2H), 1.55-1.49 (m, 1H), 1.33-1.24 (m, 4H), 0.84 (d, J=6.7 Hz, 3H), 0.74 (d, J=6.8 Hz, 3H) |
| 109 | 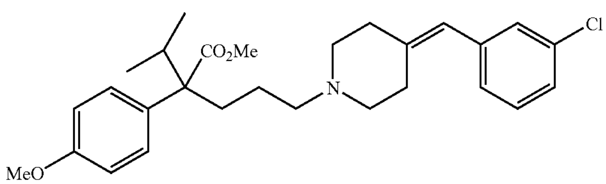 | 7.22-7.20 (m, 1H), 7.16-7.14 (m, 2H), 7.09 (d, J=8.8 Hz, 2H), 7.06-7.04 (m, 1H), 6.83 (d, J=8.8 Hz, 2H), 6.18 (s, 1H), 3.79 (s, 3H), 3.71 (s, 3H), 2.47-2.44 (m, 4H), 2.43-2.36 (m, 4H), 2.32-2.28 (m, 2H), 2.05-1.95 (m, 3H), 1.27-1.24 (m, 2H), 0.85 (d, J=6.7 Hz, 3H), 0.76 (d, J=6.8 Hz, 3H) |
| 110 | 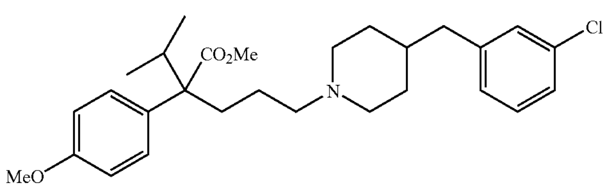 | 7.27-7.24 (m, 1H), 7.18-7.13 (m, 3H), 7.07 (d, J=8.9 Hz, 2H), 6.82 (d, J=8.9 Hz, 2H), 3.79 (s, 3H), 3.69 (s, 3H), 2.80 (d, J=11.4 Hz, 2H), 2.51 (d, J=7.1 Hz, 2H), 2.51-2.41 (m, 1H), 2.24 (t, J=7.2 Hz, 2H), 2.01-1.92 (m, 3H), 1.78-1.76 (m, 2H), 1.58 (d, J=12.6 Hz, 2H), 1.48 (m, 1H), 1.32-1.21 (m, 3H), 0.84 (d, J=6.7 Hz, 3H), 0.74 (d, J=6.8 Hz, 3H) |
| 111 | 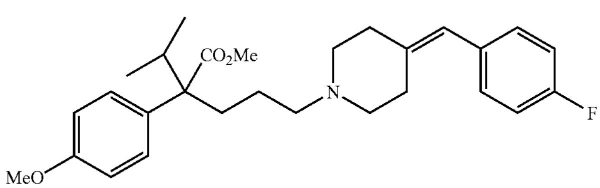 | 7.12-7.11 (m, 2H), 7.09 (d, J=8.9 Hz, 2H), 7.00-6.95 (m, 2H), 6.83 (d, J=8.9 Hz, 2H), 6.20 (s, 1H), 3.79 (s, 3H), 3.71 (s, 3H), 2.46-2.43 (m, 4H), 2.41-2.35 (m, 4H), 2.32-2.28 (m, 2H), 2.05-1.95 (m, 3H), 1.37-1.25 (m, 2H), 0.85 (d, J=6.7 Hz, 3H), 0.75 (d, J=6.8 Hz, 3H) |
| 112 | 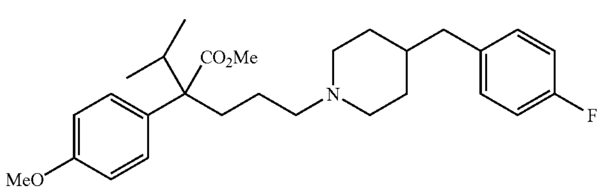 | 7.14-7.04 (m, 4H), 6.98-6.91 (m, 2H), 6.82 (d, J=8.9 Hz, 2H), 3.79 (s, 3H), 3.69 (s, 3H), 2.81 (d, J=11.4 Hz, 2H), 2.47 (d, J=7.0 Hz, 2H), 2.41-2.38 (m, 1H), 2.25 (t, J=7.1 Hz, 2H), 2.02-1.92 (m, 3H), 1.81-1.77 (m, 2H), 1.57 (d, J=13.0 Hz, 2H), 1.44 (m, 1H), 1.30-1.22 (m, 4H), 0.84 (d, J=6.7 Hz, 3H), 0.75 (d, J=6.8 Hz, 3H) |

Experimental Example 1

Measurement of Ion Current Inhibition on T-Type Calcium Ion Channels Using a Patch Clamp (1) Cell Culture and Preparation HEK293 cell strains ($a_{1G}$ cell strain: KCTC 10519BP), in which $\alpha_{1G}$ T-type calcium ion channels and Kir2.1 channels were stably expressed, were obtained from the GenBank of Korea Research Institute of Bioscience & Biotechnology (KRIBB). In a cell culture device provided with 95% oxygen and 5% carbon dioxide, T-type calcium ion channel expressed cells were cultured in Dulbecco's modified Eagle's medium (DMEM) supplemented with 10% fetal bovine serum (FBS), and hERG channels were cultured in MEM supplemented with 10% FBS. 20 hours prior to the use of the medium for expression of hERG channels, the Tet-expression system was activated by treating the medium with 1 μg/ml doxycycline.

The cells in the experiment was passaged once in three days, and collected when the cells were grown to 50~80% confluency in the Petri dish. Prior to the experiment, the cells were separated from the dish using trypsin-EDTA (0.25×) and a single cell was prepared using a pippet. Trypsin was removed using a centrifuge, an extracellular solution was added, and cells floating automatically by a Patchliner were used at room temperature.

(2) Experimental Solution

As a solution composition for measurement of activation of T-type calcium ion channels, 140 mM NaCl, 2 mM $CaCl_2$, 4 mM KCl, 1 mM $MgCl_2$, 5 mM D-glucose, and 10 mM HEPES (pH 7.4) were used for an extracellular solution, and 50 mM KCl, 10 mM NaCl, 60 mM KF, 2 mM MgCl2, 10 mM HEPES, and 20 mM EGTA (pH 7.2) were used for an intracellular solution. To maintain the pre-cellular state, a seal reinforced solution was added. When T-type calcium ion channel expression cells were used, an extracellular solution supplemented with 10 mM $Ba^{2+}$ was added and records about the result were made. A 100 mM stock solution was prepared by dissolving each experimental compound in dimethylsulfoxide (DMSO), and $IC_{50}$ was measured after the solution was diluted with an extracellular solution supplemented with $Ba^{2+}$ at 10 nM to 100 μM.

(3) Electro-Physiological Technique and Data Processing

The current was measured through an EPC10 amplifier (HEKA, Germany) by a precellular patch clamp technique using NPC©-16 Patchliner (Nanion Technologies, Germany). Cell suspensions and various experimental solutions were automatically aliquotted into chips (NPC-16 Chip, Nanion Technologies, Germany) by experimental devices. A cell membrane potential was fixed at −100 mV for measurement of activation of T-type calcium ion channels. When a low polarization was performed at −20 mV for 300 ms, the inward current was measured at ten-second intervals.

Cells were treated in the compounds in Embodiments 1, 4, 5, 10~13, 23, 26, 30~32, 34, 35, and 38~40 at each concentration for about 20 seconds, and mibefradil, useful as a T-type calcium ion channel inhibitor, was used as a control group. The IC50 graphs and values were obtained from the automatic calculation of inhibition rates of the peak current using an experimental data analysis program IGOR Pro (WaveMetrics, USA). The results were indicated in the following Table 2.

TABLE 2

| Division | % inhibition rate (10 μM) | IC50 (μM) |
| --- | --- | --- |
| Embodiment 1 | 96.9 ± 0.59 | 8.17 ± 0.48 (nM) |
| Embodiment 4 | 93.5 ± 3.2 | 0.19 ± 0.001 |
| Embodiment 5 | 91.7 ± 1.9 | 0.88 ± 0.07 |
| Embodiment 10 | 98.3 ± 0.9 | 0.25 ± 0.005 |
| Embodiment 11 | 91.4 ± 0.4 | 0.10 ± 0.01 |
| Embodiment 12 | 94.2 ± 0.4 | 53.02 ± 4.87 (nM) |
| Embodiment 13 | 94.5 ± 1.2 | 0.25 ± 0.01 |
| Embodiment 23 | 96.3 ± 1.7 | 0.34 ± 0.02 |
| Embodiment 26 | 94.0 ± 2.5 | 0.26 ± 0.03 |
| Embodiment 30 | 90.4 ± 3.2 | 0.74 ± 0.02 |
| Embodiment 31 | 89.3 ± 1.6 | 0.98 ± 0.11 |
| Embodiment 32 | 96.5 ± 1.7 | 1.11 ± 0.05 |
| Embodiment 34 | 93.0 ± 1.5 | 0.28 ± 0.02 |
| Embodiment 35 | 94.1 ± 1.5 | 95.04 ± 14.78 (nM) |
| Embodiment 38 | 96.0 ± 1.7 | 0.48 ± 0.08 |
| Embodiment 39 | 95.1 ± 1.9 | 0.32 ± 0.01 |
| Embodiment 40 | 94.9 ± 1.5 | 0.39 ± 0.03 |
| Control group (mibefradil) | 95.9 ± 1.7 | 1.34 ± 0.49 |

As indicated in Table 2, the calcium ion channel inhibitory activation ($IC_{50}$) of the phenylacetate derivatives according to the present invention is 53.02±4.87 nM~0.98±0.11 μM. It can be known that they show better calcium ion channel inhibitory activation, compared to mibefradil (1.34±0.49 μM) as a T-type calcium ion channel inhibitor in the art.

Thus, the composition according to the present invention effectively inhibits the T-type calcium ion channel activation and may be useful for prevention or treatment of diseases such as hypertension, cancer, epilepsy, and neurogenic pains related with T-type calcium channels.

The phenylacetate derivatives represented by the Chemical Formula 1 may be formulated in various forms according to the intended purpose: The following examples illustrate several preparation methods including the compound represented in the Chemical Formula 1, but the present invention should not be limited to this.

Preparation Example #1

Tablets (Direct Compression)

5.0 mg of an active ingredient was sieved, followed by preparation of tablets by mixing and compressing 14.1 mg of lactose, 0.8 mg of CrossPovidone USNF, and 0.1 mg of magnesium stearate.

Preparation Example #2

Tablets (Wet Granulation)

5.0 mg of an active ingredient was sieved, followed by mixing 16.0 mg of lactose and 4.0 mg of starch. 0.3 mg of Polysolvate 80 was dissolved in purified water, and by microgranulation, by adding the appropriate amount of the solution. The microgranules were dried and sieved, followed by mixing 2.7 mg of colloidal silicon dioxide and 2.0 mg of magnesium stearate. Tablets were prepared by compressing the compounds.

Preparation Example #3

Powders and Capsules 5.0 mg of an active ingredient was sieved, followed by mixing 14.8 mg of lactose, 10.0 mg of polyvinyl pyrrolidone, and 0.2 mg of magnesium stearate with it. The compound was filled into a hard No. 5 gelatin capsule using an appropriate apparatus.

Preparation #4

Injections

Injection was prepared by containing 100 mg of an active ingredient, as well as 180 mg of mannitol, 26 mg of $Na_2HPO_4.12H_2O$, and 2947 mg of distilled water.

What is claimed is:

1. A phenylacetate derivative represented by the following Chemical Formula 1, or pharmaceutically acceptable salt thereof:

[Chemical Formula 1]

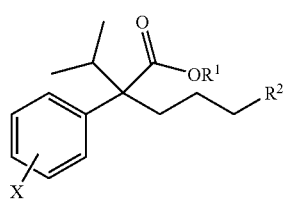

wherein,
X is independently or selectively one or more substituents selected from the group consisting of H, halogen, and a $C_{1-4}$ alkoxy;
$R^1$ is a $C_{1-4}$ linear or branched alkyl; and
$R^2$ is

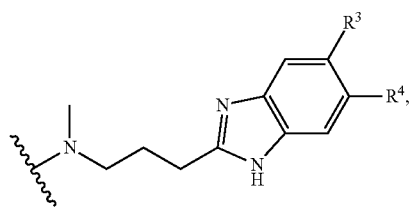

wherein $R^3$ and $R^4$ are independently or selectively H, a $C_{1-4}$ linear or branched alkyl, or a $C_{1-4}$ alkoxy.

2. The phenylacetate derivative or pharmaceutically acceptable salt thereof as set forth in claim 1, wherein
X is independently or selectively one or more substituents selected from the group consisting of H, fluoride, chloride, bromide, methoxy and ethoxy;
$R^1$ is methyl, ethyl, propyl, and isopropyl; and
$R^2$ is

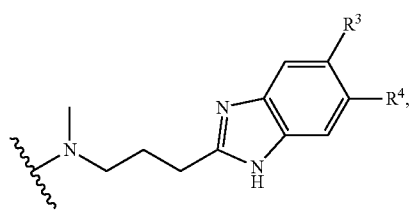

wherein $R^3$ and $R^4$ are independently or selectively H, methyl, ethyl, methoxy or ethoxy.

3. The phenylacetate derivative or pharmaceutically acceptable salt thereof as set forth in claim 1, wherein
X is one or more substituents selected from the group consisting of H, fluoride, bromide and ethoxy;
$R^1$ is methyl or ethyl; and
$R^2$ is

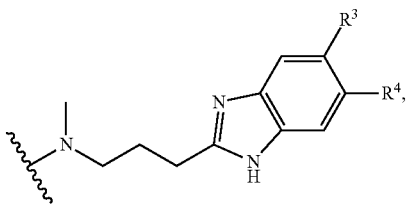

wherein $R^3$ and $R^4$ are independently or selectively H, methyl or methoxy.

4. The phenylacetate derivative or pharmaceutically acceptable salt thereof as set forth in claim 1, wherein the phenylacetate derivative is selected from the group consisting of:
(1) 5-{[3-(1H-benzimidazole-2-yl)propyl]methylamino}-2-(4-bromophenyl)-2-isopropylpentanoic acid methyl ester;
(2) methyl 5-((3-(1H-benzo[d]imidazole-2-yl)propyl)(methyl))amino)-2-isopropyl-2-(4-methoxyphenyl) pentanoate;
(3) methyl 2-isopropyl-5-((3-(5-methoxy-1H-benzo[d]imidazole-2-yl)propyl)(methyl))amino)-2-(4-methoxyphenyl)pentanoate;
(4) methyl 5-((3-(5,6-dimethyl-1H-benzo[d]imidazole-2-yl)propyl)(methyl))amino)-2-isopropyl-2-(4-methoxyphenyl)pentanoate;
(5) methyl 5-((3-(1H-benzo[d]imidazole-2-yl)propyl)(methyl))amino)-2-(3,4-dimethoxyphenyl)-2-isopropylpentanoate;
(6) methyl 2-(3,4-dimethoxyphenyl)-2-isopropyl-5-((3-(5-methoxy-1H-benzo[d]imidazole-2-yl)propyl)(methyl))amino)pentanoate;
(7) methyl 2-(3,4-dimethoxyphenyl)-5-((3-(5,6-dimethyl-1H-benzo[d]imidazole-2-yl)propyl)(methyl))amino)-2-isopropylpentanoate;
(8) ethyl 5-((3-(1H-benzo[d]imidazole-2-yl)propyl)(methyl))amino)-2-isopropyl-2-phenylpentanoate;
(9) ethyl 5-((3-(5,6-dimethyl-1H-benzo[d]imidazole-2-yl)propyl)(methyl))amino)-2-isopropyl-2-phenylpentanoate;
(10) methyl 2-(4-bromophenyl)-5-((3-(5,6-dimethyl-1H-benzo[d]imidazole-2-yl)propyl)(methyl))amino)-2-isopropylpentanoate;
(11) methyl 2-(4-bromophenyl)-2-isopropyl-5-((3-(5-methoxy-1H-benzo[d]imidazole-2-yl)propyl)(methyl))amino)pentanoate;
(12) methyl 5-((3-(1H-benzo[d]imidazole-2-yl)propyl)(methyl))amino)-2-(3-bromophenyl)-2-isopropylpentanoate;
(13) methyl 2-(3-bromophenyl)-2-isopropyl-5-((3-(5-methoxy-1H-benzo[d]imidazole-2-yl)propyl)(methyl))amino)pentanoate;
(14) methyl 2-(3-bromophenyl)-5-((3-(5,6-dimethyl-1H-benzo[d]imidazole-2-yl)propyl)(methyl))amino)-2-isopropylpentanoate;
(15) methyl 5-((3-(1H-benzo[d]imidazole-2-yl)propyl)(methyl))amino)-2-(4-fluorophenyl)-2-isopropylpentanoate;

(16) methyl 2-(4-fluorophenyl)-2-isopropyl-5-((3-(5-methoxy-1H-benzo[d]imidazole-2-yl)propyl)(methyl))amino)pentanoate; and

(17) methyl 5-((3-(5,6-dimethyl-1H-benzo[d]imidazole-2-yl)propyl)(methyl))amino)-2-(4-fluorophenyl)-2-isopropylpentanoate.

5. A method for preparing the phenylacetate derivative of claim 1 as represented by the following Chemical Formula 1, comprising:

preparing an ester compound of Chemical Formula 3 by esterification reaction of a carboxyl acid compound of Chemical Formula 2 as a starting material in the presence of an acid catalyst (Step 1);

preparing a compound of Chemical Formula 4 by reacting the compound of Chemical Formula 3 obtained from step 1 with t-butoxide and isopropyl bromide (Step 2);

preparing a compound of Chemical Formula 5 by reacting the compound of Chemical Formula 4 obtained from step 2 with 1,3-dibromopropane (Step 3); and preparing a compound of Chemical Formula 1 by reacting the compound of Chemical Formula 5 obtained from step 3 with a compound of Chemical Formula 6 (Step 4),

[Chemical Formula 1]

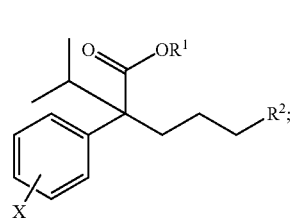

[Chemical Formula 2]

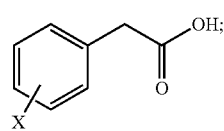

[Chemical Formula 3]

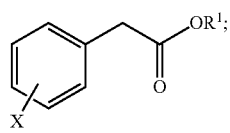

[Chemical Formula 4]

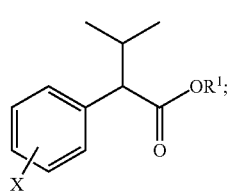

[Chemical Formula 5]

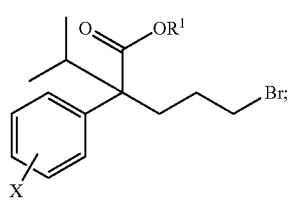

-continued

[Chemical Formula 6]

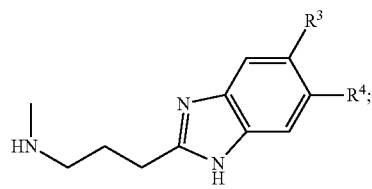

wherein, $R^1$, $R^2$, $R^3$, $R^4$, and X are as defined in claim 1.

6. The method as set forth in claim 5, wherein, in Step 1, after the carboxyl acid compound of Chemical Formula 2 is dissolved in methanol, the compound of Chemical Formula 3 is obtained by heating or refluxing the mixture at 85-95° C. in the presence of sulfuric acid for 2-4 hours.

7. The method as set forth in claim 5, wherein, in Step 2, after the compound of Chemical Formula 3 and t-butoxide is dissolved in anhydrous dimethylformamide, the compound of Chemical Formula 4 is obtained by adding isopropyl bromide into the mixture and stirring the mixture at room temperature for 2-4 hours.

8. The method as set forth in claim 5, wherein, in Step 3, after a solution of n-butyllithium in hexane is added to a solution of diisopropylamine in anhydrous tetrahydrofuran at −75--80° C., the compound of Chemical Formula 5 is obtained by adding the compound of Chemical Formula 4 to the tetrahydrofuran solution with stirring, adding 1,3-dibromopropane dropwise to the tetrahydrofuran solution, and stirring the solution at room temperature overnight.

9. The method as set forth in claim 5, wherein, in Step 4 when the compound of Chemical Formula 5 is reacted with the compound of Chemical Formula 6, the compound of Chemical Formula 1 is obtained by dissolving the compound of Chemical Formula 5 into methanol, adding the compound of Chemical Formula 6 and potassium carbonate, and heating or refluxing the mixture at 85-95° C. for 2-4 hours.

10. A phenylacetate derivative intermediate represented by the following Chemical Formula 3, Chemical Formula 4, or Chemical Formula 5:

[Chemical Formula 3]

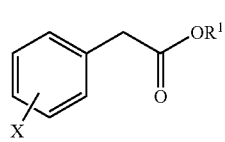

[Chemical Formula 4]

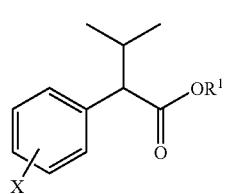

[Chemical Formula 5]
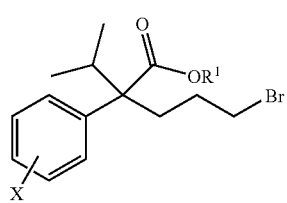
wherein
X is independently or selectively one or more substituents selected from the group consisting of H, halogen, and a $C_{1-4}$ alkoxy;
$R^1$ is a $C_{1-4}$ linear or branched alkyl; and
$R^2$ is
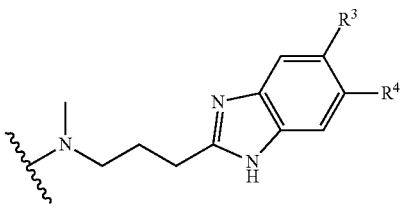
wherein $R^3$ and $R^4$ are independently or selectively H, a $C_{1-4}$ linear or branched alkyl, or a $C_{1-4}$ alkoxy.
* * * * *